(12) United States Patent
Arthos et al.

(10) Patent No.: US 7,368,114 B2
(45) Date of Patent: May 6, 2008

(54) FUSION PROTEIN INCLUDING OF CD4

(75) Inventors: James Arthos, Rockville, MD (US);
Claudia Cicala, Bethesda, MD (US);
Anthony S. Fauci, Washington, DC (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 144 days.

(21) Appl. No.: 10/493,676

(22) PCT Filed: Oct. 24, 2002

(86) PCT No.: PCT/US02/34393

§ 371 (c)(1),
(2), (4) Date: Jul. 27, 2004

(87) PCT Pub. No.: WO03/040311

PCT Pub. Date: May 15, 2003

(65) Prior Publication Data
US 2004/0265306 A1 Dec. 30, 2004

Related U.S. Application Data

(60) Provisional application No. 60/346,231, filed on Oct. 25, 2001.

(51) Int. Cl.
*A61K 39/00* (2006.01)
*A61K 38/00* (2006.01)
*C12P 21/08* (2006.01)

(52) U.S. Cl. .................. 424/192.1; 530/300; 530/387.3
(58) Field of Classification Search .............. 424/138.1
See application file for complete search history.

(56) References Cited

U.S. PATENT DOCUMENTS

| | | |
|---|---|---|
| 5,116,964 A | 5/1992 | Capon et al. |
| 5,126,433 A | 6/1992 | Maddon et al. |
| 5,336,603 A | 8/1994 | Capon et al. |
| 5,422,274 A | 6/1995 | Maddon et al. |
| 5,714,147 A | 2/1998 | Capon et al. |
| 5,817,767 A | 10/1998 | Allaway et al. |
| 6,034,223 A | 3/2000 | Maddon et al. |
| 6,083,478 A | 7/2000 | Allaway et al. |
| 6,117,655 A | 9/2000 | Capon et al. |
| 6,177,549 B1 | 1/2001 | Maddon et al. |
| 6,187,748 B1 * | 2/2001 | Maddon et al. ................ 514/12 |

FOREIGN PATENT DOCUMENTS

| | | | |
|---|---|---|---|
| WO | WO 92/13559 | * | 2/1992 |
| WO | 92/21755 | | 12/1992 |
| WO | 97/47732 | | 12/1997 |
| WO | WO 00/55207 | | 9/2000 |

OTHER PUBLICATIONS

Smith. et al. "Addition of a m-tailpiece to IgG results in polymeric antibodies with enhanced effector functions including complement-mediated cytolysis by IgG4" J. Immunology, vol. 154(1995), pp. 2226-2236.*
Sorensen V. et al. "Effect of the IgM and IgA secretory tailpiece on polymerization and secretion of IgM and IgG" J. Immunology Vo. 156(1996), pp. 2858-2865.*
Traunecker A. et al. "High efficient neutralization of HIV with recombinant CD4-immunoglobulin molecules" Nature, vol. 230, p. 68-70, (1989).*
Chaikin et al., *Journal of Allergy and Clinical Immunology* 99(1):835, Part 2, Suppl., 1997.
Jacobson et al., *Journal of Infectious Diseases* 182:326-329, 2000.
Sakihama et al., *Proc. Natl. Acad. Sci. USA* 92:6444-6448, 1995.
Sørensen et al., *The Journal of Immunology* 162:3448-3455, 1999.
Arthos et al., "Biochemical and biological characterization of a dodecameric CD4-Ig fusion protein: implications for therapeutic and vaccine strategies," *J Biol Chem* 277(13):11456-11464, 2002.
Chaikin et al., "Hexameric CD80 and CD86-Ig Fusion Proteins," *Journal of Allergy and Clinical Immunology* 99(1) part 2:S206; & Joint Meeting of the American Academy of Allergy, Asthma and Immunology, the American Association of; San Francisco, CA, USA; Feb. 21-26, 1997 (abstract only).
Sørensen et al., "Effect of the IgM and IgA secretory tailpieces on polymerization and secretion of IgM and IgG," *J Immunol* 156:2858-2865, 1996.
Traunecker et al., "Highly efficient neutralization of HIV with recombinant CD4-immunoglobulin molecules," *Nature* 339:68-70, 1989.

* cited by examiner

*Primary Examiner*—Bruce Campell
*Assistant Examiner*—Bo Peng
(74) *Attorney, Agent, or Firm*—Klarquist Sparkman, LLP

(57) ABSTRACT

Novel recombinant polypeptides are disclosed herein that include a CD4 polypeptide ligated at its C-terminus with a portion of an immunoglobulin comprising a hinge region and a constant domain of a mammalian immunoglobulin heavy chain. The portion or the IgG is fused at its C-terminus with a polypeptide comprising a tailpiece from the C-terminus of the heavy chain of an IgA antibody ara tailpiece from a C-terminus of the heavy chain of an IgM antibody. Also disclosed herein are methods for using these CD4 fusion proteins.

16 Claims, 14 Drawing Sheets figure 1
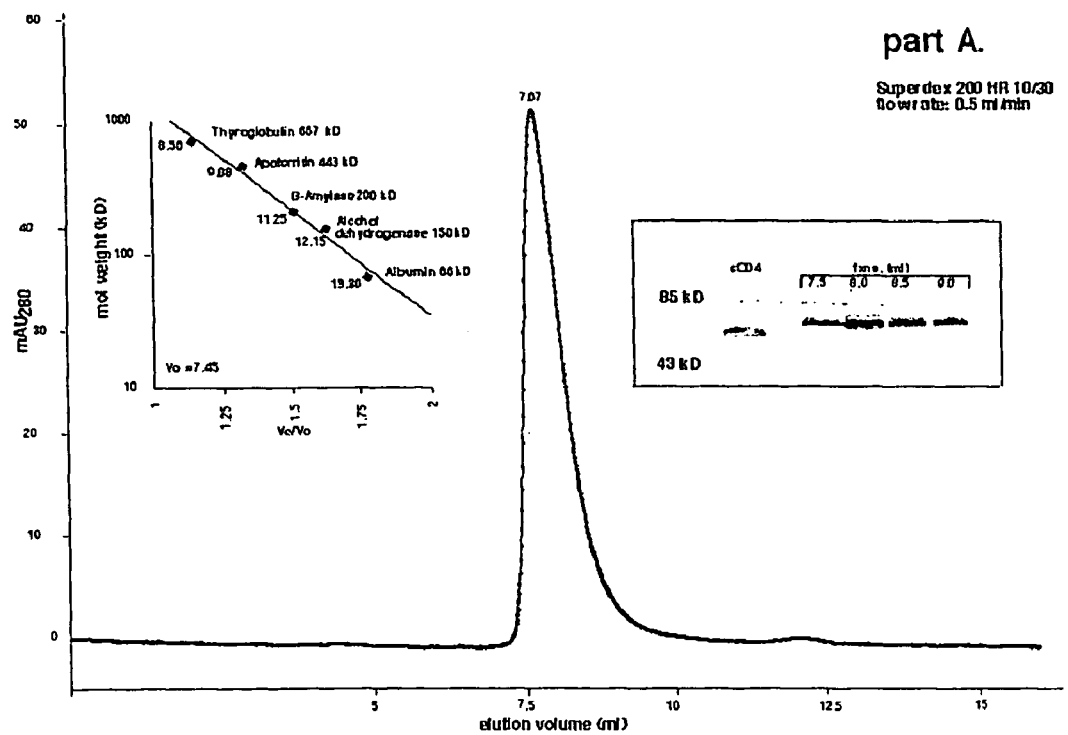
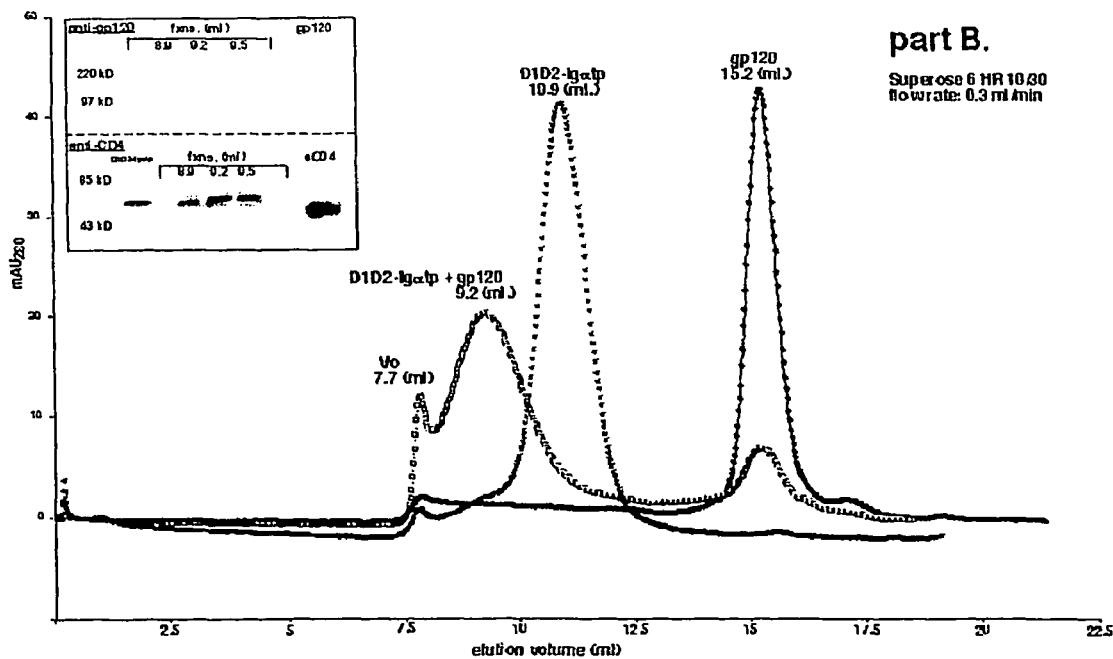

figure 8

| ISOLATE | IC$_{90}$ D1D2Ig-αtp | | IC$_{90}$ sCD4 | |
|---|---|---|---|---|
| | nM | ug/mL | nM | ug/mL |
| 1 Mey | 1 | 0.56 | >2400 | >50 |
| 2 Wal | 1.4 | 1.125 | >2400 | >50 |
| 3 Her | <1 | <0.56 | >2400 | >50 |
| 4 Brn | <2.8 | <2.25 | >2400 | >50 |
| Bal | <1 | <0.56 | >480 | >10 |
| JRFL | 1 | 0.56 | >2400 | >50 |

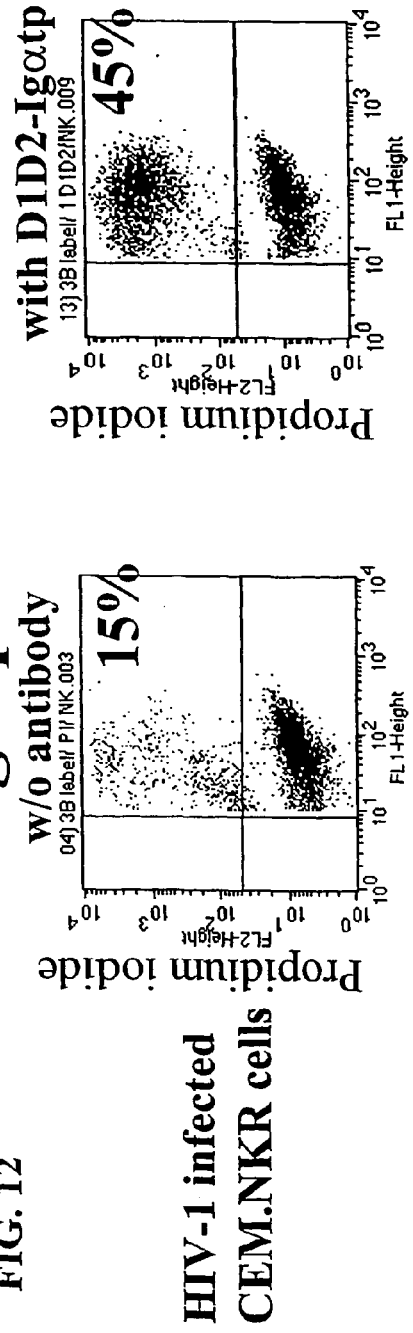
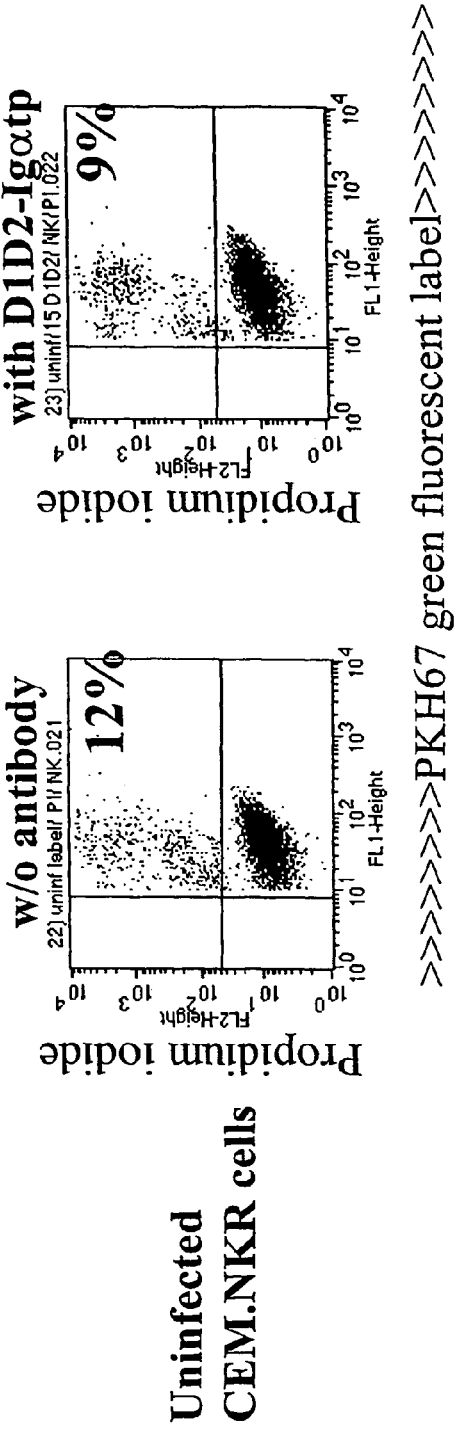
FIG. 12
D1D2-Igαtp mediates ADCC

Construction of a Chimeric IgG1/IgG2 Derivative of D1D2-Igαtp

IgG1  Glu Leu Leu Gly Gly Pro
IgG2  Pro Val --- Ala Gly Pro

SEQUENCE LISTING

<160> NUMBER OF SEQ ID NOS: 11

<210> SEQ ID NO 1
<211> LENGTH: 18
<212> TYPE: PRT
<213> ORGANISM: Artificial Sequence
<220> FEATURE:
<223> OTHER INFORMATION: Alpha tailpiece

<400> SEQUENCE: 1

Pro Thr His Val Asn Val Ser Val Val Met Ala Glu Val Asp Gly Thr
1               5                   10                  15

Cys Tyr

<210> SEQ ID NO 2
<211> LENGTH: 23
<212> TYPE: DNA
<213> ORGANISM: Artificial Sequence
<220> FEATURE:
<223> OTHER INFORMATION: Oligonucleotide primer/probe

<400> SEQUENCE: 2
gctaactagg gaacccactg ctt                                           23

<210> SEQ ID NO 3
<211> LENGTH: 23
<212> TYPE: DNA
<213> ORGANISM: Artificial Sequence
<220> FEATURE:
<223> OTHER INFORMATION: Oligonucleotide primer/probe

<400> SEQUENCE: 3
acaacagacg ggcacacact act                                           23

<210> SEQ ID NO 4
<211> LENGTH: 30
<212> TYPE: DNA
<213> ORGANISM: Artificial Sequence
<220> FEATURE:
<223> OTHER INFORMATION: Oligonucleotide primer/probe

<400> SEQUENCE: 4
agcctcaata aagcttgcct tgagtgcttc                                    30

<210> SEQ ID NO 5
<211> LENGTH: 1353
<212> TYPE: DNA
<213> ORGANISM: Artificial Sequence
<220> FEATURE:
<223> OTHER INFORMATION: D1D2-Igatp
<220> FEATURE:
<221> NAME/KEY: CDS
<222> LOCATION: (1)..(1353)

<400> SEQUENCE: 5 atg aac cgg gga gtc cct ttt agg cac ttg ctt ctg gtg ctg caa ctg      48
Met Asn Arg Gly Val Pro Phe Arg His Leu Leu Leu Val Leu Gln Leu
1               5                   10                  15 gcg ctc ctc cca gca gcc act cag gga aag aaa gtg gtg ctg ggc aaa      96
Ala Leu Leu Pro Ala Ala Thr Gln Gly Lys Lys Val Val Leu Gly Lys
                20                  25                  30 aaa ggg gat aca gtg gaa ctg acc tgt aca gct tcc cag aag aag agc     144
Lys Gly Asp Thr Val Glu Leu Thr Cys Thr Ala Ser Gln Lys Lys Ser
            35                  40                  45

-continued

| | |
|---|---|
| ata caa ttc cac tgg aaa aac tcc aac cag ata aag att ctg gga aat<br>Ile Gln Phe His Trp Lys Asn Ser Asn Gln Ile Lys Ile Leu Gly Asn<br>    50                          55                        60 | 192 |
| cag ggc tcc ttc tta act aaa ggt cca tcc aag ctg aat gat cgc gct<br>Gln Gly Ser Phe Leu Thr Lys Gly Pro Ser Lys Leu Asn Asp Arg Ala<br>65                    70                        75                        80 | 240 |
| gac tca aga aga agc ctt tgg gac caa gga aac ttc ccc ctg atc atc<br>Asp Ser Arg Arg Ser Leu Trp Asp Gln Gly Asn Phe Pro Leu Ile Ile<br>                      85                        90                        95 | 288 |
| aag aat ctt aag ata gaa gac tca gat act tac atc tgt gaa gtg gag<br>Lys Asn Leu Lys Ile Glu Asp Ser Asp Thr Tyr Ile Cys Glu Val Glu<br>            100                      105                      110 | 336 |
| gac cag aag gag gag gtg caa ttg cta gtg ttc gga ttg act gcc aac<br>Asp Gln Lys Glu Glu Val Gln Leu Leu Val Phe Gly Leu Thr Ala Asn<br>            115                      120                      125 | 384 |
| tct gac acc cac ctg ctt cag ggg cag agc ctg acc ctg acc ttg gag<br>Ser Asp Thr His Leu Leu Gln Gly Gln Ser Leu Thr Leu Thr Leu Glu<br>130                    135                      140 | 432 |
| agc ccc cct ggt agt agc ccc tca gtg caa tgt agg agt cca agg ggt<br>Ser Pro Pro Gly Ser Ser Pro Ser Val Gln Cys Arg Ser Pro Arg Gly<br>145                    150                      155                  160 | 480 |
| aaa aac ata cag ggg ggg aag acc ctc tcc gtg tct cag ctg gag ctc<br>Lys Asn Ile Gln Gly Gly Lys Thr Leu Ser Val Ser Gln Leu Glu Leu<br>                  165                      170                      175 | 528 |
| cag gat agt ggc acc tgg aca tgc act gtc ttg cag aac cag aag aag<br>Gln Asp Ser Gly Thr Trp Thr Cys Thr Val Leu Gln Asn Gln Lys Lys<br>                  180                      185                      190 | 576 |
| gtg gag ttc aaa ata gac atc gtg gtg cta gct tcg gcc gac aaa act<br>Val Glu Phe Lys Ile Asp Ile Val Val Leu Ala Ser Ala Asp Lys Thr<br>            195                      200                      205 | 624 |
| cac aca tgc cca ccg tgc cca gca cct gaa ctc ctg ggg gga ccg tca<br>His Thr Cys Pro Pro Cys Pro Ala Pro Glu Leu Leu Gly Gly Pro Ser<br>210                    215                      220 | 672 |
| gtc ttc ctc ttc ccc cca aaa ccc aag gac acc ctc atg atc tcc cgg<br>Val Phe Leu Phe Pro Pro Lys Pro Lys Asp Thr Leu Met Ile Ser Arg<br>225                    230                      235                  240 | 720 |
| acc cct gag gtc aca tgc gtg gtg gtg gac gtg agc cac gaa gac cct<br>Thr Pro Glu Val Thr Cys Val Val Val Asp Val Ser His Glu Asp Pro<br>                  245                      250                      255 | 768 |
| gag gtc aag ttc aac tgg tac gtg gac ggc gtg gag gtg cat aat gcc<br>Glu Val Lys Phe Asn Trp Tyr Val Asp Gly Val Glu Val His Asn Ala<br>            260                      265                      270 | 816 |
| aag aca aag ccg cgg gag gag cag tac aac agc acg tac cgg gtg gtc<br>Lys Thr Lys Pro Arg Glu Glu Gln Tyr Asn Ser Thr Tyr Arg Val Val<br>            275                      280                      285 | 864 |
| agc gtc ctc acc gtc ctg cac cag gac tgg ctg aat ggc aag gag tac<br>Ser Val Leu Thr Val Leu His Gln Asp Trp Leu Asn Gly Lys Glu Tyr<br>            290                      295                      300 | 912 |
| aag tgc aag gtc tcc aac aaa gcc ctc cca gcc ccc atc gag aaa acc<br>Lys Cys Lys Val Ser Asn Lys Ala Leu Pro Ala Pro Ile Glu Lys Thr<br>305                    310                      315                  320 | 960 |
| atc tcc aaa gcc aaa ggg cag ccc cga gaa cca cag gtg tac acc ctg<br>Ile Ser Lys Ala Lys Gly Gln Pro Arg Glu Pro Gln Val Tyr Thr Leu<br>                  325                      330                      335 | 1008 |
| ccc cca tcc cgg gat gag ctg acc aag aac cag gtc agc ctg acc tgc<br>Pro Pro Ser Arg Asp Glu Leu Thr Lys Asn Gln Val Ser Leu Thr Cys<br>                  340                      345                      350 | 1056 |
| ctg gtc aaa ggc ttc tat ccc agc gac atc gcc gtg gag tgg gag agc<br>Leu Val Lys Gly Phe Tyr Pro Ser Asp Ile Ala Val Glu Trp Glu Ser | 1104 |

```
                     355                 360                 365
aat ggg cag ccg gag aac aac tac aag acc acg cct ccc gtg ctg gac        1152
Asn Gly Gln Pro Glu Asn Asn Tyr Lys Thr Thr Pro Pro Val Leu Asp
        370                 375                 380 tcc gac ggc tcc ttc ttc ctc tac agc aag ctc acc gtg gac aag agc        1200
Ser Asp Gly Ser Phe Phe Leu Tyr Ser Lys Leu Thr Val Asp Lys Ser
385                 390                 395                 400 agg tgg cag cag ggg aac gtc ttc tca tgc tcc gtg atg cat gag gct        1248
Arg Trp Gln Gln Gly Asn Val Phe Ser Cys Ser Val Met His Glu Ala
                405                 410                 415 ctg cac aac cac tac acg cag aag agc cta agc ttg tct gcg ggt aaa        1296
Leu His Asn His Tyr Thr Gln Lys Ser Leu Ser Leu Ser Ala Gly Lys
            420                 425                 430 ccc acc cat gtc aat gtg tct gtt gtc atg gcg gag gtg gac ggc acc        1344
Pro Thr His Val Asn Val Ser Val Val Met Ala Glu Val Asp Gly Thr
        435                 440                 445 tgc tac tga                                                            1353
Cys Tyr
    450

<210> SEQ ID NO 6
<211> LENGTH: 450
<212> TYPE: PRT
<213> ORGANISM: Artificial Sequence
<220> FEATURE:
<223> OTHER INFORMATION: D1D2-Igatp

<400> SEQUENCE: 6

Met Asn Arg Gly Val Pro Phe Arg His Leu Leu Leu Val Leu Gln Leu
1               5                   10                  15

Ala Leu Leu Pro Ala Ala Thr Gln Gly Lys Lys Val Val Leu Gly Lys
            20                  25                  30

Lys Gly Asp Thr Val Glu Leu Thr Cys Thr Ala Ser Gln Lys Lys Ser
        35                  40                  45

Ile Gln Phe His Trp Lys Asn Ser Asn Gln Ile Lys Ile Leu Gly Asn
    50                  55                  60

Gln Gly Ser Phe Leu Thr Lys Gly Pro Ser Lys Leu Asn Asp Arg Ala
65                  70                  75                  80

Asp Ser Arg Arg Ser Leu Trp Asp Gln Gly Asn Phe Pro Leu Ile Ile
                85                  90                  95

Lys Asn Leu Lys Ile Glu Asp Ser Asp Thr Tyr Ile Cys Glu Val Glu
            100                 105                 110

Asp Gln Lys Glu Glu Val Gln Leu Leu Val Phe Gly Leu Thr Ala Asn
        115                 120                 125

Ser Asp Thr His Leu Leu Gln Gly Gln Ser Leu Thr Leu Thr Leu Glu
    130                 135                 140

Ser Pro Pro Gly Ser Ser Pro Ser Val Gln Cys Arg Ser Pro Arg Gly
145                 150                 155                 160

Lys Asn Ile Gln Gly Gly Lys Thr Leu Ser Val Ser Gln Leu Glu Leu
                165                 170                 175

Gln Asp Ser Gly Thr Trp Thr Cys Thr Val Leu Gln Asn Gln Lys Lys
            180                 185                 190

Val Glu Phe Lys Ile Asp Ile Val Val Leu Ala Ser Ala Asp Lys Thr
        195                 200                 205

His Thr Cys Pro Pro Cys Pro Ala Pro Glu Leu Leu Gly Gly Pro Ser
    210                 215                 220

Val Phe Leu Phe Pro Pro Lys Pro Lys Asp Thr Leu Met Ile Ser Arg
```

-continued

```
                    225                 230                 235                 240

Thr Pro Glu Val Thr Cys Val Val Asp Val Ser His Glu Asp Pro
                        245                 250                 255

Glu Val Lys Phe Asn Trp Tyr Val Asp Gly Val Glu Val His Asn Ala
                        260                 265                 270

Lys Thr Lys Pro Arg Glu Glu Gln Tyr Asn Ser Thr Tyr Arg Val Val
                        275                 280                 285

Ser Val Leu Thr Val Leu His Gln Asp Trp Leu Asn Gly Lys Glu Tyr
                    290                 295                 300

Lys Cys Lys Val Ser Asn Lys Ala Leu Pro Ala Pro Ile Glu Lys Thr
        305                 310                 315                 320

Ile Ser Lys Ala Lys Gly Gln Pro Arg Glu Pro Gln Val Tyr Thr Leu
                        325                 330                 335

Pro Pro Ser Arg Asp Glu Leu Thr Lys Asn Gln Val Ser Leu Thr Cys
                        340                 345                 350

Leu Val Lys Gly Phe Tyr Pro Ser Asp Ile Ala Val Glu Trp Glu Ser
                        355                 360                 365

Asn Gly Gln Pro Glu Asn Asn Tyr Lys Thr Thr Pro Pro Val Leu Asp
                    370                 375                 380

Ser Asp Gly Ser Phe Phe Leu Tyr Ser Lys Leu Thr Val Asp Lys Ser
        385                 390                 395                 400

Arg Trp Gln Gln Gly Asn Val Phe Ser Cys Ser Val Met His Glu Ala
                        405                 410                 415

Leu His Asn His Tyr Thr Gln Lys Ser Leu Ser Leu Ser Ala Gly Lys
                        420                 425                 430

Pro Thr His Val Asn Val Ser Val Val Met Ala Glu Val Asp Gly Thr
                        435                 440                 445

Cys Tyr
            450

<210> SEQ ID NO 7
<211> LENGTH: 617
<212> TYPE: DNA
<213> ORGANISM: Artificial Sequence
<220> FEATURE:
<223> OTHER INFORMATION: D1D2 domains of CD4

<400> SEQUENCE: 7
atgaaccggg gagtcccttt taggcacttg cttctggtgc tgcaactggc gctcctccca        60
gcagccactc agggaaagaa agtggtgctg ggcaaaaaag gggatacagt ggaactgacc       120
tgtacagctt cccagaagaa gagcatacaa ttccactgga aaaactccaa ccagataaag       180
attctgggaa atcagggctc cttcttaact aaaggtccat ccaagctgaa tgatcgcgct       240
gactcaagaa gaagcctttg ggaccaagga aacttccccc tgatcatcaa gaatcttaag       300
atagaagact cagatactta catctgtgaa gtggaggacc agaaggagga ggtgcaattg       360
ctagtgttcg gattgactgc caactctgac acccacctgc ttcagggggca gcctgacc       420 ctgaccttgg agagcccccc tggtagtagc ccctcagtgc aatgtaggag tccaagggggt      480 aaaaacatac aggggggggaa gaccctctcc gtgtctcagc tggagctcca ggatagtggc      540
acctggacat gcactgtctt gcagaaccag aagaaggtgg agttcaaaat agacatcgtg      600
gtgctagctt tcggccg                                                     617

<210> SEQ ID NO 8
<211> LENGTH: 744
```

<212> TYPE: DNA
<213> ORGANISM: Artificial Sequence
<220> FEATURE:
<223> OTHER INFORMATION: IgG1a tailpiece
<220> FEATURE:
<221> NAME/KEY: CDS
<222> LOCATION: (1)..(744)

<400> SEQUENCE: 8

```
tcg gcc gac aaa act cac aca tgc cca ccg tgc cca gca cct gaa ctc      48
Ser Ala Asp Lys Thr His Thr Cys Pro Pro Cys Pro Ala Pro Glu Leu
1               5                   10                  15 ctg ggg gga ccg tca gtc ttc ctc ttc ccc cca aaa ccc aag gac acc      96
Leu Gly Gly Pro Ser Val Phe Leu Phe Pro Pro Lys Pro Lys Asp Thr
            20                  25                  30 ctc atg atc tcc cgg acc cct gag gtc aca tgc gtg gtg gtg gac gtg     144
Leu Met Ile Ser Arg Thr Pro Glu Val Thr Cys Val Val Val Asp Val
        35                  40                  45 agc cac gaa gac cct gag gtc aag ttc aac tgg tac gtg gac ggc gtg     192
Ser His Glu Asp Pro Glu Val Lys Phe Asn Trp Tyr Val Asp Gly Val
    50                  55                  60 gag gtg cat aat gcc aag aca aag ccg cgg gag gag cag tac aac agc     240
Glu Val His Asn Ala Lys Thr Lys Pro Arg Glu Glu Gln Tyr Asn Ser
65                  70                  75                  80 acg tac cgg gtg gtc agc gtc ctc acc gtc ctg cac cag gac tgg ctg     288
Thr Tyr Arg Val Val Ser Val Leu Thr Val Leu His Gln Asp Trp Leu
                85                  90                  95 aat ggc aag gag tac aag tgc aag gtc tcc aac aaa gcc ctc cca gcc     336
Asn Gly Lys Glu Tyr Lys Cys Lys Val Ser Asn Lys Ala Leu Pro Ala
            100                 105                 110 ccc atc gag aaa acc atc tcc aaa gcc aaa ggg cag ccc cga gaa cca     384
Pro Ile Glu Lys Thr Ile Ser Lys Ala Lys Gly Gln Pro Arg Glu Pro
        115                 120                 125 cag gtg tac acc ctg ccc cca tcc cgg gat gag ctg acc aag aac cag     432
Gln Val Tyr Thr Leu Pro Pro Ser Arg Asp Glu Leu Thr Lys Asn Gln
    130                 135                 140 gtc agc ctg acc tgc ctg gtc aaa ggc ttc tat ccc agc gac atc gcc     480
Val Ser Leu Thr Cys Leu Val Lys Gly Phe Tyr Pro Ser Asp Ile Ala
145                 150                 155                 160 gtg gag tgg gag agc aat ggg cag ccg gag aac aac tac aag acc acg     528
Val Glu Trp Glu Ser Asn Gly Gln Pro Glu Asn Asn Tyr Lys Thr Thr
                165                 170                 175 cct ccc gtg ctg gac tcc gac ggc tcc ttc ttc ctc tac agc aag ctc     576
Pro Pro Val Leu Asp Ser Asp Gly Ser Phe Phe Leu Tyr Ser Lys Leu
            180                 185                 190 acc gtg gac aag agc agg tgg cag cag ggg aac gtc ttc tca tgc tcc     624
Thr Val Asp Lys Ser Arg Trp Gln Gln Gly Asn Val Phe Ser Cys Ser
        195                 200                 205 gtg atg cat gag gct ctg cac aac cac tac acg cag aag agc cta agc     672
Val Met His Glu Ala Leu His Asn His Tyr Thr Gln Lys Ser Leu Ser
    210                 215                 220 ttg tct gcg ggt aaa ccc acc cat gtc aat gtg tct gtt gtc atg gcg     720
Leu Ser Ala Gly Lys Pro Thr His Val Asn Val Ser Val Val Met Ala
225                 230                 235                 240 gag gtg gac ggc acc tgc tac tga                                     744
Glu Val Asp Gly Thr Cys Tyr
                245
```

<210> SEQ ID NO 9
<211> LENGTH: 247
<212> TYPE: PRT
<213> ORGANISM: Artificial Sequence

```
<220> FEATURE:
<223> OTHER INFORMATION: IgG1a tailpiece

<400> SEQUENCE: 9

Ser Ala Asp Lys Thr His Thr Cys Pro Pro Cys Pro Ala Pro Glu Leu
1               5                   10                  15

Leu Gly Gly Pro Ser Val Phe Leu Phe Pro Pro Lys Pro Lys Asp Thr
                20                  25                  30

Leu Met Ile Ser Arg Thr Pro Glu Val Thr Cys Val Val Val Asp Val
            35                  40                  45

Ser His Glu Asp Pro Glu Val Lys Phe Asn Trp Tyr Val Asp Gly Val
50                  55                  60

Glu Val His Asn Ala Lys Thr Lys Pro Arg Glu Glu Gln Tyr Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Ala Leu Pro Ala
            100                 105                 110

Pro Ile Glu Lys Thr Ile Ser Lys Ala Lys Gly Gln Pro Arg Glu Pro
        115                 120                 125

Gln Val Tyr Thr Leu Pro Pro Ser Arg Asp Glu Leu Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Lys Leu
            180                 185                 190

Thr Val Asp Lys Ser Arg Trp Gln Gln Gly Asn Val Phe Ser Cys Ser
        195                 200                 205

Val Met His Glu Ala Leu His Asn His Tyr Thr Gln Lys Ser Leu Ser
    210                 215                 220

Leu Ser Ala Gly Lys Pro Thr His Val Asn Val Ser Val Val Met Ala
225                 230                 235                 240

Glu Val Asp Gly Thr Cys Tyr
                245

<210> SEQ ID NO 10
<211> LENGTH: 1350
<212> TYPE: DNA
<213> ORGANISM: Artificial Sequence
<220> FEATURE:
<223> OTHER INFORMATION: FD1D2-Igatp
<220> FEATURE:
<221> NAME/KEY: CDS
<222> LOCATION: (1)..(1350)

<400> SEQUENCE: 10 atg aac cgg gga gtc cct ttt agg cac ttg ctt ctg gtg ctg caa ctg      48
Met Asn Arg Gly Val Pro Phe Arg His Leu Leu Leu Val Leu Gln Leu
1               5                   10                  15 gcg ctc ctc cca gca gcc act cag gga aag aaa gtg gtg ctg ggc aaa      96
Ala Leu Leu Pro Ala Ala Thr Gln Gly Lys Lys Val Val Leu Gly Lys
                20                  25                  30 aaa ggg gat aca gtg gaa ctg acc tgt aca gct tcc cag aag aag agc     144
Lys Gly Asp Thr Val Glu Leu Thr Cys Thr Ala Ser Gln Lys Lys Ser
            35                  40                  45 ata caa ttc cac tgg aaa aac tcc aac cag ata aag att ctg gga aat     192
```

```
Ile Gln Phe His Trp Lys Asn Ser Asn Gln Ile Lys Ile Leu Gly Asn
    50                  55                  60 cag ggc tcc ttc tta act aaa ggt cca tcc aag ctg aat gat cgc gct    240
Gln Gly Ser Phe Leu Thr Lys Gly Pro Ser Lys Leu Asn Asp Arg Ala
65                  70                  75                  80 gac tca aga aga agc ctt tgg gac caa gga aac ttc ccc ctg atc atc    288
Asp Ser Arg Arg Ser Leu Trp Asp Gln Gly Asn Phe Pro Leu Ile Ile
                85                  90                  95 aag aat ctt aag ata gaa gac tca gat act tac atc tgt gaa gtg gag    336
Lys Asn Leu Lys Ile Glu Asp Ser Asp Thr Tyr Ile Cys Glu Val Glu
            100                 105                 110 gac cag aag gag gag gtg caa ttg cta gtg ttc gga ttg act gcc aac    384
Asp Gln Lys Glu Glu Val Gln Leu Leu Val Phe Gly Leu Thr Ala Asn
        115                 120                 125 tct gac acc cac ctg ctt cag ggg cag agc ctg acc ctg acc ttg gag    432
Ser Asp Thr His Leu Leu Gln Gly Gln Ser Leu Thr Leu Thr Leu Glu
    130                 135                 140 agc ccc cct ggt agt agc ccc tca gtg caa tgt agg agt cca agg ggt    480
Ser Pro Pro Gly Ser Ser Pro Ser Val Gln Cys Arg Ser Pro Arg Gly
145                 150                 155                 160 aaa aac ata cag ggg ggg aag acc ctc tcc gtg tct cag ctg gag ctc    528
Lys Asn Ile Gln Gly Gly Lys Thr Leu Ser Val Ser Gln Leu Glu Leu
                165                 170                 175 cag gat agt ggc acc tgg aca tgc act gtc ttg cag aac cag aag aag    576
Gln Asp Ser Gly Thr Trp Thr Cys Thr Val Leu Gln Asn Gln Lys Lys
            180                 185                 190 gtg gag ttc aaa ata gac atc gtg gtg cta gct tcg gcc gac aaa act    624
Val Glu Phe Lys Ile Asp Ile Val Val Leu Ala Ser Ala Asp Lys Thr
        195                 200                 205 cac aca tgc cca ccg tgc cca gca cct cca gtc gcg gga ccg tca gtc    672
His Thr Cys Pro Pro Cys Pro Ala Pro Pro Val Ala Gly Pro Ser Val
    210                 215                 220 ttc ctc ttc ccc cca aaa ccc aag gac acc ctc atg atc tcc cgg acc    720
Phe Leu Phe Pro Pro Lys Pro Lys Asp Thr Leu Met Ile Ser Arg Thr
225                 230                 235                 240 cct gag gtc aca tgc gtg gtg gtg gac gtg agc cac gaa gac cct gag    768
Pro Glu Val Thr Cys Val Val Val Asp Val Ser His Glu Asp Pro Glu
                245                 250                 255 gtc aag ttc aac tgg tac gtg gac ggc gtg gag gtg cat aat gcc aag    816
Val Lys Phe Asn Trp Tyr Val Asp Gly Val Glu Val His Asn Ala Lys
            260                 265                 270 aca aag ccg cgg gag gag cag tac aac agc acg tac cgg gtg gtc agc    864
Thr Lys Pro Arg Glu Glu Gln Tyr Asn Ser Thr Tyr Arg Val Val Ser
        275                 280                 285 gtc ctc acc gtc ctg cac cag gac tgg ctg aat ggc aag gag tac aag    912
Val Leu Thr Val Leu His Gln Asp Trp Leu Asn Gly Lys Glu Tyr Lys
    290                 295                 300 tgc aag gtc tcc aac aaa gcc ctc cca gcc ccc atc gag aaa acc atc    960
Cys Lys Val Ser Asn Lys Ala Leu Pro Ala Pro Ile Glu Lys Thr Ile
305                 310                 315                 320 tcc aaa gcc aaa ggg cag ccc cga gaa cca cag gtg tac acc ctg ccc   1008
Ser Lys Ala Lys Gly Gln Pro Arg Glu Pro Gln Val Tyr Thr Leu Pro
                325                 330                 335 cca tcc cgg gat gag ctg acc aag aac cag gtc agc ctg acc tgc ctg   1056
Pro Ser Arg Asp Glu Leu Thr Lys Asn Gln Val Ser Leu Thr Cys Leu
            340                 345                 350 gtc aaa ggc ttc tat ccc agc gac atc gcc gtg gag tgg gag agc aat   1104
Val Lys Gly Phe Tyr Pro Ser Asp Ile Ala Val Glu Trp Glu Ser Asn
        355                 360                 365
```

```
ggg cag ccg gag aac aac tac aag acc acg cct ccc gtg ctg gac tcc    1152
Gly Gln Pro Glu Asn Asn Tyr Lys Thr Thr Pro Pro Val Leu Asp Ser
        370                 375                 380 gac ggc tcc ttc ttc ctc tac agc aag ctc acc gtg gac aag agc agg    1200
Asp Gly Ser Phe Phe Leu Tyr Ser Lys Leu Thr Val Asp Lys Ser Arg
385                 390                 395                 400 tgg cag cag ggg aac gtc ttc tca tgc tcc gtg atg cat gag gct ctg    1248
Trp Gln Gln Gly Asn Val Phe Ser Cys Ser Val Met His Glu Ala Leu
                405                 410                 415 cac aac cac tac acg cag aag agc cta agc ttg tct gcg ggt aaa ccc    1296
His Asn His Tyr Thr Gln Lys Ser Leu Ser Leu Ser Ala Gly Lys Pro
            420                 425                 430 acc cat gtc aat gtg tct gtt gtc atg gcg gag gtg gac ggc acc tgc    1344
Thr His Val Asn Val Ser Val Val Met Ala Glu Val Asp Gly Thr Cys
        435                 440                 445 tac tga                                                             1350
Tyr

<210> SEQ ID NO 11
<211> LENGTH: 449
<212> TYPE: PRT
<213> ORGANISM: Artificial Sequence
<220> FEATURE:
<223> OTHER INFORMATION: FD1D2-Igatp

<400> SEQUENCE: 11

Met Asn Arg Gly Val Pro Phe Arg His Leu Leu Leu Val Leu Gln Leu
1               5                   10                  15

Ala Leu Leu Pro Ala Ala Thr Gln Gly Lys Lys Val Val Leu Gly Lys
            20                  25                  30

Lys Gly Asp Thr Val Glu Leu Thr Cys Thr Ala Ser Gln Lys Lys Ser
        35                  40                  45

Ile Gln Phe His Trp Lys Asn Ser Asn Gln Ile Lys Ile Leu Gly Asn
    50                  55                  60

Gln Gly Ser Phe Leu Thr Lys Gly Pro Ser Lys Leu Asn Asp Arg Ala
65                  70                  75                  80

Asp Ser Arg Arg Ser Leu Trp Asp Gln Gly Asn Phe Pro Leu Ile Ile
                85                  90                  95

Lys Asn Leu Lys Ile Glu Asp Ser Asp Thr Tyr Ile Cys Glu Val Glu
            100                 105                 110

Asp Gln Lys Glu Glu Val Gln Leu Leu Val Phe Gly Leu Thr Ala Asn
        115                 120                 125

Ser Asp Thr His Leu Leu Gln Gly Gln Ser Leu Thr Leu Thr Leu Glu
    130                 135                 140

Ser Pro Pro Gly Ser Ser Pro Ser Val Gln Cys Arg Ser Pro Arg Gly
145                 150                 155                 160

Lys Asn Ile Gln Gly Gly Lys Thr Leu Ser Val Ser Gln Leu Glu Leu
                165                 170                 175

Gln Asp Ser Gly Thr Trp Thr Cys Thr Val Leu Gln Asn Gln Lys Lys
            180                 185                 190

Val Glu Phe Lys Ile Asp Ile Val Val Leu Ala Ser Ala Asp Lys Thr
        195                 200                 205

His Thr Cys Pro Pro Cys Pro Ala Pro Val Ala Gly Pro Ser Val
    210                 215                 220

Phe Leu Phe Pro Pro Lys Pro Lys Asp Thr Leu Met Ile Ser Arg Thr
225                 230                 235                 240

Pro Glu Val Thr Cys Val Val Val Asp Val Ser His Glu Asp Pro Glu
```

-continued

```
                    245                 250                 255
Val Lys Phe Asn Trp Tyr Val Asp Gly Val Glu Val His Asn Ala Lys
            260                 265                 270

Thr Lys Pro Arg Glu Glu Gln Tyr Asn Ser Thr Tyr Arg Val Val Ser
            275                 280                 285

Val Leu Thr Val Leu His Gln Asp Trp Leu Asn Gly Lys Glu Tyr Lys
            290                 295                 300

Cys Lys Val Ser Asn Lys Ala Leu Pro Ala Pro Ile Glu Lys Thr Ile
305                 310                 315                 320

Ser Lys Ala Lys Gly Gln Pro Arg Glu Pro Gln Val Tyr Thr Leu Pro
            325                 330                 335

Pro Ser Arg Asp Glu Leu Thr Lys Asn Gln Val Ser Leu Thr Cys Leu
            340                 345                 350

Val Lys Gly Phe Tyr Pro Ser Asp Ile Ala Val Glu Trp Glu Ser Asn
            355                 360                 365

Gly Gln Pro Glu Asn Asn Tyr Lys Thr Thr Pro Pro Val Leu Asp Ser
            370                 375                 380

Asp Gly Ser Phe Phe Leu Tyr Ser Lys Leu Thr Val Asp Lys Ser Arg
385                 390                 395                 400

Trp Gln Gln Gly Asn Val Phe Ser Cys Ser Val Met His Glu Ala Leu
                405                 410                 415

His Asn His Tyr Thr Gln Lys Ser Leu Ser Leu Ser Ala Gly Lys Pro
            420                 425                 430

Thr His Val Asn Val Ser Val Val Met Ala Glu Val Asp Gly Thr Cys
            435                 440                 445

Tyr
```

FUSION PROTEIN INCLUDING OF CD4

PRIORITY CLAIM

This is the § 371 U.S. National Stage of International Application No. PCT/US02/34393. filed Oct. 24. 2002, which was oublished in English under PCT Article 21(2). which in turn claims the benefit of U.S. Provisional Patent Application No. 60/346,231, filed Oct. 25, 2001, incorporated by reference herein in its entirety.

FIELD OF THE INVENTION

This invention relates to the field of CD4 polypeptides, specifically to CD4 fusion proteins of use in the treatment of an immunodeficiency virus infection such as a human immunodeficiency virus (HIV).

BACKGROUND OF THE INVENTION

The primary immunologic abnormality resulting from infection by HIV is the progressive depletion and functional impairment of T lymphocytes expressing the CD4 cell surface glycoprotein (Lane et al., *Ann. Rev. Immunol.* 3:477, 1985). CD4 is a non-polymorphic glycoprotein with homology to the immunoglobulin gene superfamily (Maddon et al., *Cell* 42:93, 1985). Together with the CD8 surface antigen, CD4 defines two distinct subsets of mature peripheral T cells (Reinherz et al., *Cell* 19:821, 1980), which are distinguished by their ability to interact with nominal antigen targets in the context of class I and class II major histocompatibility complex (MHC) antigens, respectively (Swain, *Proc. Natl. Acad. Sci.* 78:7101, 1981; Engleman et al., *J. Immunol.* 127:2124, 1981; Spitz et al., *J. Immunol.* 129:1563, 1982; Biddison et al., *J. Exp. Med.* 156:1065, 1982; and Wilde et al., *J. Immunol.* 131:2178, 1983). For the most part, CD4 T cells display the helper/inducer T cell phenotype (Reinherz, supra), although CD4 T cells characterized as cytotoxic/suppressor T cells have also been identified (Thomas et al., *J. Exp. Med.* 154:459, 1981; Meuer et al., *Proc. Natl. Acad. Sci. USA* 79:4395, 1982; and Krensky et al., *Proc. Natl. Acad. Sci. USA* 79:2365, 1982). The loss of CD4 helper/inducer T cell function probably underlies the profound defects in cellular and humoral immunity leading to the opportunistic infections and malignancies characteristic of the acquired immunodeficiency syndrome (AIDS) (H. Lane supra).

Studies of HIV-I infection of fractionated CD4 and CD8 T cells from normal donors and AIDS patients have revealed that depletion of CD4 T cells results from the ability of HIV-I to selectively infect, replicate in, and ultimately destroy this T lymphocyte subset (Klatzmann et al., *Science* 225:59, 1984). The possibility that CD4 itself is an essential component of the cellular receptor for HIV-I was first indicated by the observation that monoclonal antibodies directed against CD4 block HIV-I infection and syncytia induction (Dalgleish et al., *Nature* (London) 312:767,1984; McDougal et al., *J. Immunol.* 135:3151, 1985). This hypothesis has been confirmed by the demonstration that a molecular complex forms between CD4 and gp120, the major envelope glycoprotein of HIV-I (McDougal et al., *Science* 231:382, 1986); and the finding that HIV-I tropism can be conferred upon ordinarily non-permissive human cells following the stable expression of a CD4 cDNA (Maddon et al., *Cell* 47:333, 1986).

The widespread use of highly active antiretroviral therapy (HAART) has dramatically improved the clinical course for many individuals infected with HIV (Berrey, M. M. et al., *J Infect Dis* 183(10):1466, 2001). However, toxicities associated with long term HAART have put a high priority on the design and development of less toxic therapies. Among the "next generation" of antiviral inhibitors is T-20 (Wild, C. et al., *Proc Natl Acad Sci USA* 91(26):12676, 1994; Wild, et al. *Proc Natl Acad Sci USA* 89(21):10537, 1992), a relatively non-toxic peptide that disrupts viral fusion thereby protecting CD4+ lymphocytes from de novo infection. In clinical trials T-20 has been shown to reduce plasma viral load by up to two logs (Kilby, et al., *Nat Med* 4(11):1302, 1998). These results demonstrate that the entry stage of the HIV replication cycle is a viable target for the development of new antiretroviral therapies.

Viral entry is a complex biochemical event that can be subdivided into at least three stages: receptor docking, viral-cell membrane fusion, and particle uptake (D'Souza, M.P. et al., *Jama* 284(2):215, 2000). Receptor docking is a multi-step process that begins with the gp120 component of a virion spike binding to the CD4 receptor on the target cell. Conformational changes in gp120 induced by gp120-CD4 interaction promote a high affinity interaction between gp120 and either CCR5 or CXCR4 cellular co-receptors. This is followed by gp41 mediated fusion of the viral and target cell membranes. Agents designed to block gp120-CD4, gp120-CCR5/CXCR4 or gp41/cell membrane interactions are in various stages of development (D'Souza, M. P. et al., *Jama* 284(2):215, 2000). Several laboratories have constructed recombinant fusion proteins that fuse the gp120 binding domain of CD4 to immunoglobulin constant domains (Deen, K. C. et al., *Nature* 331(6151):82, 1988; Fisher, R. A. et al., *Nature* 331(6151):76, 1988; Capon, D. J. et al., *Nature* 337(6207):525, 1989; Traunecker, A. et al., *Nature* 339(6219):68, 1989; Trkola, A. et al., *J Virol* 69(11):6609, 1995). One of these, Pro-542 is currently being evaluated in clinical trials (Jacobson, J. M. et al., *J Infect Dis* 182(1):326, 2000).

The strategy underlying these CD4 based therapies, i.e. blocking the interaction between gp120 and the CD4 receptor, encompasses advantages distinct from current HAART regimens. The CD4 binding site on gp120 includes highly conserved residues; thus, agents targeting this site are unlikely to encounter resistance mutants. Additionally, such agents, by blocking de novo infection, may prevent the expansion of viral reservoirs.

Monomeric soluble CD4 (sCD4) was one of the first reagents in this group to be tested clinically (Schooley et al., *Ann Intern Med* 112(4):247, 1990). Unfortunately, sCD4 failed to demonstrate significant antiviral activity in vivo (Schooley et al., *Ann Intern Med* 112(4):247, 1990). Among the problems inherent to sCD4 was its inability to efficiently neutralize primary isolates of HIV. The differential capacity of sCD4 to neutralize tissue culture laboratory adapted (TCLA) strains versus many primary isolates is striking. In the initial report describing this difference, Ho and colleagues found that the concentrations of sCD4 required to neutralize primary isolates were up to 1000-fold higher than those required to neutralize TCLA strains (Ashkenazi et al., *Proc Natl Acad Sci USA* 88(16):7056, 1991). Surprisingly, when the affinities of sCD4 for soluble gp120s derived from TCLA and primary isolates were measured, no correlation between sCD4 neutralization and CD4:gp120 affinity was observed (Ashkenazi et al., *Proc. Natl. Acad. Sci. USA* 88(16):7056,1991; Brighty et al., *Proc. Natl. Acad. Sci. USA* 88(17):7802, 1991; Ivey-Hoyle et al., *Proc. Natl. Acad. Sci. USA* 88(2):512, 1991). However, the affinity of sCD4 for gp120 on primary virions was reduced relative to gp120 on the surface of TCLA virions (Moore et al., *J Virol* 66, 235-243, 1992). The basis for the differential interaction between sCD4 and soluble gp120 vs. virion associated gp120 is unclear.

There is an additional property of sCD4 that may, at least in part, explain its inability to neutralize primary isolates. At low concentrations sCD4 enhances the infectivity of most primary isolates (Moore et al., *Aids* 9, Suppl A:S117, 1995; Sullivan et al., *J Virol* 69(7):4413, 1995; Moore et al., *J Virol* 66(1):235, 1992; Orloff et al., *J Virol* 67(3):1461, 1993; Schutten et al., *Scand J Immunol* 41(1):18, 1995; Willey et al., *J Virol* 68(2):1029, 1994). Although these observations were made prior to the identification of the HIV fusion/coreceptors, several research groups suggested that sCD4 mediated enhancement resulted from the activation of the fusion component of virion associated spikes (Sullivan et al., *J Virol* 69(7):4413, 1995; Fu et al., *J Virol* 67(7):3818, 1993). As has since become clear, sCD4 engagement of gp120 results in conformational changes in gp120 that promote its interaction with CCR5 and thus initiates the process of virus-cell fusion (Doranz et al., *J Virol* 73(12):10346, 1999; Trkola et al., *Nature* 384(6605):184, 1996; Wu et al., *Nature* 384(6605):179, 1996; Zhang et al., *Biochemistry* 38(29):9405, 1999).

Because sCD4-mediated enhancement of virus infectivity is only observed at low concentrations of sCD4, it likely reflects a condition where virions bear a mixture of unoccupied gp120s along with sCD4-bound gp120s. Neutralization occurs only when the concentration of sCD4 reaches a threshold level where a sufficient number of spikes per virion are prevented from participating in the fusion process. The concentration required to achieve that state is likely to be extremely high for two reasons: 1) sCD4 must compete with surface bound CD4 receptors which are presented in bulk on the surface of a target cell and the effects of avidity strongly favor the receptors presented on the membrane. The lack of high avidity associated with monomeric sCD4 is a critical deficiency in the antiviral activity of this molecule, and 2) sCD4 promotes a high affinity interaction between gp120 and CCR5 (Doranz et al., *J Virol* 73(12):10346, 1999; Trkola, et al., *Nature* 384(6605):184, 1996; Wu et al., *Nature* 384(6605):179, 1996; Zhang et al., *Biochemistry* 38(29):9405, 1999). Thus, even at relatively high concentrations, sCD4 promotes interactions between the virion and the target cell membrane.

Regardless of the mechanism, it is clear that sCD4 is not the therapeutic agent of choice for treating HIV. Thus, a need remains for a CD4-based agent that can be used to study HIV infection in vitro, and is of use for treating or preventing HIV infection in vivo.

SUMMARY OF THE INVENTION

Novel recombinant polypeptides are disclosed herein that include a CD4 polypeptide ligated at its C-terminus with a portion of an immunoglobulin comprising a hinge region and a constant domain of a mammalian immunoglobulin heavy chain. The portion of the IgG is fused at its C-terminus with a polypeptide comprising a tailpiece from the C terminus of the heavy chain of an IgA antibody. Also disclosed herein are methods for using these CD4-fusion proteins.

The foregoing and other objects, features, and advantages of the invention will become more apparent from the following detailed description of several embodiments which proceeds with reference to the accompanying figures.

BRIEF DESCRIPTION OF THE FIGURES

FIG. 1A is a digital image showing gel-filtration of purified D1D2-Igαtp and FIG. 1B is a digital image showing multiple recombinant HIV gp120 proteins.

D1D2-Igαtp was purified from CHO culture supernatants and passed over a Superdex-200 gel-filtration column at a flow rate of 0.5 ml/min. Absorbance was measured at 280 nm and 0.5 ml fractions were collected. Molecular weight standards were also run under the same conditions to generate a standard curve (left inset). The void volume of this column was determined to be 7.45 mls. Peak fractions were collected and electrophoresed through a denaturing SDS-polyacrylamide gel and analyzed by western blot with an anti-CD4 polyclonal antisera (right inset). sCD4 was used as a positive control in the western blot. In FIG. 1B, a complex of D1D2Igαtp and multiple subunits of gp120 are passed over a superose-6 10/30 column at a flow rate of 0.3 ml/min. This chromatogram is compared chromatograms of D1D2Igαtp alone and gp120 alone. The presence of both D1D21gαtp and gp120 in the peak fraction is confirmed by western blot analysis (see insets).

FIG. 2 is a digital image showing a comparison of sCD4 and D1D2-Igαtp in a real-time PCR based viral entry assay. PBMCs were inoculated with HIV-1 JR-FL alone or in the presence of either sCD4 or D1D2-Igαtp. The number of virions entering cells within 6 hrs. post infection was determined using a real-time PCR based viral entry assay in which early-LTR reverse transcripts were enumerated. A standard curve was generated from genomic DNA obtained from an ACH-2 cell line carrying a single integrated HIV-1 genome. FIG. 2A shows a direct comparison of sCD4 vs. D1D2-Igαtp. FIG. 2B is a further titration of D1D2-Igαtp. The correlation coefficient for these two experiments was 0.993 and 0.998 respectively with slopes of −3.209 and −3.356 respectively. These results are representative of at least three independent experiments using different donor PBMCs.

FIG. 3 is a digital image of propagation of HIV-1 from infected patient PBMCs in the presence of sCD4 versus D1D2-Igαtp. PBMCs derived from HIV+ patients were co-cultured with uninfected donor PBMCs and treated in parallel with either sCD4 or D1D2-Igαtp. Viral replication was measured by p24 antigen ELISA in culture supernatants. Three different patient samples were analyzed. Levels of p24 were measured on the day of peak replication in cultures containing various concentrations (3 nM, 6 nM or 12 nM) of either sCD4 or D1D2-Igαtp (FIGS. 3B, 3C, and 3D). A time course for donor 1, treated with 6 nM sCD4 or D1D2-Igαtp is shown in panel a.

FIG. 4 are graphs of data obtained from acute infection of uninfected PBMCs with HIV-1 Bal and a primary viral isolate in the presence of sCD4, D1D2-Igαtp, and mAb 17b. Activated PBMCs from uninfected donors were acutely infected with HIV-1 Bal (FIG. 4A) or a primary isolate (FIG. 4B) in the presence of sCD4, D1D2-Igαtp, mAb 17b and combinations of sCD4 and 17b or D1D2-Igαtp and 17b. p24 values were measured every two days and values from the peak day of replication are reported. These results are representative of at least three independent experiments using different donor PBMCs.

FIG. 5 are digital images showing biosensor analysis of the stoichiometry of gp120 monomers bound per D1D2-Igαtp. FIG. 5A is a sensorgram overlay of increasing concentrations of NL-4-3 gp120 binding to D1D2-Igαtp. D1D2-Igαtp 1 was bound to protein A, previously immobilized to a density of 735 RU, starting at point (a) for a total of 2 min, ending at point (b). After a 5 minute washout period to allow this surface to stabilize, NL-4-3 gp120 was injected starting at point (c) at the concentrations shown in the inset, and ending at point (d). The amount of protein bound, in response units (RU), was determined at points (c) and (d) for D1D2-Igαtp and gp120, respectively, in each cycle. In FIG. 5B the total mass of each protein bound was determined as described in materials and methods and are presented as the ratio of the number of gp120 monomers bound per D1D2-Igαtp.

FIG. 6 are digital images that show the relative rates of dissociation of gp120 from sCD4 and D1D2-Igαtp. In FIG. 6A Soluble CD4 (sCD4) or D1D2-Igαtp was attached to a CM5 sensor surface either by direct amine coupling (sCD4, 400-500 RU), or indirectly using protein A (D1D2-Igαtp, 200-250 RU). The indicated gp120 s (100 nM each) were then passed over the surfaces at 25 μl/min for 2 minutes at which point running buffer in the absence of gp120 was passed over the surfaces to allow dissociation of bound proteins. As the association phase of each ligand-analyte pair showed little variation in binding rates, only the dissociation phase of each sensorgram is shown. Each curve was normalized to account for differences in total response in the individual experiments. In FIG. 6B gp120 was attached to the CM5 sensor chip by direct amine coupling, and JR-FL gp120 was passed over the chip at increasing concentrations.

FIG. 7 are digital images that show hydrodynamic and thermodynamic studies of the size-distributions of D1D2-Igαtp. Sedimentation coefficient distributions c(s) of the peak D1D2-Igαtp fraction (solid line) and trailing fraction (dashed line) are represented. The arrows indicate the estimated range of sedimentation coefficients for the different oligomers, which results in hydrodynamic radius values of 11.9-12.9 nm for a 0pentamer (with 14-15 S), 12.7-13.5 nm for a hexamer (16-17 S), 12.6-13.3 nm for a heptamer (19-20 S), and 12.5-13.1 nm for an octamer (22-23 S). The top inset shows sedimentation equilibrium data of D1D2-Igαtp at 3,000 rpm (squares), 5,000 rpm (circles), and 7,500 rpm (triangles), This resulted in 1,240 kDa (or 8.8 monomer units) at 3,000 rpm to 954 kDa (6.8 units) at 5,000 rpm, and 810 kDa (5.8 units) at 7,500 rpm. The bottom inset shows the hydrodynamic radius distribution calculated from dynamic light scattering data, for the peak fraction (solid line) and trailing fraction (dashed line). The contribution to the scattering intensity increases with size of the molecules, and therefore overemphasizes the abundance of larger species in the peak fraction.

FIG. 8 is a graph showing the neutralization of four primary isolates of HIV-1 by D1D2-Igαtp. Four minimally passaged primary isolates of HIV-1 were preincubated with D1D2-Igαtp and then added to a culture of activated PBMCs. Cultures were maintained in standard culture media and neutralization assays were in a standard manner. reverse transcriptase present in the viral supernatant was measured for each day. Neutralization is reported as the percent inhibition relative to virus without any inhibitor, and reported just prior to the day of peak replication.

FIG. 9 is a bar graph of viral entry assay in which D1D2-Igαtp was added one or two hours after exposure of PBMC to HIV-1. Viral entry assays were carried out as described in FIG. 2, however, D1D2-Igαtp was added after virus was allowed to attach to cells.

FIG. 10 is set of line graphs showing the binding of D1D2-Igαtp or FD1D2-Igαtp to cell expressing CD16 (FcγRIII) or CD32 (FcγRII). The results from competition experiments using a labeled anti CD16 or anti CD32 antibody as a competitor are shown. Results are expressed as the inhibition of binding of the antibody to either CD16 or CD32. FIG. 10A shows the binding to CD16 obtained in the presence of 1-1000 nM of competitor. D1D2-Igαtp efficiently competes for binding to CD16, while FD1D2-Igαtp competes less efficiently. Antibody 2G12 (negative control, a human IgG$_1$) did not compete for binding to CD16. The % CD16 mean channel fluorescence (mcf) was calculated as follows:

$$\% \ CD16 \ mcf = \frac{(CD16 \text{ with inhibitor } mcf\text{-background}) - (CD16mcf\text{-backgroud})}{(CD16 \ mcf\text{-background})} \times 100$$

FIG. 10B shows the binding to CD32 obtained in the presence of 1-1000 nM of competitor (2G12, a human IgG$_1$). D1D2-Igαtp efficiently competes for binding to CD32, while FD1D2-Igαtp competes less efficiently. Antibody 2G12, (negative control, a human IgG$_1$), did not compete for binding to CD32. The % CD32 mcf was calculated as follows:

$$\% \ CD32 \ mcf = \frac{(CD32 \text{ with inhibitor } mcf\text{-background}) - (CD32mcf\text{-backgroud})}{(CD32 \ mcf\text{-background})} \times 100$$

FIG. 11 is a series of plots showing the induction of a calcium flux by D1D2-Igαtp or FD1D2-Igαtp (mutant F) in natural killer (NK) cells after the cells were cultured in vitro for 14 days. Each point shown represents a single cell. The negative control (SHAM, FIG. 11A) did not exhibit any calcium influx, while application of different concentrations of D1D2-Igαtp (FIGS. 11B-F, 120 nM, 60 nM, 30 nm, 15 nM, and 7.5 nM, respectively) elicited a calcium influx. Mutant F application did not induce a calcium influx (FIG. 11GK, 120 nM, 60 nM, 30 nM, 15 nM, and 7.5 nM, respectively), indicated that this molecule does not activate natural killer cells.

FIG. 12 is a set of plots from Fluorescence Activated Cell Sorting Analyses demonstrating that natural killer cells in the presence of D1D2-Igαtp mediate antibody dependent cell mediated cytotoxicity. Natural killer (NK) cells and HIV-infected CEM.NRK target cells were incubated in the presence of D1D2-Igαtp or in media alone. Cells were subsequently labeled with propidium iodide, which measures cell viability. In the presence of D1D2-Igαtp, 45% of the HIV-1 infected cells were killed (FIG. 13A), whereas without application of D1D2-Igαtp, only 15% of the cells were killed (FIG. 13B). The same number of uninfected CEM-.NRK cells survived in the presence of D1D2-Igαtp (FIG. 13D) as compared to uninfected CEM.NRK cells incubated in the absence of antibody.

Figure 2:
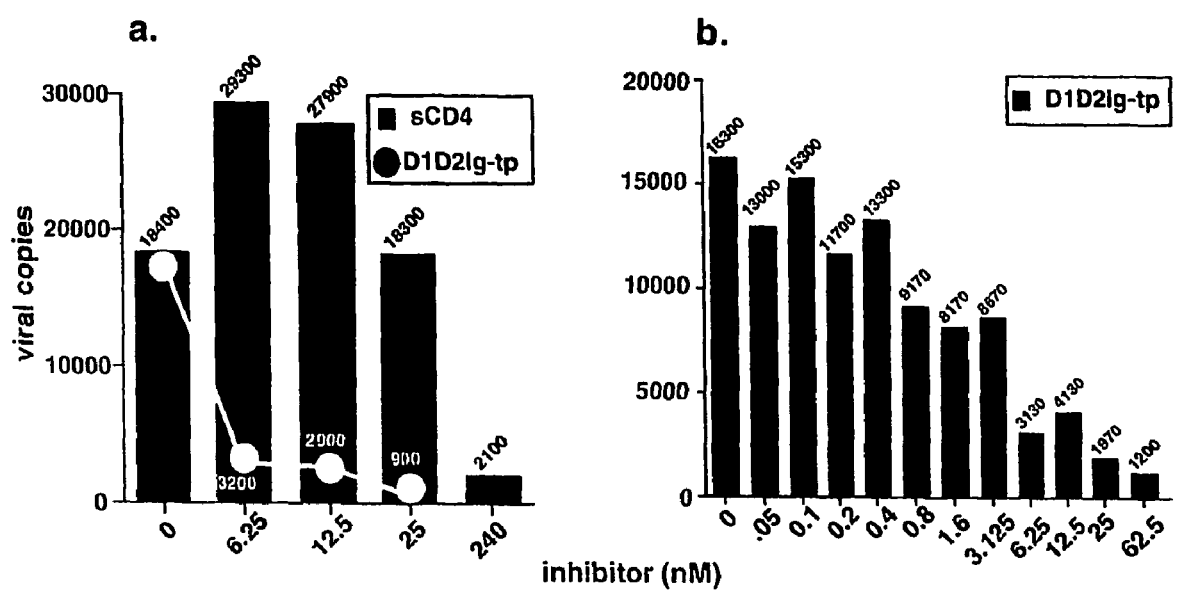

In FD1D2-Igαtp, amino acid residues 218-221 are replaced by the corresponding residues of an $IgG_2$. Thus, 218-Glu Leu Leu Gly Gly Pro-221

(corresponding to residues 233-238 in an intact immunoglobulin molecule, using the numbering system of Kabat et al., "Sequences of proteins of immunological interest." U.S. Department of Health and Human Services, National Institutes of Health, Bethesda, Md., 1991) is replaced by 218-Pro Val—Ala Gly Pro-221.

It should be noted that replacement of one or more residues of Asn 297, Asp 265, P329, Asp 270, Ala 327, Ser 239, Lys 338 (using the numbering system of Kabat et al., "Sequences of proteins of immunological interest." U.S. Department of Health and Human Services, National Institutes of Health, Bethesda, Md., 1991) (see Shields et al., J. Biol Chem. 276(9): 6591-604, 2001) with other amino acids, will induce a similar effect.

DETAILED DESCRIPTION OF SEVERAL EMBODIMENTS

The following definitions and methods are provided to better define the present invention and to guide those of ordinary skill in the art in the practice of the present invention. It must be noted that as used herein and in the appended claims, the singular forms "a", "an", and "the" include plural referents unless the context clearly dictates otherwise. Thus, for example, reference to "a cell" includes a plurality of such cells and reference to "the antibody" includes reference to one or more antibodies and equivalents thereof known to those skilled in the art, and so forth.

Unless defined otherwise, all technical and scientific terms used herein have the same meaning as commonly understood to one of ordinary skill in the art to which this invention belongs.

Term

Alpha tailpiece (αtp): The tailpiece located at the C-terminus of the heavy chain of an IgA antibody. In one embodiment, this peptide is 18 amino acids in length and is derived from a human IgA molecule. In one embodiment, an alpha tailpiece is PTHVNVSVVMAEVDGTCY (SEQ ID NO:1). However, if desired the peptide may be modified to remove the glycosylation site by changing 1 or 2 amino acids at residues 5-7 (NVS). For example, the asparagine (N) at position 5 can be changed to a glutamine (Q). Alternatively, the serine (S) at position 7 can be changed to an alanine (A). Additionally, a few of the amino acids residues of the IgA constant region may also be included, such as about four amino acids of the IgA constant region. Suitable IgA molecules, having an alpha tailpiece of use include, but are not limited to, human IgA1, human IgA2, rabbit IgA, and mouse IgA. This peptide is linked, either directly or indirectly to a constant domain of an immunoglobulin, such as a fragment including the CH2 and CH3 domains.

Animal: A living multicellular vertebrate organism, a category which includes, for example, mammals and birds. A "mammal" includes both human and non-human mammals. Similarly, the term "subject" includes both human and veterinary subjects.

Antibody: Immunoglobulin molecules and immunologically active portions of immunoglobulin molecules, i.e., molecules that contain an antigen binding site which specifically binds (immunoreacts with) an antigen.

A naturally occurring antibody (e.g., IgG) includes four polypeptide chains, two heavy (H) chains and two light (L) chains inter-connected by disulfide bonds. However, it has been shown that the antigen-binding function of an antibody can be performed by fragments of a naturally occurring antibody. Thus, these antigen-binding fragments are also intended to be designated by the term "antibody". Examples of binding fragments encompassed within the term antibody include (i) an Fab fragment consisting of the VL, VH, CL and CH1 domains; (ii) an Fd fragment consisting of the VH and CH1 domains; (iii) an Fv fragment consisting of the VL and VH domains of a single arm of an antibody, (iv) a dAb fragment (Ward et al., Nature 341:544-546, 1989) which consists of a VH domain; (v) an isolated complimentarily determining region (CDR); and (vi) an $F(ab')_2$ fragment, a bivalent fragment comprising two Fab fragments linked by a disulfide bridge at the hinge region.

Antigen Presenting Cell (APC): Cells that present antigen to the immune system. There are three general classes of antigen presenting cells (APCs): macrophages, dendritic cells, and B cells, although neutrophils can also present antigens. Processing and surface presentation of antigen by APCs can be thought of as a first step in the normal immune response. The antigen can be any antigen, including but not limited to an antigen of a bacterial, virus, fungus, or any other infectious organism.

"Antigen presentation" is the set of events whereby cells fragment antigens into peptides, and then present these peptides in association with products of the major histocompatibility complex, (MHC). The MHC is a region of highly polymorphic genes whose products are expressed on the surfaces of a variety of cells. T cells recognize foreign antigens bound to only one specific class I or class II MHC molecule. Activated or "stimulated" antigen presenting cells are uniquely capable of processing and presenting antigens to naive T cells. The patterns of antigen association with either a class I or class II MHC molecule determines which T cells are stimulated.

Avidity: The overall strength of interaction between two molecules, such as an antigen and an antibody. Avidity depends on both the affinity and the valency of interactions. Therefore, the avidity of a pentameric IgM antibody, with ten antigen binding sites, for a multivalent antigen may be much greater than the avidity of a dimeric IgG molecule for the same antigen.

Binding or stable binding: An oligonucleotide binds or stably binds to a target nucleic acid if a sufficient amount of the oligonucleotide forms base pairs or is hybridized to its target nucleic acid, to permit detection of that binding. Binding can be detected by either physical or functional properties of the target:oligonucleotide complex. Binding between a target and an oligonucleotide can be detected by any procedure known to one skilled in the art, including both functional and physical binding assays. Binding can be detected functionally by determining whether binding has an observable effect upon a biosynthetic process such as expression of a gene, DNA replication, transcription, translation and the like.

Physical methods of detecting the binding of complementary strands of DNA or RNA are well known in the art, and include such methods as DNase I or chemical footprinting, gel shift and affinity cleavage assays, Northern blotting, dot blotting and light absorption detection procedures. For example, one method that is widely used, because it is so simple and reliable, involves observing a change in light absorption of a solution containing an oligonucleotide (or an analog) and a target nucleic acid at 220 to 300 nm as the temperature is slowly increased. If the oligonucleotide or analog has bound to its target, there is a sudden increase in absorption at a characteristic temperature as the oligonucleotide (or analog) and target disassociate from each other, or melt.

The binding between an oligomer and its target nucleic acid is frequently characterized by the temperature ($T_m$) at which 50% of the oligomer is melted from its target. A higher ($T_m$) means a stronger or more stable complex relative to a complex with a lower ($T_m$).

CD4: Cluster of differentiation factor 4 polypeptide, a T-cell surface protein that mediates interaction with the MHC class II molecule. CD4 also serves as the primary receptor site for HIV on T-cells during HIV infection.

The known sequence of the CD4 precursor has a hydrophobic signal peptide, an extracelluar region of approximately 370 amino acids, a highly hydrophobic stretch with significant identify to the membrane-spanning domain of the class II MHC beta chain, and a highly charged intracellular sequence of 40 resides (Maddon, *Cell* 42:93, 1985).

The term "CD4" includes polypeptide molecules that are derived from CD4 include fragments of CD4, generated either by chemical (e.g., enzymatic) digestion or genetic engineering means. Such a fragment may be one or more entire CD4 protein domains. The extracellular domain of CD4 consists of four contiguous immunoglobulin-like regions (D1, D2, D3, and D4, see Sakihama et al., *Proc. Natl. Acad. Sci.* 92:6444, 1995; U.S. Pat. No. 6,117,655), and amino acids 1 to 183 have been shown to be involved in gp120 binding. For instance, a binding molecule or binding domain derived from CD4 would comprise a sufficient portion of the CD4 protein to mediate specific and functional interaction between the binding fragment and a native or viral binding site of CD4. One such binding fragment includes both the D1 and D2 extracellular domains of CD4 (D1D2 is also a fragment of soluble CD4 or sCD4 which is comprised of D1 D2 D3 and D4), although smaller fragments may also provide specific and functional CD4-like binding. The gp120-binding site has been mapped to D1 of CD4.

CD4 polypeptides also include "CD4-derived molecules" which encompasses analogs (non-protein organic molecules), derivatives (chemically functionalized protein molecules obtained starting with the disclosed protein sequences) or mimetics (three-dimensionally similar chemicals) of the native CD4 structure, as well as proteins sequence variants or genetic alleles, that maintain the ability to functionally bind to a target molecule.

cDNA (complementary DNA): A piece of DNA lacking internal, non-coding segments (introns) and transcriptional regulatory sequences. cDNA can also contain untranslated regions (UTRs) that are responsible for translational control in the corresponding RNA molecule. cDNA is synthesized in the laboratory by reverse transcription from messenger RNA extracted from cells.

Constant domain of an immunoglobulin heavy chain or Fc: There is a region of about 110 amino acids in the N-terminal portion of the heavy-chain which always differs in amino acid sequence from one Ig heavy-chain preparation to another. The remainder of the heavy-chain sequence shows little if any amino acid-sequence difference, and are called the constant or "C" regions. These C-region sequences can be grouped into 5 classes of immunoglobulin heavy-chains named: gamma, mu, alpha, delta, and epsilon. The immunoglobulins from which these heavy chains are obtained were are named: IgG, IgM, IgA, IgD, and IgE, respectively. The heavy chains of IgG, IgA, and IgD are about 50,000 MW, while the heavy chains of IgM and IgE are about 65,000 MW. For an individual immunoglobulin molecule there are at least two heavy-chains of identical sequence on a given molecule (analogous to the constant region of light chains on a given molecule). In addition, the pattern of 110 amino-acid-in length segments was retained in each heavy chain. Thus, IgG heavy chain has about 110 amino acids in the N-terminal portion, then a 110 amino acid segment designated CH1 (constant heavy 1), then a 110 amino acid segment named CH2, then finally, a 110 amino acid segment named CH3. IgG, IgA and IgE each include 3 constant domains named CH1, CH2, and CH3, while IgM includes CH1, CH2, CH3, and a additional CH4 region. As the amino acid sequence of the different heavy-chain classes differ significantly within a species they can be readily distinguished from one another. A "hinge" region of an immunoglobulin is an amino acid sequence that connects CH2 and CH3 to each other. In one embodiment, an immunoglobulin Fc includes the CH2 and CH3 regions, and can also include the hinge region.

Conservative substitutions: Modifications of a polypeptide that involve the substitution of one or more amino acids for amino acids having similar biochemical properties that do not result in change or loss of a biological or biochemical function of the polypeptide. These "conservative substitutions" are likely to have minimal impact on the activity of the resultant protein. Table 1 shows amino acids that may be substituted for an original amino acid in a protein, and which are regarded as conservative substitutions.

TABLE 1

| Original Residue | Conservative Substitutions |
| --- | --- |
| Ala | ser |
| Arg | lys |
| Asn | gln; his |
| Asp | glu |
| Cys | ser |
| Gln | asn |
| Glu | asp |
| Gly | pro |
| His | asn; gln |
| Ile | leu; val |
| Leu | ile; val |
| Lys | arg; gln; glu |
| Met | leu; ile |
| Phe | met; leu; tyr |
| Ser | thr |
| Thr | ser |
| Trp | tyr |
| Tyr | trp; phe |
| Val | ile; leu |

In one embodiment, one or more conservative changes, or up to ten conservative changes, can be made in a polypeptide without changing a biochemical function of the polypeptide. For example, one or more conservative changes can be made in a CD4 D1D2 polypeptide without changing its ability to bind to gp120. More substantial changes in a biochemical function or other protein features may be obtained by selecting amino acid substitutions that are less conservative than those listed in Table 2. Such changes include, for example, changing residues that differ more significantly in their effect on maintaining polypeptide backbone structure (e.g., sheet or helical conformation) near the substitution, charge or hydrophobicity of the molecule at the target site, or bulk of a specific side chain. The following substitutions are generally expected to produce the greatest changes in protein properties: (a) a hydrophilic residue (e.g., seryl or threonyl) is substituted for (or by) a hydrophobic residue (e.g., leucyl, isoleucyl, phenylalanyl, valyl or alanyl); (b) a cysteine or proline is substituted for (or by) any other residue; (c) a residue having an electropositive side chain (e.g., lysyl, arginyl, or histadyl) is substituted for (or by) an electronegative residue (e.g., glutamyl or aspartyl); or (d) a residue having a bulky side chain (e.g., phenylalanine) is substituted for (or by) one lacking a side chain (e.g., glycine).

DNA: Deoxyribonucleic acid. DNA is a long chain polymer which comprises the genetic material of most living organisms (some viruses have genes comprising ribonucleic acid (RNA)). The repeating units in DNA polymers are four different nucleotides, each of which comprises one of the four bases, adenine, guanine, cytosine and thymine bound to a deoxyribose sugar to which a phosphate group is attached. Triplets of nucleotides (referred to as codons) code for each amino acid in a polypeptide. The term codon is also used for the corresponding (and complementary) sequences of three nucleotides in the mRNA into which the DNA sequence is transcribed.

Deletion: The removal of a sequence of DNA, the regions on either side being joined together.

Encode: A polynucleotide is said to "encode" a polypeptide if, in its native state or when manipulated by methods well known to those skilled in the art, it can be transcribed and/or translated to produce the mRNA for and/or the polypeptide or a fragment thereof. The anti-sense strand is the complement of such a nucleic acid, and the encoding sequence can be deduced therefrom.

Functional fragments and variants of a polypeptide: Includes those fragments and variants that maintain one or more functions of the parent polypeptide. It is recognized that the gene or cDNA encoding a polypeptide can be considerably mutated without materially altering one or more the polypeptide's functions. First, the genetic code is well known to be degenerate, and thus different codons encode the same amino acids. Second, even where an amino acid substitution is introduced, the mutation can be conservative and have no material impact on the essential functions of a protein. See Stryer, Biochemistry 3rd Ed., 1988. Third, part of a polypeptide chain can be deleted without impairing or eliminating all of its functions. Fourth, insertions or additions can be made in the polypeptide chain, for example, adding epitope tags—without impairing or eliminating its functions (Ausubel et al., J. Immunol. 159:2502, 1997). Other modifications that can be made without materially impairing one or more functions of a polypeptide include, for example, in vivo or in vitro chemical and biochemical modifications or which incorporate unusual amino acids. Such modifications include, for example, acetylation, carboxylation, phosphorylation, glycosylation, ubiquination, labeling, e.g., with radionuclides, and various enzymatic modifications, as will be readily appreciated by those well skilled in the art. A variety of methods for labeling polypeptides and of substituents or labels useful for such purposes are well known in the art, and include radioactive isotopes such as $^{32}P$, ligands which bind to labeled antiligands (e.g., antibodies), fluorophores, chemiluminescent agents, enzymes, and antiligands. Functional fragments and variants can be of varying length. For example, some fragments have at least 10, 25, 50, 75, 100, or 200 amino acid residues.

A functional fragment or variant of CD4 is defined herein as a polypeptide which binds to gp120. It includes any polypeptide six or more amino acid residues in length which is capable of binding gp120, or binds an MCH class II molecule.

Gp120: The envelope protein from Human Immunodeficiency Virus (HIV). The envelope protein is initially synthesized as a longer precursor protein of 845-870 amino acids in size, designated gp160. Gp160 forms a homotrimer and undergoes glycosylation within the Golgi apparatus. It is then cleaved by a cellular protease into gp120 and gp41. Gp41 contains a transmembrane domain and remains in a trimeric configuration; it interacts with gp120 in a non-covalent manner. Gp120 contains most of the external, surface-exposed, domains of the envelope glycoprotein complex, and it is gp120 which binds both to the cellular CD4 receptor and to the cellular chemokine receptors (e.g., CCR5)

The gp120 core has a unique molecular structure, that comprises two domains: an "inner" domain (which faces gp41) and an "outer" domain (which is mostly exposed on the surface of the oligomeric envelope glycoprotein complex). The two gp120 domains are separated by a "bridging sheet" that is not part of either domain. Binding to CD4 causes a conformational change in gp120 which exposes the bridging sheet and may move the inner and outer domains relative to each other. The CD4-binding pocket within gp120 comprises a number of residues which interact directly with Phe43 of CD4. The most important of these are Glu370, Trp427 and Asp368 (the latter residue also forms a salt bridge with Arg59 of CD4). These three residues are conserved in all primate lentiviruses.

Immunoglobulins: A class of proteins found in plasma and other body fluids that exhibits antibody activity and binds with other molecules with a high degree of specificity; divided into five classes (IgM, IgG, IgA, IgD, and IgE) on the basis of structure and biological activity. Immunoglobulins and certain variants thereof are known and many have been prepared in recombinant cell culture (e.g., see U.S. Pat. Nos. 4,745,055; 4,444,487; WO 88/03565; EP 256,654; EP 120,694; EP 125, 023; Faoulkner et al., Nature 298:286, 1982; Morrison, J. Immunol. 123:793, 1979; Morrison et al., Ann Rev. Immunol. 2:239, 1984). A chimeric immunoglobulin includes residues primarily from a first class of immunoglobulin, with amino acids substituted by the corresponding residues of a second class of immunoglobulin. In one specific, non-limiting example, a chimeric $IgG_1$ includes corresponding residues from an $IgG_2$. In several non-limiting examples, at least one, about one to about twenty, about one to about ten, about one to about five, or about four residues are substituted.

A native (naturally occurring) immunoglobulin is each is made up of four polypeptide chains. There are two long chains, called the "heavy" or "H" chains which weigh between 50 and 75 kilodaltons and two short chains called "light" or "L" chains weighing in at 25 kilodaltons. They are linked together by what are called disulfide bonds to form a "Y" shape molecule. Each heavy chain and light chain can be divided into a variable region and a constant region. An Fc region includes the constant regions of the heavy and the light chains, but not the variable regions. Fc receptors are those receptors that specifically bind an Fc region of an immunoglobulin. These receptors include, but are not limited to, FcαRII, FcαRIII, and FcRN.

Isolated: An "isolated" biological component (such as a nucleic acid molecule, protein or organelle) has been substantially separated or purified away from other biological components in the cell of the organism in which the component naturally occurs, i.e., other chromosomal and extra-chromosomal DNA and RNA, proteins and organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids.

Lymphocytes: A type of white blood cell that is involved in the immune defenses of the body. There are two main types of lymphocytes: B-cells and T-cells.

Mu tailpiece (μtp): The tailpiece located at the C-terminus of the heavy chain of an IgM antibody. In one embodiment, this peptide is 18 amino acids in length and is derived from an IgM molecule.

Natural Killer Cell: A large granular lymphocyte capable of killing a tumor or microbial cell without prior exposure to the target cell and without having it presented with or marked by a histocompatibility antigen.

Nucleotide: "Nucleotide" includes, but is not limited to, a monomer that includes a base linked to a sugar, such as a pyrimidine, purine or synthetic analogs thereof, or a base linked to an amino acid, as in a peptide nucleic acid (PNA). A nucleotide is one monomer in a polynucleotide. A nucleotide sequence refers to the sequence of bases in a polynucleotide.

Oligonucleotide: An oligonucleotide is a plurality of joined nucleotides joined by native phosphodiester bonds, between about 6 and about 300 nucleotides in length. An oligonucleotide analog refers to moieties that function similarly to oligonucleotides but have non-naturally occurring portions. For example, oligonucleotide analogs can contain non-naturally occurring portions, such as altered sugar moieties or inter-sugar linkages, such as a phosphorothioate oligodeoxynucleotide. Functional analogs of naturally occurring polynucleotides can bind to RNA or DNA, and include peptide nucleic acid (PNA) molecules.

Particular oligonucleotides and oligonucleotide analogs can include linear sequences up to about 200 nucleotides in length, for example a sequence (such as DNA or RNA) that is at least 6 bases, for example at least 8, 10, 15, 20, 25, 30, 35, 40, 45, 50, 100 or even 200 bases long, or from about 6 to about 50 bases, for example about 10-25 bases, such as 12, 15 or 20 bases.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

Open reading frame: A series of nucleotide triplets (codons) coding for amino acids without any internal termination codons. These sequences are usually translatable into a peptide.

Pharmaceutical agent: A chemical compound or composition capable of inducing a desired therapeutic or prophylactic effect when properly administered to a subject or a cell. "Incubating" includes a sufficient amount of time for a drug to interact with a cell. "Contacting" includes incubating a drug in solid or in liquid form with a cell. An "anti-viral agent" or "anti-viral drug" is an agent that specifically inhibits a virus from replicating or infecting cells. Similarly, an "anti-retroviral agent" is an agent that specifically inhibits a retrovirus from replicating or infecting cells.

A "therapeutically effective amount" is a quantity of a chemical composition or an anti-viral agent sufficient to achieve a desired effect in a subject being treated. For instance, this can be the amount necessary to inhibit viral replication or to measurably alter outward symptoms of the viral infection, such as increase of T cell counts in the case of an HIV infection. In general, this amount will be sufficient to measurably inhibit virus (e.g., HIV) replication or infectivity. When administered to a subject, a dosage will generally be used that will achieve target tissue concentrations (for example, in lymphocytes) that has been shown to achieve in vitro inhibition of viral replication.

Probes and primers: Nucleic acid probes and primers can be readily prepared based on a nucleic acid sequence. A probe comprises an isolated nucleic acid attached to a detectable label or reporter molecule. Typical labels include radioactive isotopes, enzyme substrates, co-factors, ligands, chemiluminescent or fluorescent agents, haptens, and enzymes. Methods for labeling and guidance in the choice of labels appropriate for various purposes are discussed, e.g., in Sambrook et al. (In *Molecular Cloning: A Laboratory manual*, CSHL, New York, 1989) and Ausubel et al. (In *Current Protocols in Molecular Biology*, Greene Publ. Assoc. and Wiley-Intersciences, 1992).

Primers are short nucleic acid molecules, preferably DNA oligonucleotides 10 nucleotides or more in length. More preferably, longer DNA oligonucleotides can be about 15, 17, 20, or 23 nucleotides or more in length. Primers can be annealed to a complementary target DNA strand by nucleic acid hybridization to form a hybrid between the primer and the target DNA strand, and then the primer extended along the target DNA strand by a DNA polymerase enzyme. Primer pairs can be used for amplification of a nucleic acid sequence, e.g., by the polymerase chain reaction (PCR) or other nucleic-acid amplification methods known in the art.

Methods for preparing and using probes and primers are described, for example, in Sambrook et al. (In *Molecular Cloning: A Laboratory Manual*, CSHL, New York, 1989), Ausubel et al. (In *Current Protocols in Molecular Biology*, Greene Publ. Assoc. and Wiley-Intersciences, 1998), and Innis et al. (*PCR Protocols, A Guide to Methods and Applications*, Academic Press, Inc., San Diego, Calif., 1990). PCR primer pairs can be derived from a known sequence, for example, by using computer programs intended for that purpose such as Primer (Version 0.5, © 1991, Whitehead Institute for Biomedical Research, Cambridge, Mass.). One of ordinary skill in the art will appreciate that the specificity of a particular probe or primer increases with its length. Thus, for example, a primer comprising 30 consecutive nucleotides of the CD4 encoding nucleotide will anneal to a target sequence, such as another nucleic acid encoding CD4, with a higher specificity than a corresponding primer of only 15 nucleotides. Thus, in order to obtain greater specificity, probes and primers can be selected that comprise at least 17, 20, 23, 25, 30, 35, 40, 45, 50 or more consecutive nucleotides of cardiac nucleotide sequence of interest.

Protein: A biological molecule expressed by a gene and comprised of amino acids.

Purified: The term "purified" does not require absolute purity; rather, it is intended as a relative term. Thus, for example, a purified protein preparation is one in which the protein referred to is more pure than the protein in its natural environment within a cell.

Recombinant: A recombinant nucleic acid is one that has a sequence that is not naturally occurring or has a sequence that is made by an artificial combination of two otherwise separated segments of sequence. This artificial combination can be accomplished by chemical synthesis or, more commonly, by the artificial manipulation of isolated segments of nucleic acids, e.g., by genetic engineering techniques.

Sequence identity: The similarity between two nucleic acid sequences, or two amino acid sequences, is expressed in terms of the similarity between the sequences, otherwise referred to as sequence identity. Sequence identity is frequently measured in terms of percentage identity (or similarity or homology); the higher the percentage, the more similar the two sequences are. Homologs or orthologs of the human CD4 protein, and the corresponding cDNA sequence, will possess a relatively high degree of sequence identity when aligned using standard methods. This homology will be more significant when the orthologous proteins or cDNAs are derived from species which are more closely related (e.g., human and chimpanzee sequences), compared to species more distantly related (e.g., human and murine sequences).

Methods of alignment of sequences for comparison are well known in the art. Various programs and alignment algorithms are described in: Smith & Waterman, *Adv. Appl. Math.* 2:482,1981; Needleman & Wunsch, *J. Mol. Biol.* 48:443, 1970; Pearson & Lipman, *Proc. Natl. Acad. Sci. USA* 85:2444, 1988; Higgins & Sharp, *Gene,* 73:237-244, 1988); Higgins & Sharp, *CABIOS* 5:151-153, 1989; Corpet et al., *Nuc. Acids Res.* 16:10881-90, 1988; Huang et al., *Computer Appls. in the Biosciences* 8:155-65, 1992; and Pearson et al., *Meth. Mol. Bio.* 24:307-31, 1994. Altschul et al., *J. Mol. Biol.* 215:403-410, 1990, presents a detailed consideration of sequence alignment methods and homology calculations.

The NCBI Basic Local Alignment Search Tool (BLAST) (Altschul et al., *J. Mol. Biol.* 215:403-410, 1990) is available from several sources, including the National Center for Biotechnology Information (NCBI, Bethesda, Md.) and on the Internet, for use in connection with the sequence analysis programs blastp, blastn, blastx, tblastn and tblastx. It can be accessed at the NCBI website, together with a description of how to determine sequence identity using this program.

Homologs of the disclosed human CD4 protein typically possess at least 60% sequence identity counted over full-length alignment with the amino acid sequence of human CD4 using the NCBI Blast 2.0, gapped blastp set to default parameters. For comparisons of amino acid sequences of greater than about 30 amino acids, the Blast 2 sequences function is employed using the default BLOSUM62 matrix set to default parameters, (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). Proteins with even greater similarity to the reference sequence will show increasing percentage identities when assessed by this method, such as at least 70%, at least 75%, at least 80%, at least 90%, at least 95%, at least 98%, or at least 99% sequence identity. When less than the entire sequence is being compared for sequence identity, homologs will typically possess at least 75% sequence identity over short windows of 10-20 amino acids, and can possess sequence identities of at least 85% or at least 90% or 95% depending on their similarity to the reference sequence. Methods for determining sequence identity over such short windows are described in the NCBI website. These sequence identity ranges are provided for guidance only; it is entirely possible that strongly significant homologs could be obtained that fall outside of the ranges provided.

An alternative indication that two nucleic acid molecules are closely related is that the two molecules hybridize to each other under stringent conditions. Stringent conditions are sequence-dependent and are different under different environmental parameters. Generally, stringent conditions are selected to be about 5° C. to 20° C. lower than the thermal melting point (Tm) for the specific sequence at a defined ionic strength and pH. The $T_m$ is the temperature (under defined ionic strength and pH) at which 50% of the target sequence remains hybridized to a perfectly matched probe or complementary strand. Conditions for nucleic acid hybridization and calculation of stringencies can be found in Sambrook et al. (1989) *Molecular Cloning: A Laboratory Manual*, CSHL, New York and Tijssen (1993) *Laboratory Techniques in Biochemistry and Molecular Biology—Hybridization with Nucleic Acid Probes* Part I, Chapter 2, Elsevier, N.Y. Nucleic acid molecules that hybridize under stringent conditions to a given CD4 sequence will typically under wash conditions of 2×SSC at 50° C.

Nucleic acid sequences that do not show a high degree of identity can nevertheless encode similar amino acid sequences, due to the degeneracy of the genetic code. It is understood that changes in nucleic acid sequence can be made using this degeneracy to produce multiple nucleic acid molecules that all encode substantially the same protein.

T Cell: A white blood cell critical to the immune response. T cells include, but are not limited to, $CD4^+$ T cells and $CD8^+$ T cells. A $CD4^+$ T lymphocyte is an immune cell that carries a marker on its surface known as "cluster of differentiation 4" (CD4). These cells, also known as helper T cells, help orchestrate the immune response, including antibody responses as well as killer T cell responses. $CD8^+$ T cells carry the "cluster of differentiation 8" (CD8) marker. In one embodiment, a CD8 T cells is a cytotoxic T lymphocytes. In another embodiment, a CD8 cell is a suppressor T cell.

Treatment: Refers to both prophylactic inhibition of initial infection, and therapeutic interventions to alter the natural course of an untreated disease process, such as infection with a virus (e.g., HIV infection).

Transformed: A transformed cell is a cell into which has been introduced a nucleic acid molecule by molecular biology techniques. As used herein, the term transformation encompasses all techniques by which a nucleic acid molecule might be introduced into such a cell, including transfection with viral vectors, transformation with plasmid vectors, and introduction of DNA by electroporation, lipofection, and particle gun acceleration.

Vector: A nucleic acid molecule as introduced into a host cell, thereby producing a transformed host cell. Recombinant DNA vectors are vectors having recombinant DNA. A vector can include nucleic acid sequences that permit it to replicate in a host cell, such as an origin of replication. A vector can also include one or more selectable marker genes and other genetic elements known in the art. Viral vectors are recombinant DNA vectors having at least some nucleic acid sequences derived from one or more viruses.

Virus: Microscopic infectious organism that reproduces inside living cells. A virus consists essentially of a core of a single nucleic acid surrounded by a protein coat, and has the ability to replicate only inside a living cell. "Viral replication" is the production of additional virus by the occurrence of at least one viral life cycle. A virus may subvert the host cells' normal functions, causing the cell to behave in a manner determined by the virus. For example, a viral infection may result in a cell producing a cytokine, or responding to a cytokine, when the uninfected cell does not normally do so.

"Retroviruses" are RNA viruses wherein the viral genome is RNA. When a host cell is infected with a retrovirus, the genomic RNA is reverse transcribed into a DNA intermediate which is integrated very efficiently into the chromosomal DNA of infected cells. The integrated DNA intermediate is referred to as a provirus. The term "lentivirus" is used in its conventional sense to describe a genus of viruses containing reverse transcriptase. The lentiviruses include the "immunodeficiency viruses" which include human immunodeficiency virus (HIV) type 1 and type 2 (HIV-1 and HIV-2), simian immunodeficiency virus (SIV), and feline immunodeficiency virus (FIV).

HIV is a retrovirus that causes immunosuppression in humans (HIV disease), and leads to a disease complex known as the acquired immunodeficiency syndrome (AIDS). "HIV disease" refers to a well-recognized constellation of signs and symptoms (including the development of opportunistic infections) in persons who are infected by an HIV virus, as determined by antibody or western blot studies. Laboratory findings associated with this disease are a progressive decline in T-helper cells.

The treatment of HIV disease has been significantly advanced by the recognition that combining different drugs with specific activities against different biochemical functions of the virus can help reduce the rapid development of drug resistant viruses that were seen in response to single drug treatment. In addition, discontinuation of existing therapies results in a rapid rebound of viral replication, indicating the lack of complete HIV eradication by the drugs. There is therefore a continuing need for the development of new anti-retroviral drugs that act specifically at different steps of the viral infection and replication cycle.

Fusion Proteins Including CD4, an Immunoglobulin Constant Region, and an Alpha Tailpiece Disclosed herein are recombinant polypeptides comprising a CD4 polypeptide ligated at its C-terminus with a portion of an immunoglobulin comprising a hinge region and a constant domain of a mammalian immunoglobulin heavy chain. The portion of the immunoglobulin is ligated at its C-terminus with a polypeptide comprising a tailpiece from the C terminus of the heavy chain of an IgA antibody (αtp) or a tailpiece from a C terminus of the heavy chain of an IgM antibody.

The term ligated encompasses the use of a linker between one polypeptide component and another. Thus, in a specific, non-limiting example, a linker is included between a constant domain of the mammalian immunoglobulin heavy chain and the tailpiece, (e.g., αtp). In another specific, non-limiting example, a linker is included between the CD4 polypeptide and the immunoglobulin constant domain. A linker includes any short chain polypeptide chain of between one and 35 amino acids, including but not limited to, a glycine repeat. One specific, non-limiting example of a linker is between one and ten glycine residues, such as about two to about five glycine resides, or about three glycine residues. Another example of a linker is gly-pro-pro linker or multimers of gly-pro-pro. The CD4 polypeptide can include the D1 and D2 regions of CD4 (e.g., see U.S. Pat. No. 5,126,433). The boundary domains for the CD4 regions are, respectively, about 100-109 (D1), about 175-184 (D2), about 289-298 (D3), and about 360-369 (D4), based on the precursor CD4 amino acid in which the initiating met is found at −25 (see U.S. Pat. No. 6,117,655). Soluble CD4 molecules of use are also described in U.S. Pat. No. 5,422,274. In one embodiment, the CD4 molecule is any CD4 polypeptide, or functional fragment thereof, that binds gp120. In one, specific, non-limiting example, the CD4 polypeptide is the D1 and D2 domains of the human CD4. In another specific, non-limiting example, the CD4 polypeptide is a variant or functional fragment of the D1 and D2 domains of human CD4, chimpanzee CD4 or rhesus macaque CD4. In another embodiment, the CD4 polypeptide includes one or more modifications of the D1 and/or D2 domains such that the affinity of the CD4 for gp120 is altered. In one specific, non-limiting example, the affinity of the CD4 polypeptide for gp120 is increased.

In one embodiment, the C-terminus of the CD4 polypeptide is ligated to the N-terminus of a constant region of an immunoglobulin in place of the variable region. As discussed above, the CD4 molecule can be directly ligated to the constant region (without the use of a linker), or a linker can be included between the CD4 and the constant region.

When the constant domain (Fc) is a heavy chain constant domain, all of the domains of constant region can be included. Typically, the fusion includes at least the hinge region and one CH domain. In one embodiment, the fusion includes the hinge region and the CH2 and CH3 domain of the constant region of an immunoglublin heavy chain.

The heavy chain constant region used in the construction of the CD4 fusion protein can be from any antibody subclass, except IgA. Thus, the constant region may be derived from an immunoglobulin of the IgG, IgD, IgE or IgM.subclass. When the Fc fragment is from an IgG antibody, any of the human isotypes can be utilized (e.g., $IgG_1$, $IgG_2$, $IgG_3$, $IgG_4$). In specific, non-limiting example, the constant domain is from an $IgG_2$. Further, the parental IgG antibody or the isolated domain of the constant region can be mutated to reduce binding to complement or Ig-Fc receptors (e.g., see Duncan et al., Nature 332:563, 1988; Duncan and Winter, Nature 332:738, 1988; Alegre et al., J. Immunol. 148:3461, 1992; Tao et al., J. Exp. Med. 178:661, 1993; Xu et al., J. Bio. Chem. 269:3469, 1994). In one embodiment, the constant region is from an IgM, and includes the hinge region, CH2 and CH3, but does not include the naturally occurring 18 amino acids (µtail piece, but includes the αtp). In another embodiment, the Fc portion is from IgG, IgD, IgE, but not IgM, and the µtp is included.

In another embodiment, a chimeric constant domain is utilized that includes a domain of one isotype fused with another domain from a different isotype. One specific, non-liming example of a chimeric constant domain is the hinge of $IgG_2$ included in an $IgG_1$ constant domain. In another embodiment, residues involved in the binding of an $IgG_1$ to a Fc region are replaced by residues from an $IgG_2$ that are involved in the binding to an Fc region. One of skill in the art can readily identify residues involved in Fc binding (see Kabat et al., supra, 1991; Shields et al., J. Biol Chem. 276(9): 6591-604, 2001). In addition, as the amino acids involved in contact between immunoglobulins and Fc receptors (including, but not limited to, FcRN, FcγRII, and FcγRIII) can be identified, these specific residues can be substituted, using substitutions (such as in the formation of chimeras, or mutagenesis strategies). In one specific, non-limiting example, in the CH2CH3 region of an intact $IgG_1$ the following sequence 233-Glu Leu Leu Gly Gly Pro-238*

(*using the numbering system provided in Kabat et. al, supra, 1991)

is replaced by residues from the corresponding regions of an immunoglobulin of a different class, such as, but not limited to, IgG$_2$, IgA, IgM, or IgD. In one specific, non-limiting example, corresponding residues from an intact IgG$_2$ are used, such as, but not limited to:

233-Pro Val—Ala Gly Pro-238, wherein "—" indicates the absence of a residue.

In another specific non-limiting example, one or more residues of IgG$_1$ Fc binding domain are replaced from by a corresponding residue of an immunoglobulin from a different class. In yet another specific, non-limiting example, one or more residues of IgG$_1$ Fc binding domain are replaced by any other amino acid, or are deleted. These residues, include, but are not limited to (Asn 297, Asp 265, Pro 329, Asp 270, Ala 327, Ser 239, Lys 338) any other amino acid molecule (see Kabat, et al, supra, 1991 for a description of the numbering of amino acid molecules in an immunoglobulin).

The CH2 or CH3 domain can also be modified by conventional techniques to contain a restriction enzyme site for convenient cloning. In one embodiment, the modified CD4 includes the D1 and D2 domains of CD4, the hinge, CH2 and CH3 domains of an IgG$_2$, wherein the CH3 domain is modified to contain a restriction enzyme site for convenient cloning of the tailpiece of the heavy chain of an IgA antibody.

The tailpiece the heavy chain of an IgA antibody is a peptide located at the C terminus of the naturally-occurring antibody. In one embodiment, this peptide is about eighteen residues in length. One peptide of use is PTHVNVSVVMAEDGTCY (SEQ ID NO:1). This peptide may be modified to remove the glycosylation site by changing one or more of the amino acid at residues 5-7 (NVS, see above). this peptide is 18 amino acids in length and is derived from a human IgA molecule. In one embodiment, an alpha tailpiece is PTHVNVSVVMAEVDGTCY (SEQ ID NO:1). However, if desired the peptide may be modified to remove the glycosylation site by changing 1 or 2 amino acids at residues 5-7 (NVS). For example, the asparagine (N) at position 5 can be changed to a glutamine (Q). Alternatively, the serine (S) at position 7 can be changed to an alanine (A). Additionally, a few of the amino acids residues of the IgA constant region may also be included, such as about four amino acids of the IgA constant region.

As discussed above, the fusion protein may include a linker sequence located between the constant domain of the immunoglobulin and the αtp.

Nucleic Acid Sequences and their Expression

The polypeptides disclosed herein be made using techniques known to one of skill in the art (e.g., see WO 97/47732, herein incorporated by reference in its entirety). Briefly, each chain of the polypeptide is constructed or selected. In one embodiment, the polypeptides disclosed herein are produced using recombinant technology. In one embodiment, nucleic acid sequences encoding the polypeptide of interest are produced and are expressed in vitro in a host cell. Variants of the nucleic acids include variations due the degeneracy of the genetic code. Further, the polynucleotide sequences may be modified by adding tags that can be readily quantified, where desirable. Probes or primers can be used to assay the presence of the nucleic acid sequences in the host cell, or selectable markers can be included to facilitate detection of the nucleic acid sequences in a host cell.

The nucleic acid sequence encoding the fusion protein can also be inserted into other cloning vehicles, such as other plasmids, bacteriophages, cosmids, animal viruses and yeast artificial chromosomes (YACs) (Burke et al., *Science* 236: 806-812, 1987). A suitable expression system can be chosen to express the nucleic acid sequences in a eurkaryotic system. Numerous types of appropriate expression vectors and host cell systems are known in the art, including, but not limited to systems for expression in mammalian and yeast cells. Suitable host cells or cell lines for transfection include human 293 cells, chines hamster ovary cells (CHO), murine L cells, monkey cells (e.g., COS-1 or COS-7), or murine 3T3 cells (e.g., see U.S. Pat. No. 4,419,449, or in Gething and Sambrook, *Nature* 293:620, 1981, or in Kaufman et al., *Mol. Cell. Biol.* 5:1750, 1975).

For expression in mammalian cells, the nucleic acid sequence encoding the CD4 fusion protein can be ligated to heterologous promoters, such as the simian virus (SV) 40 promoter in the pSV2 vector (Mulligan and Berg, *Proc. Natl. Acad. Sci. USA* 78:2072-2076, 1981), and introduced into cells, such as monkey COS-1 cells (Gluzman, *Cell* 23:175-182, 1981), to achieve transient or long-term expression. The stable integration of the chimeric gene construct can be maintained in mammalian cells by biochemical selection, such as neomycin (Southern and Berg, *J. Mol. Appl. Genet.* 1:327-341, 1982) and mycophenolic acid (Mulligan and Berg, *Proc. Natl. Acad Sci. USA* 78:2072-2076, 1981).

DNA sequences can be manipulated with standard procedures such as restriction enzyme digestion, fill-in with DNA polymerase, deletion by exonuclease, extension by terminal deoxynucleotide transferase, ligation of synthetic or cloned DNA sequences, site-directed sequence-alteration via single-stranded bacteriophage intermediate or with the use of specific oligonucleotides in combination with PCR.

The nucleic acid sequence can be introduced into eukaryotic expression vectors by conventional techniques. These vectors are designed to permit the transcription of the nucleic acid in eukaryotic cells by providing regulatory sequences that initiate and enhance the transcription of the cDNA and ensure its proper splicing and polyadenylation. Vectors containing the promoter and enhancer regions of the SV40 or long terminal repeat (LTR) of the Rous Sarcoma virus and polyadenylation and splicing signal from SV40 are readily available (Mulligan et al., *Proc. Natl. Acad. Sci. USA* 78:1078-2076, 1981; Gorman et al., *Proc. Natl. Acad. Sci USA* 78:6777-6781, 1982). The level of expression of the cDNA can be manipulated with this type of vector, either by using promoters that have different activities (for example, the baculovirus pAC373 can express cDNAs at high levels in *S.frugiperda* cells (Summers and Smith, A *Manual of Methods for Baculovirus Vectors and Insect Cell Culture Procedures*, Texas Agricultural Experiment Station Bulletin No. 1555, 1987; Ausubel et al., Chapter 16 in *Short Protocols in Molecular Biology*, 1999) or by using vectors that contain promoters amenable to modulation, for example, the glucocorticoid-responsive promoter from the mouse mammary tumor virus (Lee et al., *Nature* 294:228, 1982).

In addition, some vectors contain selectable markers such as the gpt (Mulligan and Berg, *Proc. Natl. Acad. Sci. USA* 78:2072-2076, 1981) or neo (Southern and Berg, *J. Mol. Appl. Genet.* 1:327-341, 1982) bacterial genes. These selectable markers permit selection of transfected cells that exhibit stable, long-term expression of the vectors (and therefore the cDNA). The vectors can be maintained in the cells as episomal, freely replicating entities by using regulatory elements of viruses such as papilloma (Sarver et al., *Mol. Cell Biol.* 1:486, 1981) or Epstein-Barr (Sugden et al., *Mol.*

*Cell Biol.* 5:410, 1985). Alternatively, one can also produce cell lines that have integrated the vector into genomic DNA. Both of these types of cell lines produce the CD4 fusion protein on a continuous basis. One can also produce cell lines that have amplified the number of copies of the vector (and therefore of the cDNA as well) to create cell lines that can produce high levels of the gene product (Alt et al., *J. Biol. Chem.* 253:1357, 1978).

The transfer of DNA into eukaryotic, in particular human or other mammalian cells, is now a conventional technique. The vectors are introduced into the recipient cells as pure DNA (transfection) by, for example, precipitation with calcium phosphate (Graham and vander Eb, *Virology* 52:466, 1973) or strontium phosphate (Brash et al., *Mol. Cell Biol.* 7:2013, 1987), electroporation (Neumann et al., *EMBO J* 1:841, 1982), lipofection (Felgner et al., *Proc. Natl. Acad. Sci. USA* 84:7413, 1987), DEAE dextran (McCuthan et al., *J. Natl. Cancer Inst.* 41:351, 1968), microinjection (Mueller et al., *Cell* 15:579, 1978), protoplast fusion (Schafner, *Proc. Natl. Acad. Sci. USA* 77:2163-2167, 1980), or pellet guns (Klein et al., *Nature* 327:70, 1987). Alternatively, the cDNA, or fragments thereof, can be introduced by infection with virus vectors. Systems are developed that use, for example, retroviruses (Bernstein et al., *Gen. Engr'g* 7:235, 1985), adenoviruses (Ahmad et al., *J. Virol.* 57:267, 1986), or Herpes virus (Spaete et al., *Cell* 30:295, 1982). Sequences encoding a CD4 fusion protein can also be delivered to target cells in vitro via non-infectious systems, for instance liposomes. Thus disclosed herein are recombinant vectors that include nucleic acid encoding the CD4 fusion proteins, and host cell transfected with the vectors.

In another embodiment, transgenic animals are used to produce the CD4 fusion proteins disclosed herein. One of skill in the art can readily produce transgenic mammals, including, but not limited to transgenic non-human primates, transgenic sheep, transgenic cows, and transgenic mice containing a nucleic acid encoding the CD4 fusion proteins. Similarly transgenic plants can readily be produced that include nucleic acid sequences encoding the disclosed CD4 fusion proteins.

Pharmaceutical Compositions

The present invention includes a treatment for an infection with immunodeficiency virus, in a subject such as an animal, for example a monkey or a human. Treatment includes both inhibition of initial infection, and therapeutic interventions to alter the natural course of an untreated HIV infection. The method includes administering the CD4 fusion protein, or a combination of the CD4 fusion protein, and optionally one or more other pharmaceutical agents, to the subject in a pharmaceutically compatible carrier and in an amount effective to inhibit the development or progression of viral disease. In one embodiment, the pharmaceutical agent is an anti-viral agent. In a specific, non-limiting example, the anti-viral agent is an anti-retroviral agent, and the virus is HIV. In other, specific, non-limiting examples, the anti-viral agent is an anti-retroviral agent, and the virus is SIV or FIV. Although the treatment can be used prophylactically in any patient in a demographic group at significant risk for such diseases, subjects can also be selected using more specific criteria, such as a definitive diagnosis of the condition.

The vehicle in which the drug is delivered can include pharmaceutically acceptable compositions of the drugs, using methods well known to those with skill in the art. Any of the common carriers, such as sterile saline or glucose solution, can be utilized with the drugs provided by the invention. Routes of administration include but are not limited to oral and parenteral routes, such as intravenous (iv), intraperitoneal (ip), subcutaneous, rectal, topical, ophthalmic, nasal, and transdermal. In one embodiment, a topical preparation is utilized. Suitable formulations for topical mircobicide preparations are known in the art.

The drugs may be administered intravenously in any conventional medium for intravenous injection, such as an aqueous saline medium, or in blood plasma medium. The medium may also contain conventional pharmaceutical adjunct materials such as, for example, pharmaceutically acceptable salts to adjust the osmotic pressure, lipid carriers such as cyclodextrins, proteins such as serum albumin, hydrophilic agents such as methyl cellulose, detergents, buffers, preservatives and the like. A more complete explanation of parenteral pharmaceutical carriers can be found in Remington: The *Science and Practice of Pharmacy* ($19^{th}$ Edition, 1995) in chapter 95.

Embodiments of other pharmaceutical compositions can be prepared with conventional pharmaceutically acceptable carriers, adjuvants and counterions as would be known to those of skill in the art. The compositions are preferably in the form of a unit dose in solid, semi-solid and liquid dosage forms such as tablets, pills, powders, liquid solutions or suspensions.

The compounds of the present invention are ideally administered as soon as possible after potential or actual exposure to the virus. Alternatively the agent may be administered, for example, following an occupational injury, such as a needle stick injury or involuntary exposure to HIV infected blood. In another example, the agent can be administered following high risk sexual activity. Alternatively, once HIV infection has been confirmed by clinical observation or laboratory tests, a therapeutically effective amount of the CD4 fusion protein is administered. In one embodiment, the dose can be given by frequent bolus administration.

Therapeutically effective doses of the compounds of the present invention can be determined by one of skill in the art, with a goal of achieving tissue concentrations that are at least as high as the $IC_{50}$ of each fusion protein. Low toxicity of the compound makes it possible to administer high doses. An example of a dosage range is 0.01 to 100 mg/kg body weight subcutaneously in single or divided doses. Another example of a dosage range is 0.1 to 100 mg/kg body weight subcutaneously in single or divided doses. For oral administration, the compositions are, for example, provided in the form of a tablet containing 1.0 to 1000 mg of the active ingredient, particularly 1, 5, 10, 15, 20, 25, 50, 100, 200, 400, 500, 600, and 1000 mg of the active ingredient for the symptomatic adjustment of the dosage to the subject being treated.

The specific dose level and frequency of dosage for any particular subject may be varied and will depend upon a variety of factors, including the activity of the specific compound, the metabolic stability and length of action of that compound, the age, body weight, general health, sex, diet, mode and time of administration, rate of excretion, drug combination, and severity of the condition of the host undergoing therapy.

Nucleotide based pharmaceuticals may be only inefficiently delivered through ingestion. However, pill-based forms of pharmaceutical nucleotides may be administered subcutaneously, particularly if formulated in a slow-release composition. Slow-release formulations may be produced by combining the target protein with a biocompatible matrix, such as cholesterol. Another possible method of administering the pharmaceuticals is through the use of mini osmotic pumps. As stated above a biocompatible carrier would also be used in conjunction with this method of delivery.

CD4 fusion proteins can be also be delivered to cells in the form of a nucleic acid that encodes the CD4 fusion protein, and is subsequently transcribed by the host cell. When using this method to deliver a CD4 fusion protein, a vector can be designed that contains a sequence encoding the CD4 fusion protein. The vector can also include a promoter to drive the expression of the CD4 fusion protein. In one embodiment, the vector is a viral vector. The viral vector including nucleic acid encoding the CD4 fusion protein can be delivered as a virion or in conjunction with a liposome. Several techniques for delivering therapeutic nucleic acid sequences are well know in the art for example, Blau and Springer, *New Engl. J. Med.* 333:1204-1207, 1995, and Hanania et al., *Amer. J. Med.* 99:537-552, 1995.

A nucleic acid molecule can also be delivered directly to the cell via liposome mediated delivery. The liposome fuses with or are enveloped by the cells. Thus, a nucleic acid molecule encoding the CD4 fusion protein is delivered intracellularly. Liposomes may be prepared with purified proteins or peptides that mediate fusion of membranes. Furthermore, the liposome may contain targeting molecules such as antibodies that allow the liposome to selectively bind to specific cells within the body. Potential lipids that can be used in the formation of liposomes include neutral lipids, such as cholesterol, phosphatidyl serine, phosphatidyl glycerol, and the like. For preparing the liposomes, the procedure described by Kato et al., *J. Biol. Chem.* 266:3361, 1991, may be used.

The pharmaceutical compositions of the present invention that include nucleic acids molecules may be administered by any means that achieve their intended purpose (see above). For therapeutic use, an infected cell is exposed to the polynucleotide in an effective concentration or effective amount. Exposing a cell includes administering the molecule to any subject, such as a mammal (e.g., a human).

The pharmaceutical compositions can be used in the treatment of a variety of diseases caused by infection with viruses. Examples of such diseases include, but are not limited to, HIV-1 and HIV-2 infections. Other examples of such diseases include, but are not limited to SIV and FIV.

Combination Therapy

The present methods also include combinations of the CD4 fusion proteins disclosed herein with one or more antiviral drugs useful in the treatment of viral disease. For example, the CD4 fusion proteins disclosed herein may be administered, whether before or after exposure to the virus, in combination with effective doses of other anti-virals, immunomodulators, anti-infectives, or vaccines. The term "administration" refers to both concurrent and sequential administration of the active agents.

In one embodiment, a combination of CD4 fusion protein with one or more agents useful in the treatment of a viral disease is provided. In one specific, non-limiting example, the viral disease is a retroviral disease, such as an HIV-1-induced, an HIV-2-induced, a SIV-induced, or a FIV induced disease.

Example of antivirals that can be used in the method of the invention are: AL-721 (from Ethigen of Los Angeles, Calif.), recombinant human interferon beta (from Triton Biosciences of Alameda, Calif.), Acemannan (from Carrington Labs of Irving, Tex.), gangiclovir (from Syntex of Palo Alto, Calif.), didehydrodeoxythymidine or d4T (from Bristol-Myers-Squibb), EL10 (from Elan Corp. of Gainesville, Ga.), dideoxycytidine or ddC (from Hoffman-LaRoche), Novapren (from Novaferon Labs, Inc. of Akron, Ohio), zidovudine or AZT (from Burroughs Wellcome), ribavirin (from Viratek of Costa Mesa, Calif.), alpha interferon and acyclovir (from Burroughs Wellcome), Indinavir (from Merck & Co.), 3TC (from Glaxo Wellcome), Ritonavir (from Abbott), Saquinavir (from Hoffmann-LaRoche), and others.

Examples of immuno-modulators are AS-101 (Wyeth-Ayerst Labs.), bropirimine (Upjohn), gamma interferon (Genentech), GM-CSF (Genetics Institute), IL-2 (Cetus or Hoffman-LaRoche), human immune globulin (Cutter Biological), IMREG (from Imreg of New Orleans, La.), SK&F106528, TNF (Genentech), and soluble TNF receptors (Immunex).

Examples of some anti-infectives used include clindamycin with primaquine (from Upjohn, for the treatment of pneumocystis pneumonia), fluconazlone (from Pfizer for the treatment of cryptococcal meningitis or candidiasis), nystatin, pentamidine, trimethaprim-sulfamethoxazole, and many others.

"Highly active anti-retroviral therapy" or "HAART" refers to a combination of drugs which, when administered in combination, inhibits a retrovirus from replicating or infecting cells better than any of the drugs individually. In one embodiment, the retrovirus is a human immunodeficiency virus. In one embodiment, the highly active anti-retroviral therapy includes the administration of 3'axido-3-deoxy-thymidine (AZT) in combination with other agents. Examples of agents that can be used in combination in HAART for a human immunodeficiency virus are nucleoside analog reverse transcriptase inhibitor drugs (NA), non-nucleoside analog reverse transcriptase inhibitor drugs (NNRTI), and protease inhibitor drugs (PI). One specific, non-limiting example of HAART used to suppress an HIV infection is a combination of indinavir and efavirenz, an experimental non-nucleoside reverse transcriptase inhibitor (NNRTI).

In one embodiment, HAART is a combination of three drugs used for the treatment of an HIV infection, such as the drugs shown in Table 2 below. Examples of three drug HAART for the treatment of an HIV infection include 1 protease inhibitor from column A plus 2 nucleoside analogs from column B in Table 2. In addition, ritonavir and saquinavir can be used in combination with 1 or 2 nucleoside analogs.

TABLE 2

| Column A | Column B |
| --- | --- |
| indinavir (Crixivan) | AZT/ddI |
| nelfinavir (Viracept) | d4T/ddI |
| ritonavir (Norvir) | AZT/ddC |
| saquinavir (Fortovase) | AZT/3TC |
| ritonavir/saquinavir | d4T/3TC |

In addition, other 3- and 4-drug combinations can reduce HIV to very low levels for sustained periods. The combination therapies are not limited to the above examples, but include any effective combination of agents for the treatment of HIV disease (including treatment of AIDS).

Induction of an Immune Response and Vaccines

The CD4 fusion proteins disclosed herein can be complexed to an HIV-1 envelope protein and used to inhibit or prevent of HIV infection or inhibit disease progression. The CD4 fusion proteins can be used to induce an immune response, such as, but not limited to, an immune response against an HIV infected cell. In one specific, non-limiting example, the immune response is activation of natural killer cells.

In one embodiment, a D1D2-Igαtp (see below) is complexed to an envelope protein of HIV1 and administered to a subject. Methods for forming a complex of CD4 with an envelope protein of HIV (e.g., gp120) are known (e.g., see WO18433A2). In one embodiment, a CD4 fusion polypeptide is covalently linked to gp120. One specific, non-limiting example of a method for producing covalent linkage is chemical cross-lining. In another embodiment, a CD4 fusion polypeptide is non-covalently linked to gp120. A specific, non-limiting example of a method for producing non-covalent linkage is incubating the CD4 fusion polypeptide with gp120 for a sufficient amount of time for a complex to form.

The conjugate is included in a vaccine formulation in an amount per unit dose sufficient to evoke an active immune response to the human immunodeficiency virus in the subject to be treated. The immune response can be any level of protection from subsequent exposure to the virus which is of some benefit in a population of subjects, whether in the form of decreased mortality, decreased morbidity, improved T cell numbers or function, or the reduction of any other detrimental effect of the disease (e.g., reduction in HIV protease activity, see U.S. Pat. No. 5,171,662), regardless of whether the protection is partial or complete.

The vaccine can be administered to the subject by any suitable means. Examples are by oral administration, intramuscular injection, subcutaneous injection, intravenous injection, intraperitoneal injection, eye drop or by nasal spray. Vaccine formulations can optionally contain one or more adjuvants. Any suitable adjuvant can be used, including chemical and polypeptide immunostimulants which enhance the immune system's response to antigens. Specific, non-limiting examples of adjuvants are aluminum hydroxide, aluminum phosphate, plant and animal oils. These adjuvants are administered with the vaccine conjugate in an amount sufficient to enhance the immune response of the subject to the vaccine conjugate. In addition, the vaccine formulations can optionally contain one or more stabilizers. Any suitable stabilizer can be used, including, but not limited to carbohydrates such as sorbitol, manitol, starch, sucrose, dextrin, or glucose; proteins such as albumin or casein; and buffers such as alkaline metal phosphate and the like. Methods for the preparation of vaccines are known in the art (see, for example, U.S. Pat. No. 6,136,319 and U.S. Pat. No. 6,113,962).

The dose of the vaccine may vary according to factors such as the disease state, age, sex, immune status, and weight of the individual, and the ability to elicit a desired response in the individual. Dosage regime may be adjusted to provide the optimum therapeutic response. For example, several divided doses may be administered daily or the dose may be proportionally reduced as indicated by the therapeutic situation. The dose of the vaccine may also be varied to provide an optimum preventative dose response depending upon the circumstances (see WO 9703A1). Thus, a method for preventing an HIV infection, by administering a CD4 fusion polypeptide, is provided herein.

In another embodiment, a DNA vaccine is utilized (e.g., see *Nat. Med.*, 5(5):526-34, 1999). Thus, a method is provided for treating a viral infection, such as an HIV infection, by providing a therapeutically effective amount of a nucleic acid encoding a CD4 fusion polypeptide, such as, but not limited to a D1D2-Igαtp. Delivery of the polynucleotide encoding the CD4 fusion polypeptide can be achieved using a recombinant expression vector such as a chimeric virus or a colloidal dispersion system, or through the use of targeted liposomes.

Various viral vectors which can be utilized for therapy include, but are not limited to, adenoviral, herpes viral, or retroviral vectors. In one embodiment, a retroviral vector such as a derivative of a murine or avian retroviral vector is utilized. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). In addition, when the subject is a human, a vector such as the gibbon ape leukemia virus (GaLV) is utilized. A number of additional retroviral vectors can incorporate multiple genes. The vectors can transfer or incorporate a gene for a selectable marker so that transduced cells can be identified and generated. By inserting a nucleic acid encoding the CD4 fusion polypeptide into the viral vector, along with another gene which encodes the ligand for a receptor on a specific target cell, for example, the vector is rendered target specific. Retroviral vectors can be made target specific by attaching, for example, a sugar, a glycolipid, or a protein. Targeting can also be accomplished by using an antibody to target the retroviral vector. Those of skill in the art will know of, or can readily ascertain without undue experimentation, specific polynucleotide sequences which can be inserted into the retroviral genome or attached to a viral envelope to allow target specific delivery of the retroviral vector.

Since recombinant retroviruses are defective, they require assistance in order to produce infectious vector particles. This assistance can,be provided, for example, by using helper cell lines that contain plasmids encoding all of the structural genes of the retrovirus under the control of regulatory sequences within the LTR. These plasmids are missing a nucleotide sequence that enables the packaging mechanism to recognize an RNA transcript for encapsidation. Helper cell lines which have deletions of the packaging signal include, but are not limited to Q2, PA317, and PA12, for example. These cell lines produce empty virions, since no genome is packaged. If a retroviral vector is introduced into such cells in which the packaging signal is intact, but the structural genes are replaced by other genes of interest, the vector can be packaged and vector virion produced.

Alternatively, NIH 3T3 or other tissue culture cells can be directly transfected with plasmids encoding the retroviral structural genes gag, pol and env, by conventional calcium phosphate transfection. These cells are then transfected with the vector plasmid containing the genes of interest. The resulting cells release the retroviral vector into the culture medium.

Another targeted delivery system for therapeutic polynucleotides is a colloidal dispersion system. Colloidal dispersion systems include macromolecule complexes, nanocapsules, microspheres, beads, and lipid-based systems including oil-in-water emulsions, micelles, mixed micelles, and liposomes. Liposomes are artificial membrane vesicles that are useful as delivery vehicles in vitro and in vivo. It has been shown that large unilamellar vesicles (LUV), which range in size from 0.2-4.0 μm, can encapsulate a substantial percentage of an aqueous buffer containing large macromolecules. RNA, DNA and intact virions can be encapsulated within the aqueous interior and be delivered to cells in a biologically active form (Fraley et al., *Trends Biochem. Sci.* 6:77, 1981). In order for a liposome to be an efficient gene transfer vehicle, the following characteristics should be present: (1) encapsulation of the genes of interest at high efficiency while not compromising their biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Mannino et al., *Biotechniques* 6:682, 1988; see also U.S. Pat. No. 6,270,795).

The composition of the liposome is usually a combination of phospholipids, particularly high-phase-transition-temperature phospholipids, usually in combination with steroids, such as cholesterol. Other phospholipids or other lipids may also be used. The physical characteristics of liposomes depend on pH, ionic strength, and the presence of divalent cations. Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Particularly useful are diacylphosphatidylglycerols, where the lipid moiety contains from 14-18 carbon atoms, particularly from 16-18 carbon atoms, and is saturated. Illustrative phospholipids include egg phosphatidylcholine, dipalmitoylphosphatidylcholine and distearoylphosphatidylcholine.

The targeting of liposomes can be classified based on anatomical and mechanical factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticuloendothelial system (RES) in organs which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand.

In one embodiment, a mammalian subject, is administered a therapeutically effective dose of a pharmaceutical composition containing nucleic acid encoding a CD4 polypeptide ligated at its C-terminus with a portion of an immunoglobulin comprising a hinge region and a constant domain of a mammalian immunoglobulin heavy chain, wherein the portion of the immunoglobulin is fused at its C-terminus with a polypeptide comprising a tailpiece from the C terminus of the heavy chain of an IgA antibody in a pharmaceutically acceptable carrier.

The CD4 fusion proteins disclosed herein can be used to generate an immune response against an HIV infected cells. In one specific, non-limiting example, the response is antibody dependent cell mediated cytotoxicity. Thus, a method is disclosed herein for inducing antibody dependent cell-mediated cytotoxicity of a cell infected with a lentivirus, such as an immunodeficiency virus (e.g. SIV, HIV-1, HIV-2 or FIV). The method includes contacting the cell with an effective amount of the CD4 fusion protein in the presence of an antigen presenting cell (macrophage, dendritic cell, neutrophil, or B-lymphocyte) or a natural killer cell, thereby stimulating the antigen presenting cell or the natural killer cells, and inducing antibody dependent cell mediated cytotoxicity of the cell infected with the immunodeficiency virus. The immunodeficiency virus can be a human immunodeficiency virus (e.g. HIV-1 or HIV-2). The response (e.g. stimulation of the antigen presenting cell or natural killer cell, inducing antibody dependent cell mediated cytotoxicity, or both) can be produced either in vitro, ex vivo, or in vivo. In one specific, non-limiting example, the natural killer cell or the antigen presenting cell (APC) isolated from a subject, and is contacted with the CD4 fusion protein in vitro. The stimulated natural killer cell and/or APC is subsequently transferred into the subject of interest.

Thus, a method is disclosed herein for stimulating a natural killer cell response or the stimulation of an antigen presenting cell. The method includes contacting the natural killer cell with an effective amount of a CD4 fusion protein, thereby stimulating the response of the natural killer cell. One of skill in the art can readily identify assays for natural killer cell activation, such as, but not limited to, assays of calcium flux and cytoxicity assays. Examples of an assay for natural killer cell activation are provided in the Examples section (see below).

Screening Assays

Figure 6:
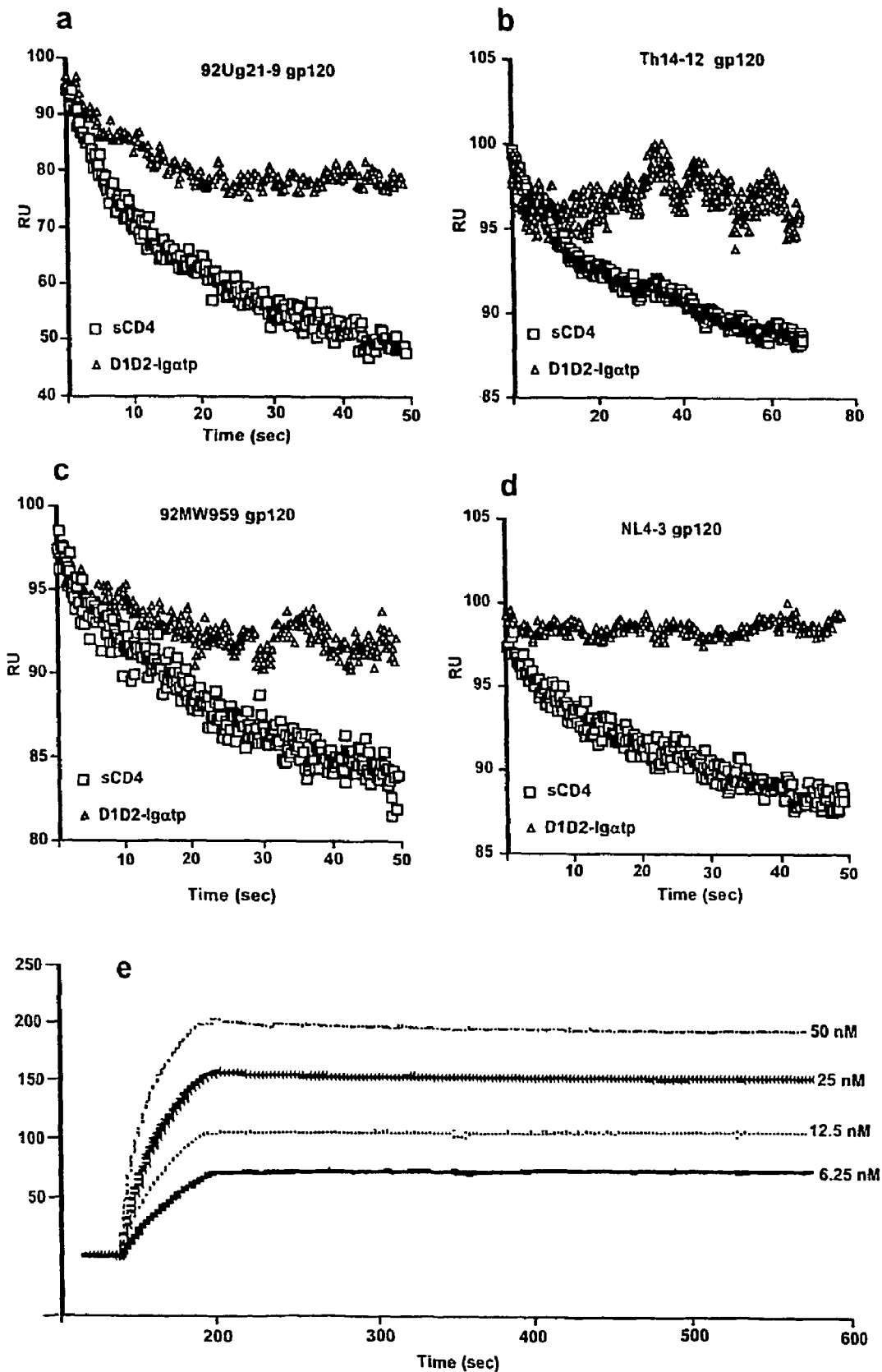

The CD4 fusion proteins disclosed herein are of use for in vitro assays for measuring the binding of the fusion CD4 fusion protein to a selected viral isolate and for identifying affinity of a particular gp120 for CD4. In one embodiment, a biosensor assay is utilized (e.g., see FIG. 6 and the Examples). In another embodiment, an ELISA assay is utilized.

The CD4 fusion protein may be used in assays to screen for new compounds that inhibit HIV replication. In one specific, non-limiting example, a viral isolate or an isolated gp120 is contacted with the CD4 fusion protein in the presence of an agent of interest. The ability of the virus or the gp120 to bind to the CD4 fusion protein is then assessed. Agents of interest include, but are not limited to polypeptides, isolated biological material, chemical compounds, pharmaceutical, or peptidomimetics.

In one embodiment, the CD4 fusion protein is labeled. In another embodiment, the CD4 fusion protein is immobilized on a solid substrate, and the gp120 is labeled. Suitable labels include, but are not limited to, enzymatic, fluorescent, or radioactive labels. Alternatively either the CD4 fusion polypeptide (e.g., D1D2-Igαtp) or the gp120 is covalently linked to a biosensor chip. Either gp120, or the CD4 fusion polypeptide (e.g., D1D2-Igαtp), respectively, is then passed over the chip. This type of assay can is readily adapted to high throughput screening for either synthetic or natural compounds that interfere with the interaction of gp120 and the CD4 fusion polypeptide.

Without further elaboration, it is believed that one skilled in the art can, using this description, utilize the present invention to its fullest extent. The following examples are illustrative only, and not limiting of the remainder of the disclosure in any way whatsoever.

EXAMPLES

Example 1

Materials and Methods

Virus entry. Virion entry into primary lymphocytes was measured using a quantitative real-time PCR assay based upon the generation of early LTR transcripts, adapted from a method previously described (Chun et al., *Nature* 387 (6629):183, 1997). Briefly, freshly isolated peripheral blood mononuclear cells (PBMCs) were activated (OKT3 (1 µg/ml)/IL2 (50 u/ml) for three days and then depleted of CD8+ T-cells by magnetic bead selection (Dynal, Lake Success N.Y.). 3×10⁶ cells were incubated in a volume of 100 µl with the addition of titered viral stocks (Advanced Biotechnologies Columbia, Md.) at a multiplicity of infection (MOI) of 0.1 for two hours at 37° C. Where specified, monomeric sCD4 and D1D2-Igαtp (see below) were preincubated with virus stocks for 10 minutes at 37° C. prior to cell inoculation. Cells were washed with PBS, pelleted through a 100% fetal bovine serum (FBS) cushion (heat inactivated), and then resuspended in DMEM/FBS (heat inactivated) and incubated an additional 4 hrs. Cells were washed and then lysed in a buffer containing an anionic detergent (Gentra, Minneapolis, Minn.) and RNase-A. DNA was precipitated from lysates in isopropanol and resuspended in dH$_2$0. Quantitative real-time PCR was carried out using the following primers and probe: RU5 forward primer: 5'-gctaactagggaacccactgctt-3' (SEQ ID NO:2), RU5 reverse primer: 5'-acaacagacgggcacacactact-3' (SEQ ID NO:3), RU5 probe: 5'-agcctcaataaagcttgccttgagtgcttc-3' (SEQ ID NO:4). Copy numbers were standardized against genomic DNA obtained from an ACH-2 cell line carrying a single integrated HIV-1 genome in each diploid cell (Folks et al., *Science* 231(4738):600, 1986).

Expression and purification of D1D2-Igαtp. The two N-terminal domains of CD4, termed D1 and D2 encode the gp120 binding epitope, and when expressed in the absence of the remaining domains of CD4, retain the capacity to bind gp120. The coding sequences of D1 and D2 was fused to that of Igαtp creating a recombinant protein termed D1D2-Igαtp The coding sequence of this protein is:

```
ATGAACCGGGGAGTCCCTTTTAGGCACTTGCTTCTGGTGCTGCAA (SEQ ID NO:5)
CTGGCGCTCCTCCCAGCAGCCACTCAGGGAAAGAAAGTGGTGCTGGGCA
AAAAGGGGATACAGTGGAACTGACCTGTACAGCTTCCCAGAAGAAGAG
CATACAATTCCACTGGAAAAACTCCAACCAGATAAAGATTCTGGGAAAT
CAGGGCTCCTTCTTAACTAAAGGTCCATCCAAGCTGAATGATCGCGCTG
ACTCAAGAAGAAGCCTTTGGGACCAAGGAAACTTCCCCCTGATCATCAA
GAATCTTAAGATAGAAGACTCAGATACTTACATCTGTGAAGTGGAGGAC
CAGAAGGAGGAGGTGCAATTGCTAGTGTTCGGATTGACTGCCAACTCTG
ACACCCACCTGCTTCAGGGGCAGAGCCTGACCCTGACCTTGGAGAGCCC
CCCTGGTAGTAGCCCCTCAGTGCAATGTAGGAGTCCAAGGGGTAAAAAC
ATACAGGGGGGAAGACCCTCTCCGTGTCTCAGCTGGAGCTCCAGGATA
GTGGCACCTGGACATGCACTGTCTTGCAGAACCAGAAGAAGGTGGAGTT
CAAAATAGACATCGTGGTGCTAGCTTCGGCCGACAAAACTCACACATGC
CCACCGTGCCCAGCACCTGAACTCCTGGGGGGACCGTCAGTCTTCCTCT
TCCCCCCAAAACCCAAGGACACCCTCATGATCTCCCGGACCCCTGAGGT
CACATGCGTGGTGGTGGACGTGAGCCACGAAGACCCTGAGGTCAAGTTC
AACTGGTACGTGGACGGCGTGGAGGTGCATAATGCCAAGACAAAGCCGC
GGGAGGAGCAGTACAACAGCACGTACCGGGTGGTCAGCGTCCTCACCGT
CCTGCACCAGGACTGGCTGAATGGCAAGGAGTACAAGTGCAAGGTCTCC
AACAAAGCCCTCCCAGCCCGCATCGAGAAAACCATCTCCAAAGCCAAAG
GGCAGCCCCGAGAACCACAGGTGTACACCCTGCCCCCATCCCGGGATGA
GCTGACCAAGAACCAGGTCAGCCTGACCTGCCTGGTCAAAGGCTTCTAT
CCCAGCGACATCGCCGTGGAGTGGGAGAGCAATGGGCAGCCGGAGAACA
ACTACAAGACCACGCCTCCCGTGCTGGACTCCGACGGCTCCTTCTTCCT
CTACAGCAAGCTCACCGTGGACAAGAGCAGGTGGCAGCAGGGGAACGTC
TTCTCATGCTCCGTGATGCATGAGGCTCTGCACAACCACTACACGCAGA
```

```
AGAGCCTAAGCTTGTCTGCGGGTAAACCCACCCATGTCAATGTGTCTGT
TGTCATGGCGGAGGTGGACGGCACCTGCTACTGA
```

This amino acid sequence corresponding to this coding sequence is:

```
MNRGVPFRHLLLVLQLALLPAATQGKKVVLGKKGDTVELTCTASQKKSIQFH   (SEQ ID NO:6)
 WKNSNQIKILGNQGSFLTKGPSKLNDRADSRRSLWDQGNFPLIIKNLKIED
 SDTYICEVEDQKEEVQLLVFGLTANSDTHLLQGQSLTLTLESPPGSSPSVQ
 CRSPRGKNIQGGKTLSVSQLELQDSGTWTCTVLQNQKKVEFKIDIVVLASA
 DKTHTCPPCPAPELLGGPSVFLFPPKPDTLMISRTPEVTCVVVDVSHEDPE
 VKFNWYVDGVEVHNAKTKPREEQYNSTYRVVSVLTVLHQDWLNGKEYKCKV
 SNKALPAPIEKTISKAKGQPREPQVYTLPPSRDELTKNQVSLTCLVKGFYP
 SDIAVEWESNGQPENNYKTTPPVLDSDGSFFLYSKLTVDKSRWQQGNVFSC
 SVMHEALHNHYTQKSLSLSAGKPTHVNVSVVMAEVDGTCY
```

The D1D2 domains of CD4 encoded in this construct include the following sequence:

```
ATGAACCGGGGAGTCCCTTTTAGGCACTTGCTTCTGGTGCTGCAACTGGC   (SEQ ID NO:7)
 GCTCCTCCCAGCAGCCACTCAGGGAAAGAAAGTGGTGCTGGGCAAAAAA
 GGGGATACAGTGGAACTGACCTGTACAGCTTCCCAGAAGAAGAGCATAC
 AATTCCACTGGAAAAACTCCAACCAGATAAAGATTCTGGGAAATCAGGG
 CTCCTTCTTAACTAAAGGTCCATCCAAGCTGAATGATCGCGCTGACTCA
 AGAAGAAGCCTTTGGGACCAAGGAAACTTCCCCCTGATCATCAAGAATC
 TTAAGATAGAAGACTCAGATACTTACATCTGTGAAGTGGAGGACCAGAA
 GGAGGAGGTGCAATTGCTAGTGTTCGGATTGACTGCCAACTCTGACACC
 CACCTGCTTCAGGGGCAGAGCCTGACCCTGACCTTGGAGAGCCCCCCTG
 GTAGTAGCCCCTCAGTGCAATGTAGGAGTCCAAGGGGTAAAAACATAGA
 GGGGGGAAGACCCTCTCCGTGTCTCAGCTGGAGCTCCAGGATAGTGGC
 ACCTGGACATGCACTGTCTTGCAGAACCAGAAGAAGGTGGAGTTCAAAA
 TAGACATCGTGGTGCTAGCTTTCGGCCG
```

The coding sequence of the IgG1α tailpiece fusion is:

```
TCGGCCGACAAAACTCACACATGCCCACCGTGCCCAGCACCTGAACTCCT   (SEQ ID NO:8)
 GGGGGGACCGTCAGTCTTCCTCTTCCCCCCAAAACCCAAGGACACCCTC
 ATGATCTCCCGGACCCCTGAGGTCACATGCGTGGTGGTGGACGTGAGCC
 ACGAAGACCCTGAGGTCAAGTTCAACTGGTACGTGGACGGCGTGGAGGT
 GCATAATGCCAAGACAAAGCCGCGGGAGGAGCAGTACAACAGCACGTAC
 CGGGTGGTCAGCGTCCTCACCGTCCTGCACCAGGACTGGCTGAATGGCA
```

-continued

```
AGGAGTACAAGTGCAAGGTCTCCAACAAAGCCCTCCCAGCCCCCATCGA

GAAAACCATCTCCAAAGCCAAAGGGCAGCCCCGAGAACCACAGGTGTAC

ACCCTGCCCCCATCCCGGGATGAGCTGACCAAGAACCAGGTCAGCCTGA

CCTGCCTGGTCAAAGGCTTCTATCCCAGCGACATCGCCGTGGAGTGGGA

GAGCAATGGGCAGCCGGAGAACAACTACAAGACCACGCCTCCCGTGCTG

GACTCCGACGGCTCCTTCTTCCTCTACAGCAAGCTCACCGTGGACAAGA

GCAGGTGGCAGCAGGGGAACGTCTTCTCATGCTCCGTGATGCATGAGGC

TCTGCACAACCACTACACGCAGAAGAGCCTAAGCTTGTCTGCGGGTAAA

CCCACCCATGTCAATGTGTCTGTTGTCATGGCGGAGGTGGACGGCACCT

GCTACTGA
```

The coding sequence for this sequence is:

```
SADKTHTCPPCPAPELLGGPSVFLFPPKPKDTLMISRTPEVTCVVVDVSHEDPE (SEQ ID NO:9)

VKFNWYVDGVEVHNAKTKPREEQYNSTYRVVSVLTVLHQDWLNGKEYKCKVSN

KALPAPIEKTISKAKGQPREPQVYTLPPSRDELTKNQVSLTCLVKGFYPSDIA

VEWESNGQPENNYKTTPPVLDSDGSFFLYSKLTVDKSRWQQGNVFSGSVMHEA

LHNHYTQKSLSLSAGKPTHVNVSVVMAEVDGTCY*
```

The D1D2-Igαtp is predicted to be a hexamer of a dimer (12 binding sites) of sCD4 that we compared to a monomeric sCD4. The D1D2-Igαtp expression vector was designed using standard recombinant DNA methodologies (Chaikin et al., AAAAI, San Francisco, Calif., 1997; J. Sambrook, E. F. F. et al., Cold Spring Harbor Laboratory Press, Plainview, N.Y., 1989). This vector contains a CMV promoter for high level expression of D1D2-Igαtp as well as a gene cassette containing dihydrofolate reductase (DHFR) for amplification in DHFR deficient Chinese hamster ovary (CHO) cells (American type culture collection catalogue (ATCC) No. CRL9096). Purified plasmids were transfected into DHFR deficient CHO cells by a modified Calcium phosphate transfection procedure (Invitrogen, Carlsbad, Calif.). Positive transfectants were initially selected by growth in alpha-MEM without nucleosides supplemented with dialyzed fetal calf serum (Life Technologies, Baltimore, Md.). To increase expression, positive transfectants were pooled and cultured in the presence of increasing concentrations of methotrexate (Sigma, St. Louis Mo.) as previously described (Arthos et al., Cell 57, No. 3:469, 1989). Cell clones expressing high levels of D1D2-Igαtp were identified by Western blot with a rabbit polyclonal antisera raised against sCD4. Clones were subsequently cultured in hollow fiber cartridges (Fiber-Cell Systems, Frederick, Md.) using DMEM plus 4% heat inactivated FBS without methotrexate. Proteins were harvested daily from the extra-capillary space, yielding greater than 5 mg per harvest. D1D2-Igαtp protein was purified in two steps. Initially, supernatants from the extra capillary space of the hollow fiber cartridge were passed over a Hi-trap protein A column (Amersham-Pharmacia Piscataway, N.J.). Bound protein was eluted in 0.1M sodium citrate pH 3.0 and rapidly neutralized with 2M tris-HCL pH 8.0 Peak fractions were subsequently pooled, concentrated and passed over either a Superdex Hi-load 26/60 or a Superdex 200 10/30 gel filtration column (Amersham-Pharmacia Piscataway, N.J.) in PBS, and the peak fraction was collected. With the exception of analytical ultracentrifugation and dynamic light scattering experiments, this was the fraction employed in all biological assays. Silver staining of SDS-page gels indicated that the purity of protein obtained in this manner was >98%. Protein preparations were determined to be endotoxin free using the Chromogenic Limulus Amebocyte Lysate method (Bio Whittaker, Walkersville, Md.)

Optical Biosensor Analysis. General Procedures: All binding assays were performed using a BIA3000 optical biosensor (Biacore, Inc., Uppsala, Sweden). Ligands were immobilized onto the surface of a CM5 sensor chip using the standard amine coupling procedure described by Biacore, Inc. Briefly, the carboxyl groups on the sensor surface were activated by injecting 35 µl of 0.2 M N-ethyl-N'-(3-diethylamino-propyl) carbodiimide (EDC), 0.05 M N-hydroxysuccinimide (NHS). The ligand, suspended in 10 nM acetate buffer, pH 4.0-5.5 (depending on the ligand used) to 5 µg/mL, was passed over the activated surface until the desired surface density was reached. Unreacted carboxyl groups were capped by injecting 35 µl of 1 M ethanolamine (pH 8.0). All samples were injected at a flow rate of 5 microliters/min Bovine serum albumin (BSA) was immobilized on the surface of one flow cell as a reference surface to control for non-specific binding of analyte. The running buffer used was 10 mM HEPES, pH 7.4, 150 mM NaCl, 3 mM EDTA, 0.01% surfactant P-20, 0.5% soluble carboxymethyl dextran (Fluka BioChemika, Inc.). All binding experiments were performed in duplicate and at 25° C.

Interaction Analysis Between sCD4 or D1D2-Igαtp and HIV-1 gp120: sCD4 or HIV-1 gp120 were directly immobilized onto the surface of CM5 sensor chips as described above to surface densities of approximately 250 RU for sCD4 and 500 RU for gp120. This was followed by injection of increasing concentrations of gp120 or sCD4, respectively, through multiple cycles, at a flow rate of 25 microliters/min. The surface was regenerated after each cycle by injecting 25 µl of 5 mM NaOH, 1 M NaCl, followed by a second injection of 25 µl of 4.5 M $MgCl_2$ at a flow rate of 100 microlitersL/min. Association and dissociation rate constants were calculated using the BiaEvaluation 3.1 software (Biacore, Inc., Uppsala, Sweden).

Determination of D1D2-Igαtp: gp120 Binding Ratios: To determine the ratio of gp120 monomers bound per D1D2-Igαtp construct, D1D2-Igαtp in running buffer was passed over a sensor surface to which protein A had been previously immobilized (surface density approximately 1500 RU) at a flow rate of 5 microliters/min. The final surface density of D1D2-Igαtp was approximately 250 RU, and was re-loaded to this density at the beginning of each cycle. After loading of D1D2-Igαtp, the surface was allowed to stabilize for 5 minutes at a flow rate of 5 microliters/min, at which time the specified concentrations of gp120 in running buffer was passed over the surface for a total of 10 minutes. The surface was completely regenerated using three sequential 25 µl injections of 10 mM HCl at a flow rate of 100 microliters/min. Stoichiometries were calculated from the experimentally derived amount of D1D2-Igαtp and gp120 bound per cycle (in RU) using the conversion factor 1 RU=1 pg protein bound per square millimeter flow cell surface area, and the molecular weights of the proteins (D1D2-Igαtp=750,000 Da, gp120=120,000 Da).

Virus coculture. Virus coculture was carried out as previously described (Chun et al., *Nature* 387:183, 1997). Briefly, peripheral blood mononuclear cells (PBMCs) from HIV-1 infected donors were isolated by Ficoll-Hypaque and enriched for CD4+ T-lymphocytes by negative selection with a cocktail of antibody conjugated magnetic beads (StemCell Technologies, Vancouver BC). Cells were cultured in RPMI/10% FBS (heat inactivated) plus OKT3 (1 µg/ml) and IL2 (50 u/ml). In addition, 3 day activated CD8+ T-cell depleted PBMCs from uninfected donors were added at a ratio of approximately 2:1 as necessary. Cultures treated with monomeric sCD4 or D1D2-Igαtp were fed with media containing these proteins such that the original concentration was maintained. Virus replication was assessed by harvesting culture supernatants at regular intervals and measuring p24 antigen using an HIV-1 p24 Antigen Capture Kinetic ELISA (Coulter, Miami, Fla.).

Acute infection. Freshly isolated donor PBMCs were propagated in RPMI supplemented with 10% FBS and stimulated with OKT3 (1 µg/ml) and IL2 (50 u/ml). Prior to infection cells were screened by PCR for CCR5 wild-type homozygosity. Three days after stimulation CD8+ cells were depleted by magnetic bead separation (Dynal, Lake Success, N.Y.), and inoculated with virus as indicated at an MOI of 0.1. Primary isolates were established from six day coculture of patient and normal donor CD8 depleted PBMCs. Cells were exposed to virus for two hours at 37° C., and then washed extensively in PBS. Cells were then plated at a density of $2 \times 10^6$ cells per ml in 24 well tissue culture plates. Immediately after plating various inhibitors were added. Supernatants were collected every other day and virus replication was measured by a kinetic p24 antigen capture ELISA (Coulter, Miami, Fla.) Inhibitor concentrations were maintained in the culture supernatants throughout the culture period.

Analytical Ultracentrifugation and Dynamic Light Scattering. Sedimentation velocity experiments were conducted with the analytical ultracentrifuge Beckman Optima XL-I/A using interference optics, with 400 micrograms of protein (1 µg/µl) dissolved in PBS at a rotor speed of 30,000 rpm and a rotor temperature of 20° C. Data were analyzed by direct boundary modeling with a continuous distribution of Lamm equation solutions (Schuck, *Biophys J* 78, No.3:1606, 2000) and algebraic noise decomposition (Schuck et al., *Biophys J* 76, No. 4:2288, 1999). The distribution of Lamm equation solutions c(s) were calculated with maximum entropy regularization with P=0.68. For deconvolution of the diffusion, the best-fit average frictional ratio of 1.5 was used, resulting in rms deviations of the direct boundary fit of <0.004 fringes in all cases. Sedimentation equilibrium experiments were performed with the absorbance optics at a wavelength of 280 nanometer (nm) and a rotor temperature of 4° C. Equilibrium was attained at rotor speeds of 3,000 rpm, 5,000 rpm, and 7,500 rpm with best-fit distributions with a single-species model for the determination of the weight-average molar mass (Svedberg, T.a.K.O.P., Oxford University Press, London U.K, 1940).

Using tabulated values of the partial specific volume of amino acids (Laue et al., The Royal Society of Chemistry, Cambridge U.K. (1992)) and 0.62±0.02 ml/g for the average partial specific volume of the carbohydrate component (Lewis et al., *Methods Enzymol* 321:136, 2000), and with an average glycosylation of 5 and 15 kDa at the two glycosylation sites per chain, a molar mass of 140 kDa and a partial specific volume of 0.699 ml/g was estimated for a monomeric unit (two chains). Dynamic light scattering experiments were conducted using a Protein Solutions DynaPro 99 instrument with a DynaPro-MSTC200 microsampler (Protein Solutions, Charlottesville, Va.). 20 µl of sample was inserted in the cuvette with the temperature control set to 20° C. The light scattering signal was collected at 90° C. at a wavelength of 808.3 nm. Data analysis was performed with the instrument software, and exported for analysis with the maximum entropy method (Livesey et al., *J. Chem. Phys.* 84:5102, 1986, in the software SEDFIT (Schuck, *Biophys J* 78, No. 3:1606, 2000).

Example 2

Expression of a CD4 Fusion Protein

D1D2-Igαtp is expressed as a highly oligomerized protein. It was first asked whether D1D2-Igαtp was expressed in a highly oligomerized form. To this end, was purified from culture supernatants by protein-A affinity chromatography, and analyzed by standard size exclusion chromatography. When passed over an analytic superdex-200 gel-filtration column a major peak appeared in that fraction corresponding to a molecular weight greater than 650 kDa. A minor fraction, comprising less than 5% of total protein eluted in the 50-100 kDa range. Because the major fraction appeared close to the void volume of the column, it was not possible to accurately estimate its molecular weight from these data. These fractions were then reduced and electrophoresed under denaturing conditions. Western blot analysis with a polyclonal antisera specific for CD4 indicated that D1D2-Igαtp resided primarily in the peak fraction (FIG. 1). When this blot was re-probed with a goat anti-human Ig sera similar results were observed. When the peak fractions were displayed on a Coomassie stained gel, one major band with an approximate molecular weight of 60 kDa was observed. This molecular weight is in close agreement with the unit molecular weight of D1D2-Igαtp predicted by amino acid composition. Thus, D1D2-Igαtp is expressed as a highly oligomerized protein presenting both CD4 and human immunoglobulin heavy chain domains.

Example 3

Comparison of D1D2-Igαtp and Monomeric sCD4 in a Quantitative HIV Entry Assay

To determine the efficiency with which D1D2-Igαtp inhibited HIV entry a real-time PCR based quantitative viral entry assay was established. Virion entry was detected by measuring the level of the initial reverse transcription products in the R and U5 regions of the HIV-1 LTR. The target cells utilized in this assay were three day activated, CD8+ T-cell depleted PBMCs. After optimization, the linear range of this assay typically fell between 25 and 200,000 copies of reverse transcribed product. Two viruses, JR-FL and Bal, both of which utilize the CCR5 coreceptor and were derived after minimal passage of primary isolates, were then employed. To establish the conditions under which sCD4 would enhance viral entry, viral inoculi were briefly pre-incubated with various concentrations of monomeric sCD4 and then carried out the entry assay.

Under these conditions sCD4 at a concentration of either 6.25 or 12.5 nM repeatedly increased viral entry by 1.5 to 3 fold for both JR-FL (FIG. 2) and Bal. At high concentrations (2400 nM) sCD4 reduced viral entry to levels close to background. In contrast across this entire range of concentrations, D1D2-Igαtp reduced virus entry down to levels close to background (FIG. 2A). Thus, at the concentrations in which sCD4 provides optimal enhancement of viral entry D1D2-Igαtp strongly inhibits viral entry. Because each D1D2-Igαtp molecule presents multiple gp120 binding sites the possibility was considered that it might enhance entry at even lower concentrations. D1D2-Igαtp was titered down to 50 picomolar (pM); however, enhanced viral entry (FIG. 2B) was not observed. Therefore it was concluded that unlike sCD4, D1D2-Igαtp does not enhance viral entry at low concentrations.

Example 4

D1D2-Igαtp Versus Monomeric sCD4

Inhibition of Primary Viral Isolates from Patient PBMCs

Figure 3:
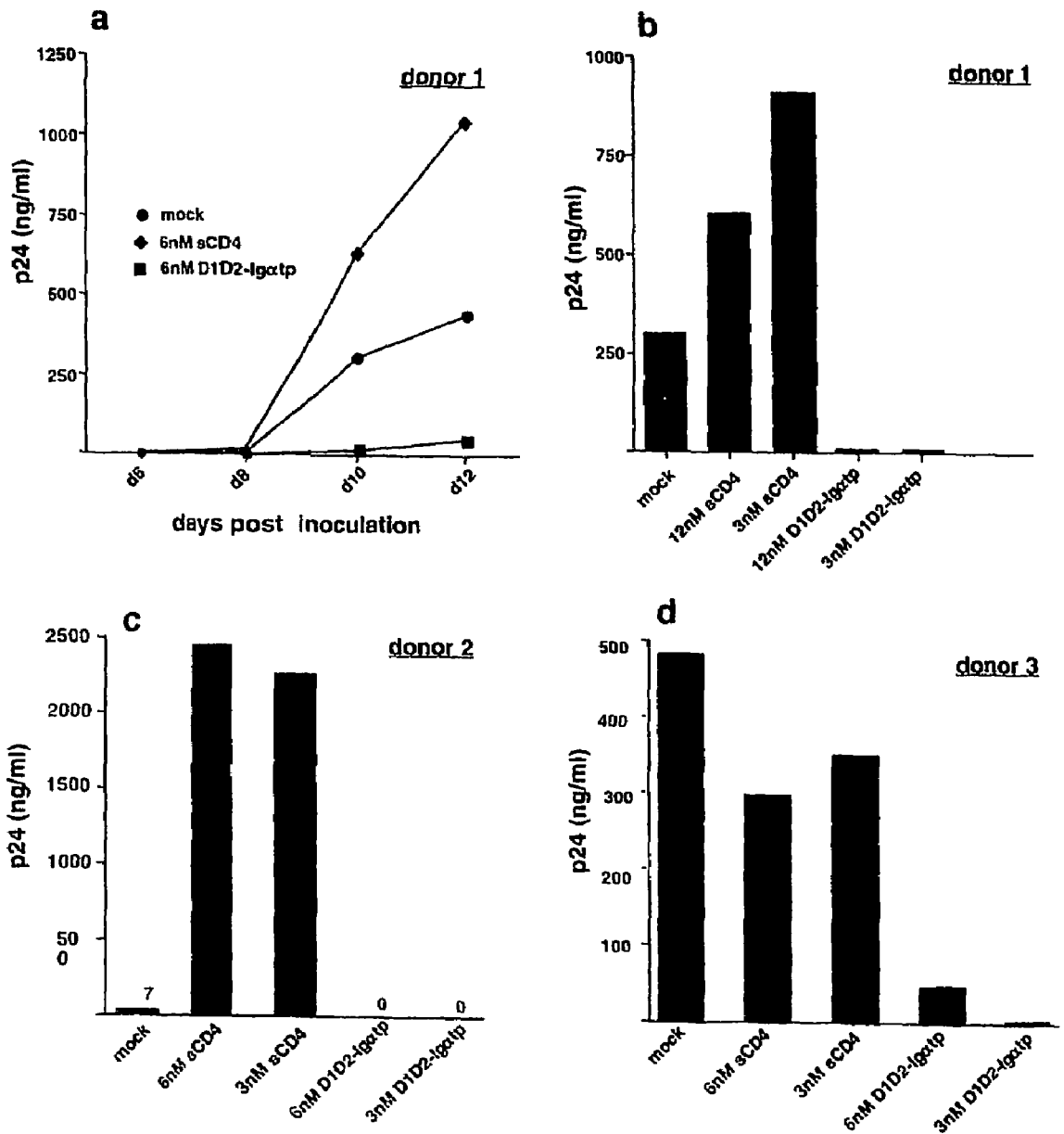

The capacity of monomeric sCD4 and D1D2-Igαtp to inhibit the replication of HIV-1 in cultures of PBMCs derived from HIV-1 infected patients was assessed. CD4+ T cells were isolated from patients and placed into culture along with activated PBMCs from uninfected donors. To these cultures concentrations of monomeric sCD4 were added that enhanced entry of Bal and JR-FL in the viral-entry assay (FIG. 3). In two of the three cocultures the addition of sCD4 resulted in enhanced replication (FIGS. 3A, 3B, and 3C), while in the third coculture sCD4 inhibited viral replication to a limited degree (FIG. 3D.). The same donor CD4+ T-cells were treated in parallel with D1D2-Igαtp. At the same concentrations of monomeric sCD4 that enhanced viral replication in two of three donor cells, D1D2-Igαtp strongly inhibited viral replication in all three donor cells (FIG. 3). Thus, unlike monomeric sCD4, which enhances viral replication at low concentrations, D1D2-Igαtp actively inhibits the replication of primary isolates of HIV-1 in activated T-cells.

Example 5

Figure 4:
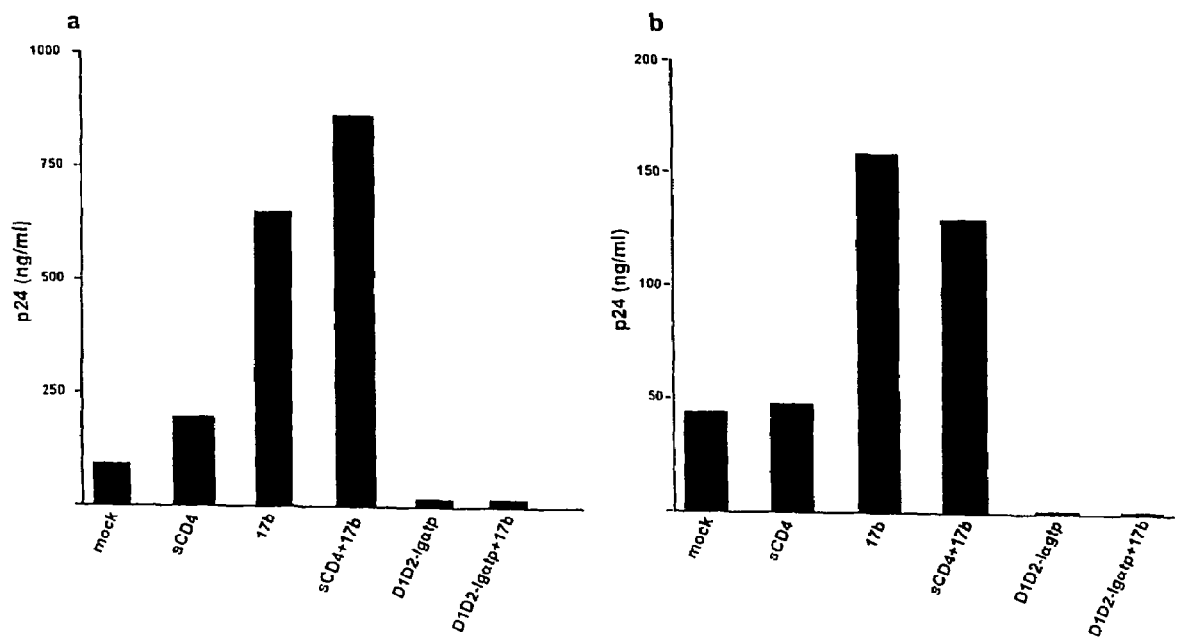

D1D2-Igαtp Inhibits Monoclonal Antibody (mAb) Mediated Enhancement of HIV-1 Replication Similar to sCD4, a number of mAbs specific for gp120 have been shown to enhance replication of HIV-1 at sub-optimal concentrations (Sullivan et al., *J Virol* 69, No. 7:4413, 1995; Schutten et al., *Scand J Immunol* 41, No. 1:18, 1995; Sullivan et al., *J. Virol* 72, No. 6:4694, 1998). One of these mAbs, termed 17b, recognizes an epitope on gp120 that overlaps the CCR5 binding site (Kwong et al., *Nature* 393, No. 6686:648, 1998). This epitope is exposed subsequent to envelope-CD4 ligation. Consequently, 17b reacts more efficiently with gp120 in the presence of sCD4. It was assessed whether D1D2-Igαtp could prevent 17b-mediated enhancement of viral replication. PBMCs were acutely infected with either Bal or a primary isolate derived from a patient shortly after seroconversion. Parallel cultures were treated with 17b, sCD4, 17b plus sCD4, D1D2-Igαtp or 17b plus D1D2-Igαtp, and the extent of viral replication was determined by measurement of p24 antigen in culture supernatants. For both Bal and the primary isolate, 17b alone enhanced viral replication relative to control cultures (FIG. 4). The combination of 17b plus sCD4 also resulted in enhanced replication relative to control cultures. sCD4 alone enhanced replication of Bal to a modest degree. Surprisingly, the combination of sCD4 and 17b appeared to enhance Bal replication in an additive manner (FIG. 4A), suggesting that higher concentrations of one or both of these ligands would be required to observe synergistic inhibition of viral entry. sCD4 demonstrated no enhancing or inhibitory effect on the primary isolate (FIG. 4B). In contrast, D1D2-Igαtp dramatically inhibited replication of both Bal and the primary isolate. Of note, D1D2-Igαtp fully suppressed 17b-mediated enhancement of both Bal and the primary isolate.

Example 6

Stoichiometry of gp120s D1D2-Igαtp Binding

To better understand why D1D2-Igαtp fails to enhance viral replication two biochemical properties of this recombinant protein were characterized. Initially, it was asked how many gp120s could be loaded onto a single D1D2-Igαtp. In addition, the kinetics of these interactions was examined. D1D2-Igαtp, once assembled into an oligomer, should theoretically present twelve independent gp120 binding sites. However, it is unclear whether steric constraints would limit the number of gp120s that actually bind at any given point in time.

To address this issue, a biosensor assay was established that would measure the ratio of gp120 to D1D2-Igαtp under conditions in which the number of gp120s bound to D1D2-Igαtp approached equilibrium. Protein-G was covalently coupled to a biosensor chip, which was subsequently loaded with fixed concentrations of D1D2-Igαtp. To this surface increasing concentrations of gp120 were then added. Once the level of gp120 approaches equilibrium, the number of gp120s bound per D1D2-Igαtp can be determined by employing a standard calculation that relates Biacore response units (RUs) to the mass of protein bound (see Example 1).

Figure 5:
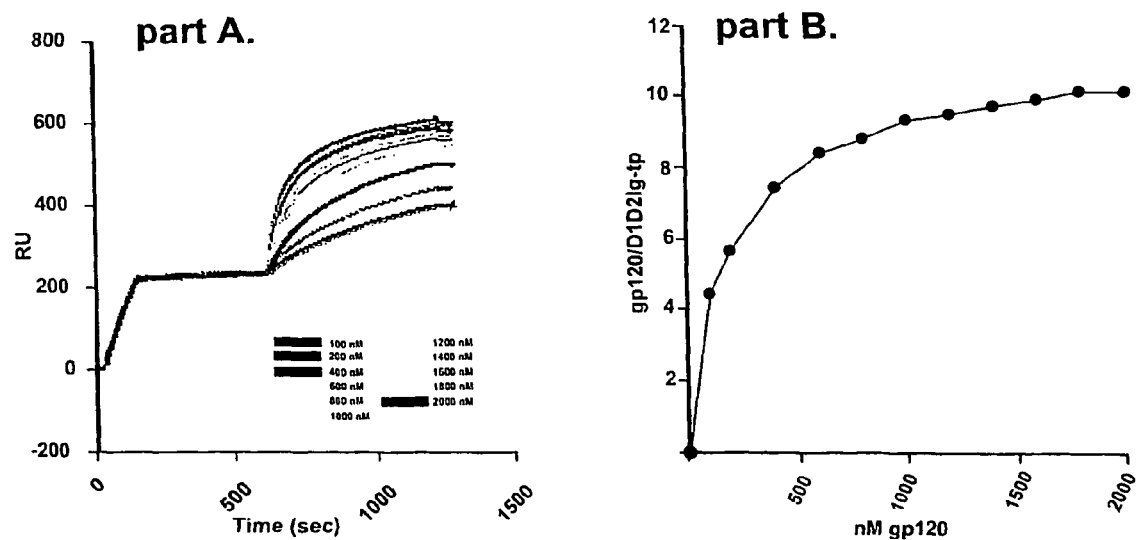

Using a sensor chip loaded with 270 picograms (pg) of D1D2-Igαtp, concentrations of gp120 above 1800 nM approached equilibrium (FIG. 5A). From these curves the number of gp120s recognized by a single D1D2-Igαtp were derived (FIG. 5B). Under the conditions employed, D1D2-Igαtp bound ten gp120s simultaneously. Practical limitations, including injection volumes, protein concentration and a very slow apparent off-rate of gp120 from D1D2-Igαtp, allowed the establishment of conditions at equilibrium was approached, but did not actually achieved. Therefore, the 10:1 ratio should be regarded as a minimum number of gp120s bound per D1D2-Igαtp. Additionally, because gp120s can vary up to 30 kDa in size, this ratio may change when different envelopes are employed. Nevertheless, this analysis demonstrates that D1D2-Igαtp can bind many gp120s simultaneously.

Example 7

Binding Kinetics

One of the most important properties of the CD4 fusion polypeptides disclosed herein protein is the enhanced avidity of these CD4 fusion polypeptides for the CD4 receptor. For example, for a the CD4 fusion polypeptides disclosed herein, twelve binding sites are included (as opposed to four binding sites). Thus, the avidity is greatly enhanced relative to monomeric CD4 or a dimer or tetramer.

It was next asked whether differences in the binding kinetics of D1D2-Igαtp versus monomeric sCD4 might help explain the difference in activity of these two inhibitors at low concentrations. Either sCD4 or D1D2-Igαtp was coupled to a biosensor chip and the binding properties of four different envelope proteins were compared. The four gp120s we employed were: 92MW959, an R5 specific clade C envelope; Th14-12, an R5 specific clade B envelope; 92Ug21-9, an X4 specific lade A envelope; and NL4-3, an X4 specific clade B envelope. With the exception of NL-4-3, each of these envelopes was cloned after minimal passage in vitro (Gao et al., *J Virol* 70, No. 3:1651, 1996).

A dramatic difference was noted in the manner in which all of these envelopes dissociated from D1D2-Igαtp relative to monomeric sCD4. FIG. 6A displays the dissociation curves of each of the envelopes from either D1D2-Igαtp or sCD4. The rate of dissociation is reflected in the slope of the curve such that the more negative the slope the faster the rate of dissociation, while a slope of zero reflects constitutive binding. It is clear from each of the dissociation curves that all of the envelopes dissociate more slowly from D1D2-Igαtp than from sCD4. Of note, each of these curves of D1D2-Igαtp dissociating from gp120 approaches a slope close to zero. These observations are most easily explained by assuming that once an envelope dissociates from one chain of D1D2-Igαtp, it immediately rebinds to the same molecule. Under conditions where this type of rebinding is likely to occur it was not possible to calculate an accurate dissociation constant ($k_d$). Nevertheless, by comparing the sCD4 and D1D2-Igαtp dissociation curves it was concluded that gp120 dissociates from D1D2-Igαtp at a much slower rate than it dissociates from monomeric sCD4.

The binding rate of D1D2-Igαtp for soluble monomeric gp120 employed in this assay are likely to be different than those for gp120 presented on the surface of an infectious virion. The CD4 binding epitope on gp120 is occluded when gp120 is incorporated into a spike (Stamatatos et al., *J Virol* 69, No. 10:6191, 1995) thus reducing its accessibility, (i.e. rate of association), to both membrane bound CD4 as well as sCD4. However, the virion as a target presents on average 216 gp120s distributed as trimmers among 72 spikes (Ozel et al., *Arch Virol* 100, No.3-4:255, 1988). To the extent that D1D2-Igαtp may bind more than one gp120 simultaneously, the rate of dissociation from the virion should be even slower than from a monomeric gp120. The data indicates that, relative to monomeric sCD4, the multivalent nature of D1D2-Igαtp results in slow rates of dissociation from gp120 in a manner that makes D1D2-Igαtp a more efficient inhibitor of viral entry. To determine if D1D2-Igαtp demonstrated high avidity toward HIV gp120 we linked gp120 to the sensor chip at high density and passed increasing concentrations of D1D2-Igαtp over the surface (FIG. 6B). The rate of dissociation is reflected by the slope of the dissociation phase. As can be observed, the slope is close to zero, indicating an extremely avid interaction between HIV gp120 and D1D2-Igαtp.

Example 8

Size and Molar Mass Distribution of D1D2-Igαtp

Figure 7:
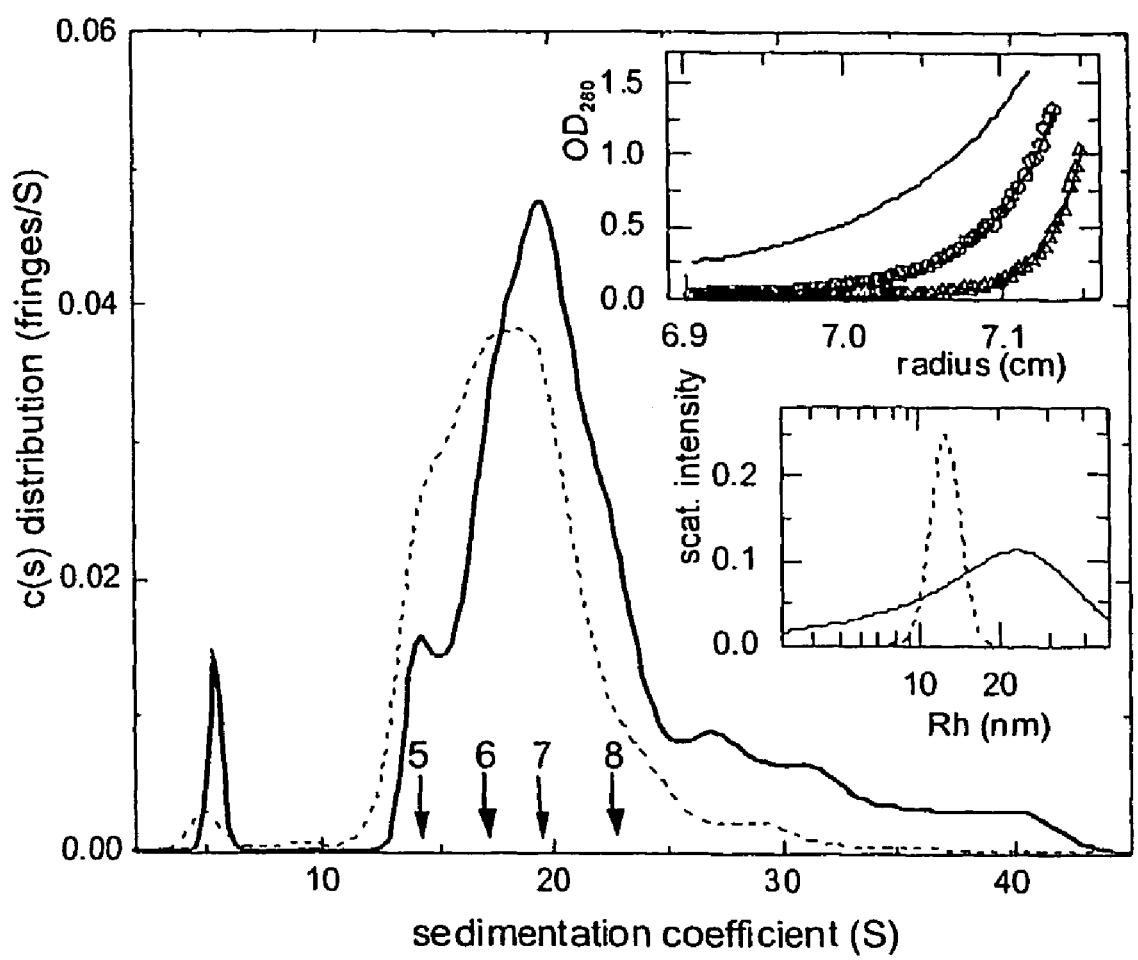

Initially it was postulated that if D1D2-Igαtp were sufficiently large it would prevent the enhancement of viral entry that is associated with suboptimal concentrations of monomeric sCD4. Additionally, establishing the size of D1D2-Igαtp would further help determine if it is sufficiently large to span multiple spikes on the surface of a virion. Protein was initially fractionated by gel filtration and the peak fraction and trailing fraction were collected. Because of the well-known difficulty of precisely measuring the molar mass of large glycoproteins by gel filtration, the size of D1D2-Igαtp was characterized in more detail by analytical ultracentrifugation and dynamic light scattering. The homogeneity of the peak protein fraction was assessed by sedimentation velocity, which showed a broad sedimentation coefficient distribution indicating a heterogeneous size distribution. The large majority of protein in the peak fraction exhibited a sedimentation coefficient between 14 and 25 S (FIG. 7, solid line). Consistent with this observed heterogeneity, the average molar mass measured was dependent on rotor speed, ranging from 5.8 to 8.8 monomer units (FIG. 7, top inset). In order to simplify the analysis of the size-distribution, the trailing fraction which exhibited less heterogeneity was also studied (FIG. 7, dashed line). By comparing the shape of both curves the range of sedimentation coefficients for each oligomer were estimated (arrows in FIG. 7). From these estimations the hydrodynamic radius of the pentamers up to octamers were calculated. The majority of the molecules was calculated to be 11.9-13.5 nm (FIG. 7). This was in excellent agreement with a direct measurement of the hydrodynamic radius by dynamic light scattering, which resulted in a peak at 12.5 nm for the trailing fraction, and significant scattering from the larger oligomers contained in the peak fraction (FIG. 7, bottom inset).

Although the hydrodynamic radius by itself does not contain information about the precise shape of the molecules, for fundamental reasons at least in one dimension the molecules will measure at least twice the hydrodynamic radius. Therefore, it was concluded that D1D2-Igαtp preparation consists of molecules that are at least 24 nm in length. Given that a spike protrudes 10 nm from the surface of a virion (Gelderblom et al., *Virology* 156, No. 1:171, 1987) it can be considered that, once engaged by D1D2-Igαtp, spikes are impeded from interacting with the target cell membrane. Furthermore, the distance from the center and edge of one virion spike to an adjacent spike are 22 nm and 8 nm respectively (Ozel et al., *Arch Virol* 100, No. 3-4:255, 1988; Gelderblom et al., *Virology* 156, No. 1:171, 1987; Forster et al., *J Mol Biol* 298, No. 5:841, 2000; Poignard et al., *Annu*

*Rev Immunol* 19:253, 2001). Thus the data indicates that a D1D2-Igαtp spans multiple spikes on the virion membrane.

Thus, by increasing both the size and the valency of sCD4 one can generate a novel protein that is a highly potent inhibitor of replication and that, unlike monomeric sCD4, does not enhance virus replication at suboptimal concentrations. This has important implications for therapeutic and vaccine strategies. Unlike coreceptor epitopes on gp120, the CD4 receptor binding site is highly conserved making it an attractive target for antiviral therapy. These considerations led to an examination of the biological attributes of sCD4 that prevents it from inhibiting viral replication of primary isolates.

The enhancing activity of sCD4 on HIV entry is considered to be one of the critical unintended effects of this potential anti-viral agent that has led to its failure in clinical trials. As disclosed herein, by increasing both the size and the valency of sCD4 an agent can be generated that no longer enhances viral replication at sub-optimal concentrations.

An extremely large immunoglobulin derivative, termed D1D2-Igαtp, has been constructed that is comprised of, on average, twelve IgG1 heavy chains fused to the two amino-terminal domains of CD4. The CD4 receptor is thought to extend about 7 nm from the membrane of a lymphocyte, while the extracellular loops of CCR5 lie closer to the cell surface (Poignard et al., *Annu Rev Immunol* 19:253, 2001). One of the proposed functions of membrane-bound CD4 is to bring the virion into close proximity to CCR5 and thus to the cell membrane so that the fusion process can proceed. This process is dependent in part on CD4-induced conformational changes in gp120 (Doranz et al., *J Virol* 73, No. 12:10346, 1999; Trkola et al., *Nature* 384, No. 6605:184, 1996; Wu et al., *Nature* 384, No. 6605:179, 1996; Zhang et al., *Biochemistry* 38, No. 29:9405, 1999). Thus, without being bound by theory, by generating a molecule of sufficient size, such as the D1D2-Igαtp, the attachment of such agents to the surface of a virion prevents that virion from gaining close proximity to fusion components on the cell surface.

In this instance, any conformational changes in gp120 induced by such an agent are less likely to promote fusion. Viral spikes are estimated to rise 10 nm from the surface of a virion (Ozel et al., *Arch Virol* 100, No. 3-4:255, 1988; Gelderblom et al., *Virology* 156, No. 1:171, 1987). The data from dynamic light-scattering experiments and sedimentation velocity centrifugation indicate that the hydrodynamic radius of D1D2-Igαtp is approximately 12 nm (diameter=24 nm). Thus, without being bound by theory, it is likely that once D1D2-Igαtp engages a spike and induces a conformational change in the envelope, that spike is unlikely to gain the close proximity to the target cell membrane necessary for fusion to occur because of the bulk of the hexameric D1D2-Igαtp.

In viral entry assays D1D2-Igαtp inhibited viral entry at very low concentrations relative to monomeric sCD4. Furthermore, unlike sCD4, there was never an observation of any significant enhancing activity as the D1D2-Igαtp was titered out. This is consistent with the hypothesis that a large molecule renders induction of fusion components on the virion irrelevant.

Unlike monomeric sCD4, D1D2-Igαtp inhibited primary isolates at relatively low concentrations. This activity could result in part from the presentation by D1D2-Igαtp of twelve gp120 binding sites in close proximity to each other. By presenting CD4 as a soluble dodecamer it can more effectively compete with clusters of CD4 receptors on the target cell membrane. When the dissociation of gp120 from monomeric sCD4 and D1D2-Igαtp were compared it was found that gp120 dissociated much more slowly from D1D2-Igαtp than sCD4. The rate of dissociation of D1D2-Igαtp from soluble gp120 is likely to be different from that of virion-associated gp120. However, it is also likely that the trend is the same: D1D2-Igαtp also likely dissociates from virion spikes more slowly than monomeric sCD4.

Without being bound by theory, it is possible that a single D1D2-Igαtp binds more than one of the three gp120s included in a spike. It was determined that a single D1D2-Igαtp is either sufficiently flexible or otherwise folded to accommodate at least 10 gp120s, supporting the possibility that two or even three of the envelopes on a spike could be occupied by different chains of a single D1D2-Igαtp. Additionally, because spikes on a virion are arranged approximately 22 nm apart (center to center), a single D1D2-Igαtp, with an estimated diameter of 24 nm, may span multiple spikes. Binding of one D1D2-Igαtp to multiple envelopes on a virion, whether within or across spikes, should significantly slow the rate at which it dissociates from that virion. To the extent that spikes are occupied and kept sufficiently distant from the cell membrane they cannot participate in the fusion process. Thus the size and capacity for multivalent ligation confer upon D1D2-Igαtp two properties that distinguish it from monomeric sCD4: (1) it does not enhance viral replication at suboptimal concentrations, and (2) it efficiently inhibits replication of primary isolates. These properties confer on D1D2-Igαtp therapeutic properties not observed with monomeric sCD4 in previously reported clinical trials (Schooley et al., *Ann Intern. Med* 112, No.4: 247, 1990).

Similar to sCD4, mAbs specific for gp120 car enhance the replication of many primary isolates. Additionally, polyclonal sera from infected patients, or individuals vaccinated with envelope based immunogens also enhance HIV-1 replication (Sullivan et al., *J Virol* 69, No. 7:4413, 1995; Sorensen et al., *J Immunol* 162, No. 6:3448, 1999). As with sCD4, this effect is seen as the concentration of the sera or mAb is titered out to very high dilutions. As has been noted elsewhere, this property of gp120-specific antibodies may negatively impact on the effectiveness of anti-envelope humoral responses, both in the context HIV disease as well as vaccination. In order to ask whether D1D2-Igαtp would interfere with antibody-mediated enhancement of viral replication mAb 17b, an antibody that has previously been shown to enhance viral replication, was employed. Of note, 17b recognizes gp120 more efficiently in the presence of monomeric sCD4 (Sullivan. et al., *J Virol* 69, No. 7:4413, 1995; Schutten et al., *Scand J Immunol* 41, No. 1:18, 1995; Doranz et al., *J Virol* 73, No. 12:10346, 1999). In fact, D1D2-Igαtp eliminated the enhancing effects of 17b. Without being bound by theory, this may have occurred because the size of D1D2-Igαtp limits the access of 17b to the virion, or it may have prevented 17b enhancement by keeping virion spikes at a distance from the target cell membrane (see above). In this respect, D1D2-Igαtp illustrates two highly desirable attributes of a potent neutralizing antibody, it dissociates slowly from gp120, and it is large and therefore likely to keep the virion separated from the cell membrane.

In summary, disclosed herein are CD4 fusion proteins that address one of the principle properties of sCD4 that has prevented sCD4 from being developed as an effective anti-viral agent. Since sCD4 binds to one of the few structures on gp120 that is almost invariably conserved in replication competent viruses, the CD4 binding epitope on gp120 remains a highly attractive target for both therapeutic strategies and vaccines. Disclosed herein are molecules that do not have the intrinsic capacity of sCD4 to enhance viral replication, but have an increased ability to suppress virus replication. Thus, this disclosure provides novel insight into requirements of effective inhibitors of viral entry, and provides molecules that are of use as therapeutic modalities.

Example 9

D1D2-Igαtp Neutralizes CCR5-Utilizing Primary Isolates

The ability of D1D2-Igαtp to neutralize four primary isolates of HIV-1 was tested. In addition, two viruses, Bal and JR-F1 derived from molecularly cloned HIV viruses were also tested. A standard virus neutralization assay (Letvin et al., *J. Virol* 75:4165-4175, 2001) in which decreasing concentrations of D1D2-Igαtp were incubated with the each of the six isolates and activated peripheral blood mononuclear cells. Parallel experiments were carried out with sCD4 as a point of comparison. Twenty-four hours post inoculation cells were washed and placed into standard culture conditions. Supernatants were collected over a period of fourteen days. Viral replication was assessed by measurement of reverse transcriptase in culture supernatants. The data is shown in FIG. 8, wherein the data presented represents the percent inhibition on a day prior to the peak day of viral replication relative to a parallel culture in which no inhibitor was added. The 90% inhibitory concentrations of D1D2-Igαtp are as good or better than the most efficient neutralizing antibodies (Burton et al., *Science* 266 1024-1027, 1994).

D1D2-Igαtp inhibited viral replication in each primary viral isolate by 90% at a concentration below 2.8 nM (see FIG. 8).

Example 10

Figure 9:
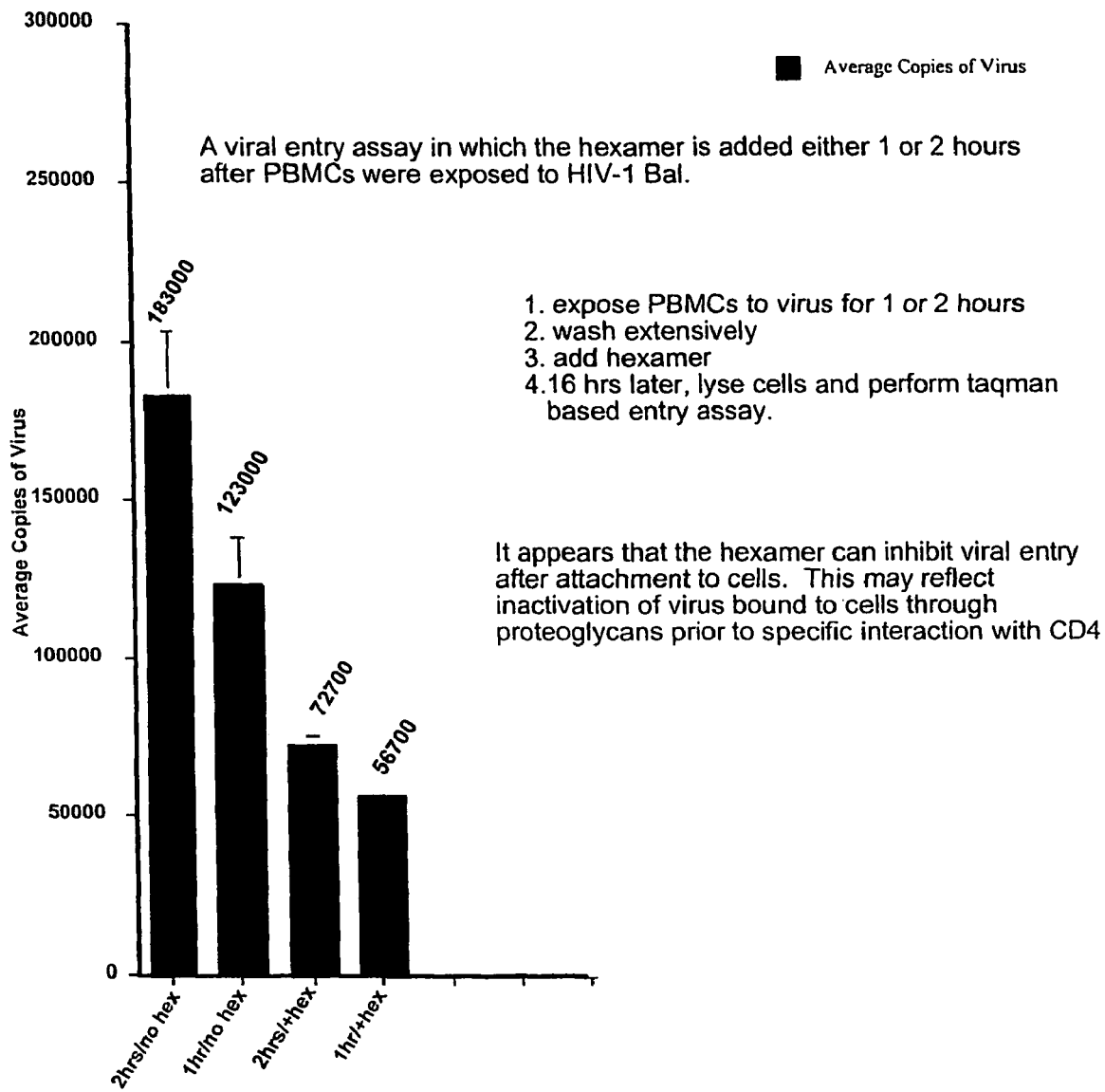

Inhibition of Viral Entry After Attachment of the Virus to the Target Cell Membrane A viral entry assay, taqman (see Example 3), was used to determine the ability of D1D2-Igαtp to inhibit viral entry. Briefly, PBMCs were exposed to virus (HIV-1 Bal) for one or two hours, and then washed extensively. Thus, the only virus remaining is that already attached to the surface of cells. D1D2-Igαtp was the added to the cells at a concentration of 25 nM. Sixteen hours later, the cells were lysed and a taqman based assay was performed. As shown in FIG. 9, D1D2-Igαtp inhibited the entry of virus, subsequent to initial attachment of the virions to cells into CD4+ T-cells by 50%. Without being bound by theory, it is possible that this result reflects inactivation of virus bound to cells through proteoglycans prior to specific interaction of the gp120 component with CD4.

Example 11

Generation of a Second D1D2-Igαtp with Altered Properties

As disclosed above, the DNA coding sequence of D1D2-Igαtp is:

```
ATGAACCGGGGAGTCCCTTTTAGGCACTTGCTTCTGGTGCTGCAACTGGC    (SEQ ID NO:5)
GCTCCTCCCAGCAGCCACTCAGGGAAAGAAAGTGGTGCTGGGCAAAAAAG
GGGATACAGTGGAACTGACCTGTACAGCTTCCCAGAAGAAGAGCATACAA
TTCCACTGGAAAAACTCCAACCAGATAAAGATTCTGGGAAATCAGGGCTC
CTTCTTAACTAAAGGTCCATCCAAGCTGAATGATCGCGCTGACTCAAGAA
GAAGCCTTTGGGACCAAGGAAACTTCCCCCTGATCATCAAGAATCTTAAG
ATAGAAGACTCAGATACTTACATCTGTGAAGTGGAGGACCAGAAGGAGGA
GGTGCAATTGCTAGTGTTCGGATTGACTGCCAACTCTGACACCCACCTGC
TTCAGGGGCAGAGCCTGACCCTGACCTTGGAGAGGCCCCCTGGTAGTAGC
CCCTCAGTGCAATGTAGGAGTCCAAGGGGTAAAAACATACAGGGGGGGAA
GACCCTCTCCGTGTCTCAGCTGGAGCTCCAGGATAGTGGCACCTGGACAT
GCACTGTCTTGCAGAACCAGAAGAAGGTGGAGTTCAAAATAGACATCGTG
GTGCTAGCTTCGGCCGACAAAACTCACACATGCCCACCGTGCCCAGCACC
TGAACTCCTGGGGGGACCGTCAGTCTTCCTCTTCCCCCCAAAACCCAAGG
ACACCCTCATGATCTCCCGGACCCCTGAGGTCACATGCGTGGTGGTGGAC
GTGAGCCACGAAGACCCTGAGGTCAAGTTCAACTGGTACGTGGACGGCGT
GGAGGTGCATAATGCCAAGACAAAGCCGCGGGAGGAGCAGTACAACAGCA
CGTACCGGGTGGTCAGCGTCCTCACCGTCCTGCACCAGGACTGGCTGAAT
GGCAAGGAGTACAAGTGCAAGGTCTCCAACAAAGCCCTCCCAGCCCCCAT
CGAGAAAACCATCTCCAAAGCCAAAGGGCAGCCCCGAGAACCACAGGTGT
```

-continued

ACACCCTGCCCCCATCCCGGGATGAGCTGACCAAGAACCAGGTCAGCCTG

ACCTGCCTGGTCAAAGGCTTCTATCCCAGCGACATCGCCGTGGAGTGGGA
GAGCAATGGGCAGCCGGAGAACAACTACAAGACCACGCCTCCCGTGCTGG
ACTCCGACGGCTCCTTCTTCCTCTACAGCAAGCTCACCGTGGACAAGAGC
AGGTGGCAGCAGGGGAACGTCTTGTCATGCTCCGTGATGCATGAGGCTCT
GCACAACCACTACACGCAGAAGAGCCTAAGCTTGTCTGCGGGTAAACCCA
CCCATGTCAATGTGTCTGTTGTCATGGCGGAGGTGGACGGCACCTGCTAC
TGA

The amino acid sequence of D1D2-Igαtp is:

MNRGVPFRHLLLVLQLALLPAATQGKKVVLGKKGDTVELTCTASQKKSIQF (SEQ ID NO:6)

HWKNSNQIKILGNQGSFLTKGPSKLNDRADSRRSLWDQGNFPLIIKNLKIE
DSDTYICEVEDQKEEVQLLVFGLTANSDTHLLQGQSLTLTLESPPGSSPSV
QCRSPRGKNIQGGKTLSVSQLELQDSGTWTCTVLQNQKKVEFKTDIVVLAS
ADKTHTCPPCPAPELLGGPSVFLFPPKPKDTLMISRTPEVTCVVVDVSHED
PEVKFNWYVDGVEVHNAKTKPREEQYNSTYRVVSVLTVLHQDWLNGKEYKC
KVSNKALPAPIEKTISKAKGQPREPQVYTLPPSRDELTKNQVSLTCLVKGF
YPSDIAVEWESNGQPENNYKTTPPVLDSDGSFFLYSKLTVDKSRWQQGNVF
SCSVMHEALHNHYTQKSLSLSAGKPTHVNVSVVMAEVDGTCY*.

Using molecular cloning procedures and site directed mutagenesis of DNA as has been previously described (see Kim and Maas, *Biotechniques* 28(2):196-8, 2000), a variant (termed FD1D2-Igαtp, or mutant F) was produced. This variant includes amino acids of an $IgG_2$ that are involved in binding to Fc receptors. The DNA coding sequence of FD1D2-Igαtp is as follows:

ATGAACCGGGGAGTCCCTTTTAGGCACTTGCTTCTGGTGCTGCAACTGGC (SEQ ID NO:10)

GCTCCTCCCAGCAGCCACTCAGGGAAAGAAAGTGGTGCTGGGCAAAAAAGG

GGATACAGTGGAACTGACCTGTACAGCTTCCCAGAAGAAGAGCATACAAT

TCCACTGGAAAAACTCCAACCAGATAAAGATTCTGGGAAATCAGGGCTCC

TTCTTAACTAAAGGTCCATCCAAGCTGAATGATCGCGCTGACTCAAGAAG

AAGCCTTTGGGACCAAGGAACTTCCCCCTGATCATCAAGAATCTTAAGAT

AGAAGACTCAGATACTTACATCTGTGAAGTGGAGGACCAGAAGGAGGAGG

TGCAATTGCTAGTGTTCGGATTGACTGCCAACTCTGACACCCACCTGCTT

CAGGGGCAGAGCCTGACCCTGACCTTGGAGAGCCCCCCTGGTAGTAGCCC

CTCAGTGCAATGTAGGAGTCCAAGGGGTAAAAACATACAGGGGGGGAACA

CCCTCTCCGTGTCTCAGCTGGAGCTCCAGGATAGTGGCACCTGGACATGC

ACTGTCTTGCAGAACCAGAAGAAGGTGGAGTTCAAAATAGACATCGTGGT

GCTAGCTTCGGCCGACAAAACTCACACATGCCCACCGTGCCCAGCACCTC

-continued

```
CAGTCGCGGGACCGTCAGTCTTCCTCTTCCCCCCAAAACCCAAGGACACC

CTCATGATCTCCCGGACCCCTGAGGTCACATGCGTGGTGGTGGACGTGAG

CCACGAAGACCCTGAGGTCAAGTTCAACTGGTACGTGGACGGCGTGGAGG

TGCATAATGCCAAGACAAAGCCGCGGGAGGAGCAGTACAACAGCACGTAC

CGGGTGGTCAGCGTCCTCACCGTCCTGCACCAGGAGTGGCTGAATGGCAA

GGAGTACAAGTGCAAGGTCTCCAACAAAGCCCTCCCAGCCCCCATCGAGA

AAACCATCTCCAAAGCCAAAGGGCAGCCCCGAGAACCACAGGTGTACACC

CTGCCCCCATCCCGGGATGAGCTGACCAAGAACCAGGTCAGCCTGACCTG

CCTGGTCAAAGGCTTCTATCCCAGCGACATCGGCGTGGAGTGGGAGAGCA

ATGGGCAGCCGGAGAACAACTACAAGACCACGCCTCCCGTGCTGGACTCC

GACGGCTCCTTCTTCCTCTACAGCAAGCTCACCGTGGACAAGAGCAGGTG

GCAGCAGGGGAACGTCTTCTCATGCTCCGTGATGCATGAGGCTCTGCACA

ACCACTACACGCAGAAGAGCCTAAGCTTGTCTGCGGGTAAACCCACCCAT

GTCAATGTGTCTGTTGTCATGGCGGAGGTGGACGGCACCTGCTACTGA
```

This nucleic acid sequence encodes the following amino acid sequence:

```
MNRGVPFRHLLLVLQLALLPAATQGKKVVLGKKGDTVELTCTASQKKSIQF      (SEQ ID NO:11)

HWKNSNQIKILGNQGSFLTKGPSKLNDRADSRRSLWDQGNFPLIIKNLKIE

DSDTYICEVEDQKEEVQLLVFGLTANSDTHLLQGQSLTLTLESPPGSSPSV

QCRSPRGKNIQGGKTLSVSQLELQDSGTWTCTVLQNQKKVEFIKDIVVLAS

ADKTHTCPPCPAPPVAGPSVFLFPPKPKDTLMISRTPEVTCVVVDVSHEDP

EVKFNWYVDGVEVHNAKTKPREEQYNSTYRVVSVLTVLHQDWLNGKEYKCK

VSNKALPAPIEKTISKAKGQPREPQVYTLPPSRDELTKNQVSLTCLVKGFY

PSDIAVEWESNGQPENNYKTTPPVLDSDGSFFLYSKLTVDKSRWQQGNVFS

CSVMHEALHNHYTQKSLSLSAGKPTHVNVSVVMAEVDGTCY,
``` termed FD1D2-Igαtp.

Figure 14:
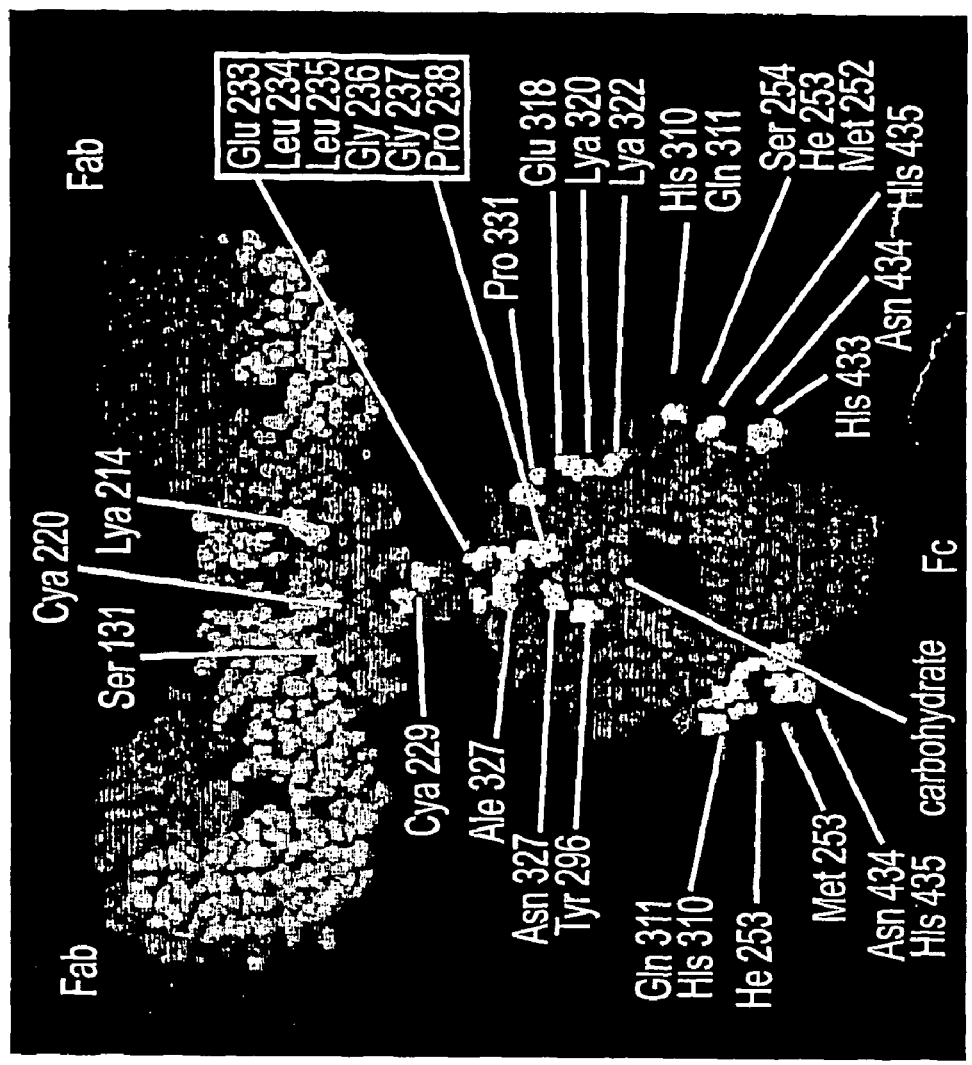
FIG. 14 is a schematic diagram showing D1D2-Igαtp and the residues altered to obtain mutant F. In FD1D2-Igαtp, principle residues in the area responsible for binding to Fc gamma receptors (bright areas of residues responsible for binding of the immunoglobulin molecule to Fc) are mutated.

The differences between the D1D2-Igαtp (SEQ ID NO: 5) and FD1D2-Igαtp (SEQ ID NO: 10) nucleic acid sequences are as follows:
1. nucleotide 652 of D1D2-Igαtp was changed from G to C
2. nucleotide 653 of D1D2-Igαtp was changed from A to C
3. nucleotide 655 of D1D2-Igαtp was changed from C to G
4. nucleotides 658-660 of D1D2-Igαtp were deleted
5. nucleotide 662 of D1D2-Igαtp was changed from G to C The resulting differences between the D1D2-Igαtp (SEQ ID NO: 6) and FD1D2-Igαtp (SEQ ID NO: 11) are in amino acid sequences 218-221 (see SEQ ID NO:6). These substitutions are as follows (see FIG. 14 for reference points on an intact IgG, residues 218-221 in D1D2-Igαtp correspond to residues 233-238 in an intact IgG$_1$):

D1D2-Igαtp: Glu Leu Leu Gly

FD1D2-Igαtp: Pro Val—Ala

IgG$_2$s exhibit a substantially lower affinity for CD16, CD32 and CD64 when compared to standard human IgG$_1$s. This difference occurs as a consequence of different amino acids in the IgG$_1$ and IgG$_2$ at specific positions in the proteins that interact directly with CD16, CD32 and CD64 (see FIG. 14). These amino acids and their role in the recognition of Fc receptors have been described extensively (see Shields et al., *J. Biol Chem*. 276(9):6591-604, 2001). The residues in D1D2-Igαtp (shown above) contain substitutions such that the residues involved in IgG$_1$ recognition were replaced with the corresponding residues encoded by IgG$_2$ (FIG. 15). Thus, a chimeric IgG1/IgG2 CH2CH3 domain has been included within the overall framework of D1D2-Igαtp. The resulting molecule, FD1D2-Igαtp, binds to CD16 and Cd32 with a substantially lower apparent affinity, as described below.

Example 12

FD1D2-Igαtp Binds to Fc Receptors with an Altered Affinity

As disclosed herein, D1D2-Igαtp is a fusion protein made from three proteins: human CD4, human IgG1, and human IgA. The domains of human IgG$_1$ that are included in D1D2Igαtp are termed "CH2CH3." The CH2CH3 domain includes a specific epitope that binds to a family of receptors called the Fc receptors. The three most extensively characterized Fc receptors are termed CD16, CD32, and CD64. A standard human IgG1 antibody binds to CD16 and CD32 with low affinity.

Figure 10:
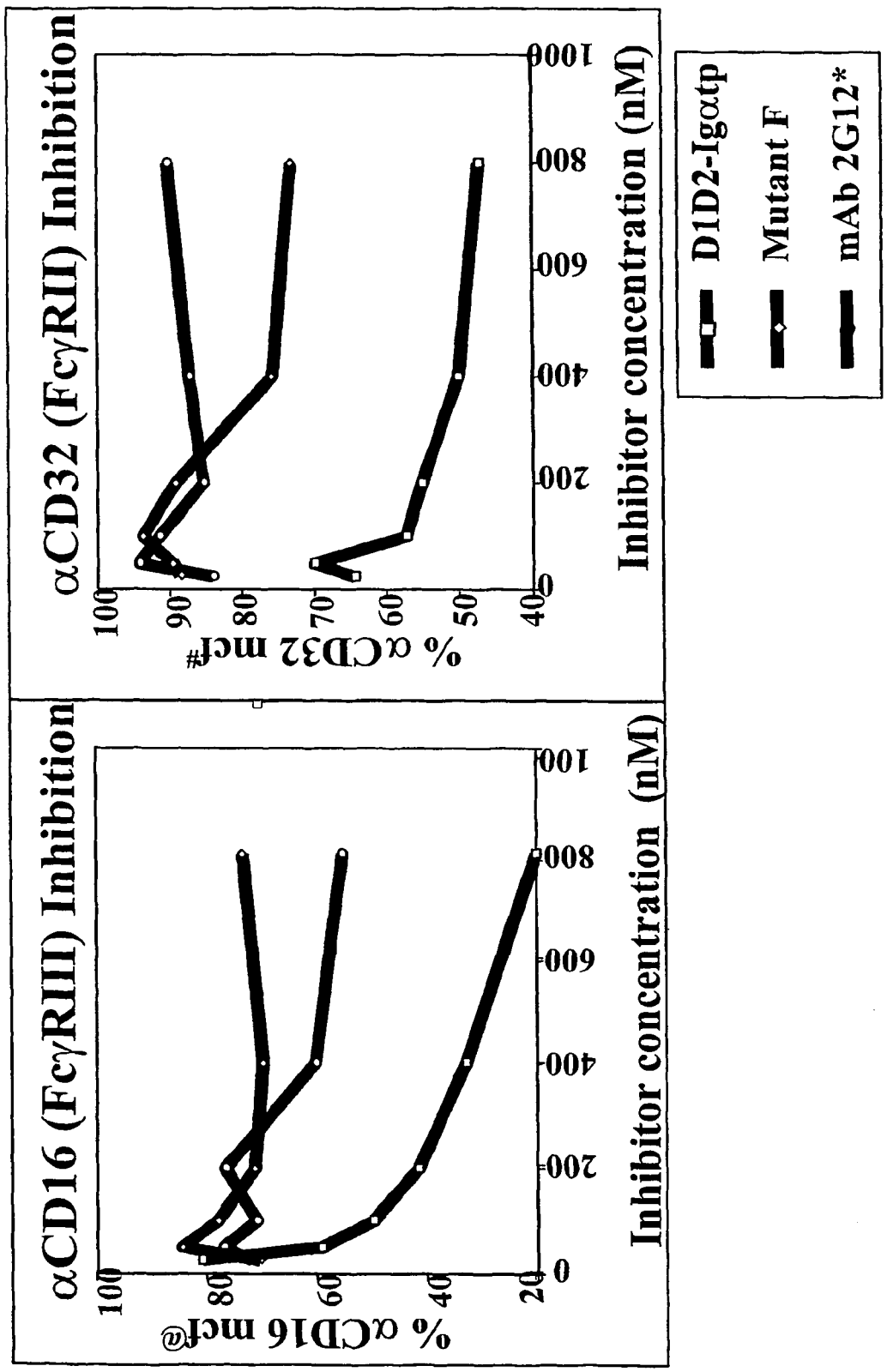

As a consequence of the extensive polymerization of CH2CH3 in the context of D1D2-Igαtp there is a high affinity of this molecule of CD16 and CD32 receptors (see FIG. 10). In order to compare the binding affinity of D1D2-Igαtp and FD1D2-Igαtp competition experiments for CD16 binding were performed using a fluorescence labeled anti CD16 antibody as a competitor. Cells were incubated at 4° C. with a constant amount of the labeled anti CD16 antibody and increasing concentrations of D1D2-Igαtp or FD1D2-Igαtp. The extent of anti CD16 binding was measured by flow cytometry. The % CD16 mean channel fluorescence (mcf) was calculated as follows:

$$\% \ CD16 \ mcf = \frac{(CD16mcf\text{-backgroud}) - (CD16 \text{ with inhibitor } mcf\text{-background})}{(CD16 \ mcf\text{-background})} \times 100$$

The results demonstrate that D1D2-Igαtp efficiently competes for binding to CD16, while FD1D2-Igαtp competes less efficiently (FIG. 10A). Antibody 2G12 (negative control, a human IgG$_1$), did not compete for binding to CD16.

In order to compare the binding affinity of D1D2-Igαtp and FD1D2-Igαtp, competition experiments for CD32 binding were also performed. These studies used a labeled anti-CD32 antibody as a competitor. The % CD32 mean channel fluorescence (mcf) was calculated as follows:

$$\% \ CD32 \ mcf = \frac{(CD32mcf\text{-backgroud}) - (CD32 \text{ with inhibitor } mcf\text{-background})}{(CD32 \ mcf\text{-background})} \times 100$$

FIG. 10B shows the binding to CD32 obtained in the presence of 1-1000 nM of competitor (2G12, a human IgG$_1$). D1D2-Igαtp efficiently competes for binding to CD32, while FD1D2-Igαtp competes less efficiently. Antibody 2G12, (negative control, a human IgG$_1$), did not compete for binding to CD32.

Example 13

Effect of FD1D2-Igαtp and D1D2-Igαtp on Natural Killer Cells

The binding and cross-linking of CD16 on antigen presenting cells and natural killer (NK) cells by IgG$_1$s results in biological responses in those cells that promote immune responses. In one example, this response can be measured by measuring a calcium flux in NK cells. Calcium influx can be measured as described in Rabin et al., *J Immunol.* 162(7): 3840-50, 1999.

Figure 11:
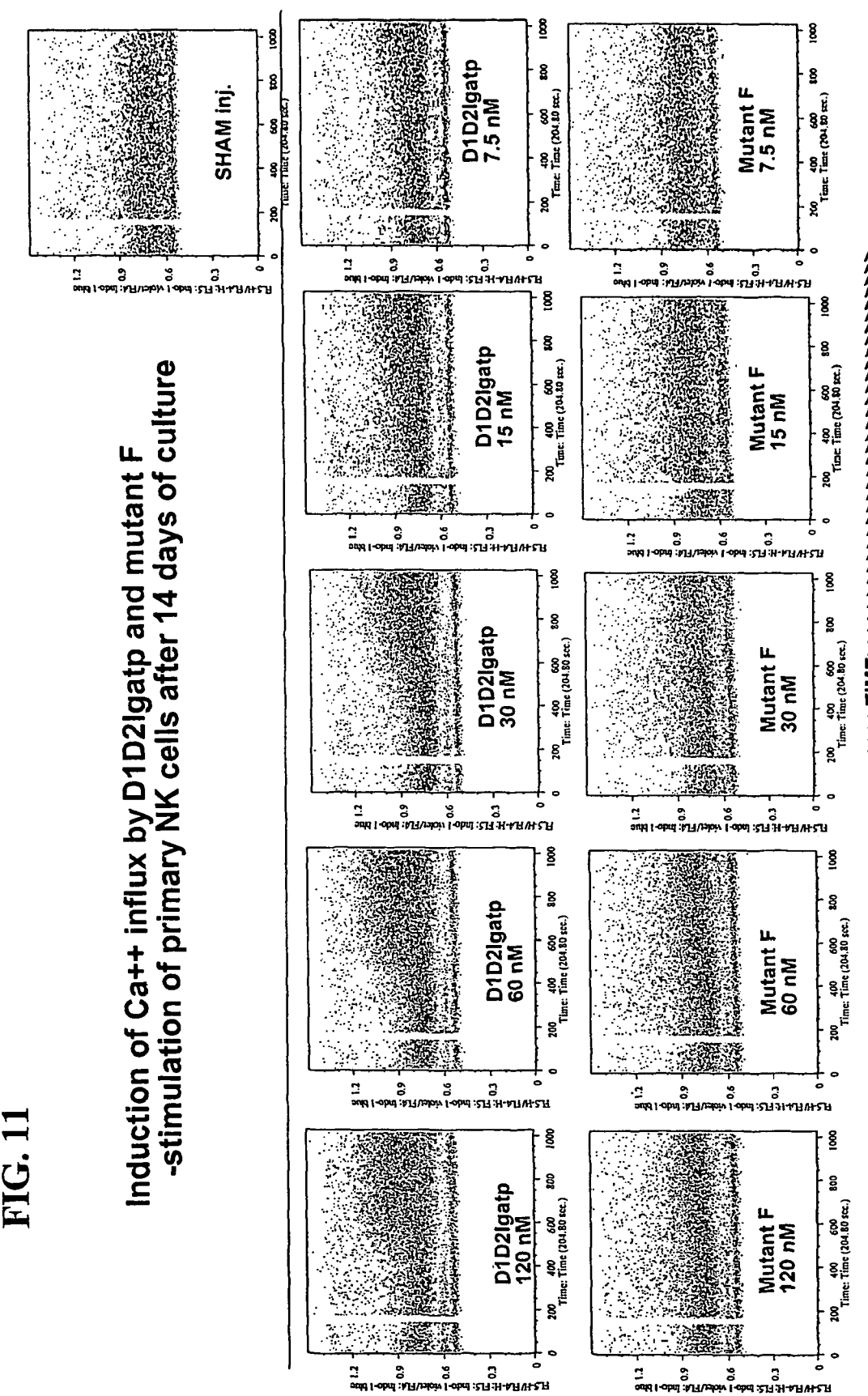

Representative plots showing the induction of a calcium flux by D1D2-Igαtp or FD1D2-Igαtp (mutant F) in natural killer (NK) cells after the cells were cultured in vitro for 14 days are shown in FIG. 11. The negative control (SHAM, FIG. 11A) did not exhibit any calcium influx, while application of different concentrations of D1D2-Igαtp (FIGS. 11B-F, 120 nm, 60 nm, 30 nm, 15 nM, and 7.5 nM, respectively) elicited a calcium influx. Mutant F application did not induce a calcium influx (FIG. 11GK, 120 nm, 60 nm, 30 nm, 15 nM, and 7.5 nM, respectively), indicated that this molecule does not activate natural killer cells.

The results demonstrate that as D1D2-Igαtp has a high affinity for the Fc receptor, there is resulting enhanced signal transduction through the CD16 receptor on human primary natural killer (NK) cells. This signal transduction induced by D1D2-Igαtp in NK cells that are of a substantially greater magnitude than signals delivered by human IgG1 antibodies (See FIG. 11).

Example 14

D1D2-Igαtp Mediates Cytoxicity of HIV Infected Cells

Fluorescence activated cell sorting analyses were performed to demonstrate that D1D2-Igαtp mediates antibody dependent cell mediated cytoxicity. HIV-infected CEM-.NRK target cells were incubated in the presence of NK cells with either D1D2-Igαtp or in media alone. Cells were subsequently labeled with propidium iodide, which measures cell viability (viable cells exclude propidium iodide).

Figure 13:
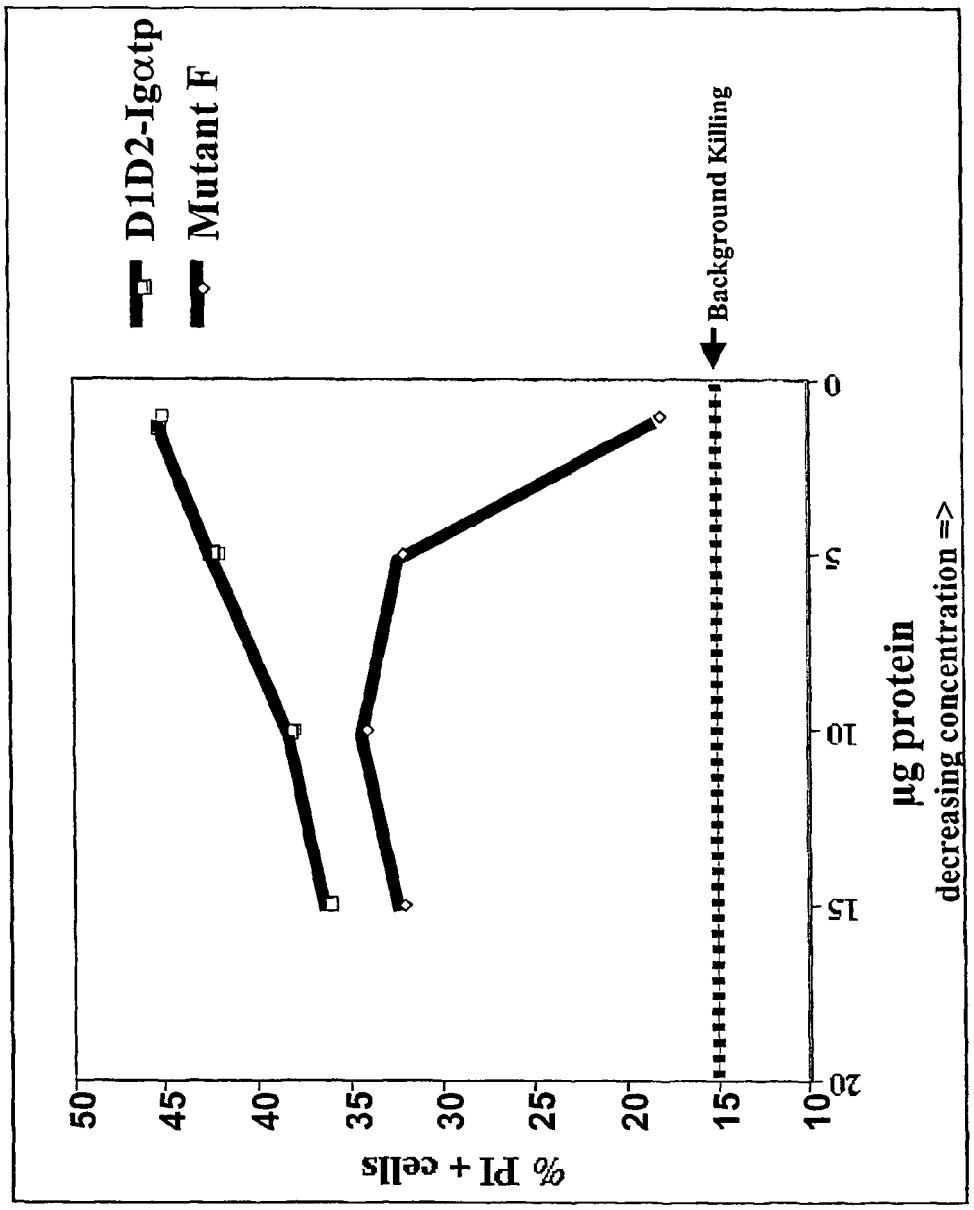
FIG. 13 is a line graph showing the percent of PI positive cells obtained after incubation of HIV-infected CEM.NRK target cells with NK cells in the presence of either D1D2-Igαtp or FD1D2-Igαtp (labeled "mutant F"). Both D1D2-Igαtp and FD1D2-Igαtp induced killing, although D1D2-Igαtp was more effective.

In the presence of D1D2-Igαtp, 45% of the HIV-1 infected cells were killed by the NK cells, whereas without application of D1D2-Igαtp, only 15% of the cells were killed. The same number of uninfected CEM.NRK cells survived in the presence of D1D2-Igαtp as compared to uninfected CEM.NRK cells incubated in the absence of antibody (FIG. 12). Thus, D1D2-Igαtp mediates NK cell mediated antibody dependent cell mediated cytoxicity. The percent of PI positive cells obtained after incubation of HIV-infected CEM.NRK target cells with either D1D2-Igαtp or mutant F (FD1D2-Igαtp) was compared (FIG. 13). Both D1D2-Igαtp and mutant F induced killing, although D1D2-Igαtp was more effective.

In view of the many possible embodiments to which the principles of this disclosure may be applied, it should be recognized that the illustrated embodiment is only a preferred example of the invention and should not be taken as a limitation on the scope of the invention. Rather, the scope of the invention is defined by the following claims. We therefore claim as our invention all that comes within the scope and spirit of these claims.

We claim:

1. A recombinant polypeptide comprising a CD4 polypeptide ligated at its C-terminus with an immunoglobulin polypeptide, wherein the immunoglobulin polypeptide comprises a hinge region and a constant domain of a mammalian immunoglobulin heavy chain, and wherein the immunoglobulin polypeptide is fused at its C-terminus with a tailpiece polypeptide from the C terminus of the heavy chain of an IgA antibody or a tailpiece from a C terminus of the heavy chain of an IgM antibody.

2. The recombinant polypeptide of claim 1, wherein the CD4 polypeptide comprises the D1 and D2 regions of a human CD4 polypeptide.

3. The recombinant polypeptide of claim 1, wherein the immunoglobulin polypeptide is a human IgG molecule.

4. The recombinant polypeptide of claim 3, wherein the immunoglobulin polypeptide is an IgG$_1$, IgG$_2$ or an IgG$_3$, or a combination thereof.

5. The recombinant polypeptide of claim 4, wherein the tailpiece polypeptide comprises the tailpiece from the C terminus of the heavy chain of an IgA antibody.

6. The recombinant polypeptide of claim 1, wherein the constant domain comprises a CH2 domain.

7. The recombinant polypeptide of claim 6, wherein the constant domain further comprises a CH3 domain.

8. The recombinant polypeptide of claim 1, comprising a polypeptide linker between the CD4 polypeptide and the inununoglobulin polypeptide.

9. A composition comprising the recombinant polypeptide of claim 1 in a carrier.

10. A kit for treatment or prevention of HIV infection, comprising a container comprising an effective amount of the recombinant polypeptide of claim 1.

11. A multimeric polypeptide comprising monomers of the recombinant polypeptide of claim 5.

12. The multimeric polypeptide of claim 11, wherein the multimer is a dodecylmer.

13. The recombinant polypeptide of claim 5, comprising SEQ ID NO: 1.

14. The recombinant polypeptide of claim 13, wherein the immunoglobulin is an IgG$_1$.

15. The recombinant polypeptide of claim 13, wherein the polypeptide comprises SEQ ID NO: 6 or SEQ ID NO: 11.

16. The recombinant polypeptide of claim 13, wherein the polypeptide consists of SEQ ID NO: 6 or SEQ ID NO: 11.

* * * * *